US011185456B2

(12) United States Patent
Hiratsuka et al.

(10) Patent No.: US 11,185,456 B2
(45) Date of Patent: Nov. 30, 2021

(54) MEDICAL SYSTEM INCLUDING MEDICAL IMAGING DEVICE AND ROBOTIC BED

(71) Applicant: MEDICAROID CORPORATION, Kobe (JP)

(72) Inventors: Mitsuichi Hiratsuka, Kobe (JP); Yoshiyuki Tamura, Kobe (JP); Tetsuya Nakanishi, Kobe (JP); Yukihiko Kitano, Kobe (JP); Yutaro Yano, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 709 days.

(21) Appl. No.: 16/004,040

(22) Filed: Jun. 8, 2018

(65) Prior Publication Data
US 2018/0289575 A1   Oct. 11, 2018

Related U.S. Application Data

(63) Continuation of application No. PCT/JP2016/086780, filed on Dec. 9, 2016.

(30) Foreign Application Priority Data

Dec. 11, 2015 (WO) .................. PCT/JP2015/006207
Dec. 11, 2015 (WO) .................. PCT/JP2015/006208
Dec. 11, 2015 (WO) .................. PCT/JP2015/006209

(51) Int. Cl.
*A61B 6/04* (2006.01)
*A61B 6/00* (2006.01)
(Continued)

(52) U.S. Cl.
CPC ............ *A61G 13/104* (2013.01); *A61B 5/055* (2013.01); *A61B 6/045* (2013.01); *A61B 6/0407* (2013.01);
(Continued)

(58) Field of Classification Search
CPC .... A61G 13/104; A61G 13/04; A61G 13/101; A61G 2210/50; A61B 90/50;
(Continued)

(56) References Cited

U.S. PATENT DOCUMENTS 5,410,767 A    5/1995  Barud
6,502,261 B1 * 1/2003  Harwood ............... A61G 13/02
                                                        5/611
(Continued)

FOREIGN PATENT DOCUMENTS

EP    1985237 A1   10/2008
EP    2135554 A1   12/2009
(Continued)

OTHER PUBLICATIONS

Eric A. Harris, "Sedation and Anesthesia Options for Pediatric Patients in the Radiation Oncology Suite", International Journal of Pediatrics, vol. 2010, Article ID 870921,9 pages, 2010. https://doi.org/10.1155/2010/870921 (Year: 2010).*

(Continued)

*Primary Examiner* — David R Hare
*Assistant Examiner* — Madison Emanski
(74) *Attorney, Agent, or Firm* — Metrolex IP Law Group, PLLC

(57) ABSTRACT

In a medical system including a medical imaging device and a robotic bed, the table may be movable between a first position where a maximum dimension of the robot arm not hidden under the table is less than one fourth of a longitudinal dimension of the table when the table is viewed from vertically above, and a second position where a maximum dimension of the robot arm not hidden under the table is one fourth of a longitudinal dimension of the table or more when the table is viewed from vertically above. The second position may be an imaging position or an imaging prepa- (Continued)

ration position where an image is taken by the medical imaging device. The first position may be surgery position where a shortest distance between the robotic bed and a location of the medical imaging device is at least a predetermined distance.

20 Claims, 42 Drawing Sheets

(51) Int. Cl.
  *A61B 5/055* (2006.01)
  *A61G 13/06* (2006.01)
  *A61G 13/10* (2006.01)
  *A61G 13/04* (2006.01)
  *A61B 90/50* (2016.01)
  *A61B 8/00* (2006.01)

(52) U.S. Cl.
  CPC ............ *A61B 6/0487* (2020.08); *A61B 6/547* (2013.01); *A61B 8/40* (2013.01); *A61B 90/50* (2016.02); *A61G 13/04* (2013.01); *A61G 13/06* (2013.01); *A61G 13/101* (2013.01); *A61G 2210/50* (2013.01)

(58) Field of Classification Search
  CPC ..... A61B 6/0487; A61B 5/055; A61B 6/0407; A61B 6/045; A61B 6/547
  See application file for complete search history.

(56) References Cited

U.S. PATENT DOCUMENTS

| | | | | |
|---|---|---|---|---|
| 8,051,515 | B1* | 11/2011 | Kring | A61G 13/101 5/658 |
| 2004/0098804 | A1* | 5/2004 | Varadharajulu | A61G 13/04 5/611 |
| 2005/0228255 | A1 | 10/2005 | Saracen et al. | |
| 2005/0234327 | A1* | 10/2005 | Saracen | A61B 6/548 600/407 |
| 2007/0163322 | A1 | 7/2007 | Hirakawa et al. | |
| 2007/0232894 | A1* | 10/2007 | Feenan | G01R 33/307 600/410 |
| 2008/0235873 | A1* | 10/2008 | Farooqui | A47B 9/16 5/601 |
| 2009/0070935 | A1* | 3/2009 | Brunker | H02P 31/00 5/601 |
| 2011/0066278 | A1 | 3/2011 | Pinault et al. | |
| 2012/0029694 | A1 | 2/2012 | Muller | |
| 2013/0077765 | A1* | 3/2013 | Welsh | A61B 6/588 378/198 |

FOREIGN PATENT DOCUMENTS

| | | | | |
|---|---|---|---|---|
| JP | S59-211465 | A | 11/1984 | |
| JP | H06-205809 | A | 7/1994 | |
| JP | H06-315424 | A | 11/1994 | |
| JP | H07-104826 | A | 4/1995 | |
| JP | H07-185024 | A | 7/1995 | |
| JP | H08-272866 | A | 10/1996 | |
| JP | H11-509461 | A | 8/1999 | |
| JP | 2005-185387 | A | 7/2005 | |
| JP | 2006-006589 | A | 1/2006 | |
| JP | 2008-167929 | A | 7/2008 | |
| JP | 2008-220553 | A | 9/2008 | |
| JP | 2008-539963 | A | 11/2008 | |
| JP | 2009-131718 | A | 6/2009 | |
| JP | 2010-094291 | A | 4/2010 | |
| JP | 2010094291 | | * 4/2010 | ............ A61B 5/055 |
| JP | 2010-099362 | A | 5/2010 | |
| JP | 2012-011498 | A | 1/2012 | |

OTHER PUBLICATIONS

"The Purpose of Servo Motors: Fuji Electric Product Column." Fuji Electric Global, www.fujielectric.com/products/column/servo/servo_01.html.*
Hitachi Medical Corporation, "Front-line system for total removal of brain tumor which allows increasing survival rate and ensuring postoperative QOL," Monthly Magazine(INNERVISION), Sep. 2012, JIYUKUKAN vol. 25(Appendix), Retrieved from the Internet: URL: http://www.innervision.co.jp/suite/hitachi/supplement/1209/pickup/index.html.
Hiroshi Iseki et al., "Intelligent Operating Theater and MR-compatible Operating System", Research Paper (MEDIX), 2001, p. 11-16, vol. 39.
Toshio Tsuchihashi, "Avoid attraction accident of 3T MRI", Monthly Magazine(INNERVISION), Sep. 2012.

* cited by examiner

MEDICAL SYSTEM INCLUDING MEDICAL IMAGING DEVICE AND ROBOTIC BED

CROSS-REFERENCE TO RELATED APPLICATIONS

This is a continuation of International Application No. PCT/JP2016/086780 filed on Dec. 9, 2016, which claims priority to International Application Nos. PCT/JP2015/006207 filed on Dec. 11, 2015, PCT/JP2015/006208 filed on Dec. 11, 2015, and PCT/JP2015/006209 filed on Dec. 11, 2015, the entire contents of which are incorporated herein by reference.

TECHNICAL FIELD

One or more embodiments relate to a medical system used in a hybrid operating room.

BACKGROUND ART

In recent years, a robot arm is used to support a table on which a patient is to be placed. The robot arm is also used to determine the position of the patient and transport the patient in the course of treatment.

Typically, from around 1997, robot arms start to get attention in the field of radiotherapy as a means for determining the position of a treatment table. From around 2005, patient positioning robotic systems have been applied for practical use (see, e.g., Japanese Unexamined Patent Publication No. 2009-131718 (Patent Document 1) and Japanese Unexamined Patent Publication No. 2008-220553 (Patent Document 2)). Currently, patient positioning robotic systems start to be used as a means for transferring the treatment table to a medical imaging device, such as an angiographic device (see, e.g., European Patent Publication No. EP 1985237 (Patent Document 3) and German Patent Publication No. US20120029694A1 (Patent Document 4)). Now, a system which employs a robotically supported table even during surgery is getting attention (see, e.g., Japanese Unexamined Patent Publication No. 2010-94291 (Patent Document 5)).

SUMMARY

The patient positioning robotic system seems to have been developed in the field of radiotherapy largely because the robot arm can be remote controlled away from exposure to harmful radiation. In general, a bulky system using a large robot arm needs to be configured in order to realize such a patient positioning robotic system. To achieve that, a treatment space and a large medical room are required.

Even in a case where a patient positioning robotic system is used to transfer the table to the medical imaging device, transportation efficiency and positioning accuracy are prioritized and space saving has not been a main point of consideration, because the purpose here is to take an image.

Moreover, operation tables which are capable of elevating and rotating and having a slidable top plate (see, e.g., Patent Document 5) are still used in most operations. Even in a case where a robotically supported table can be located at a surgery place as disclosed in European Patent Publication No. EP 2135554 (Patent Document 6), the main purpose of using such a table is to efficiently transport the patient among a plurality of positions and reduce costs. Thus, the system has not been developed for application in hospitals with only a limited space available.

One or more embodiments are therefore intended to provide a system for carrying out efficient and accurate hybrid surgery even in a limited space.

To solve the above problem, one or more embodiments may provide a medical system including a base, a table configured to support a table by a robot arm having movable elements coupled together by a joint, and a medical imaging device. The table may be movable between a first position where a maximum dimension of the robot arm not hidden under the table, when the table is viewed from vertically above, is less than one fourth of a longitudinal dimension of the table, and a second position where the maximum dimension of the robot arm not hidden under the table is one fourth of the longitudinal dimension of the table or more.

The second position may be an imaging position or an imaging preparation position where an image is taken by the medical imaging device. The first position may be surgery position where a shortest distance between the table and the medical imaging device is at least a predetermined distance.

DETAILED DESCRIPTION

In medical settings, efforts have been made to improve the medical settings for carrying out efficient and highly accurate treatment, inspection, measurement, etc., while maintaining safety in various scenes. One or more embodiments suggest introducing, into the medical settings, a robotic bed whose table, on which a target is to be placed, is supported by a robot arm having multiple degrees of freedom (i.e., three or more degrees of freedom) to enhance the efficiency and accuracy in the treatment, inspection, measurement, etc.

[Configuration of Robotic Bed]

First Example Configuration

Figure 1:
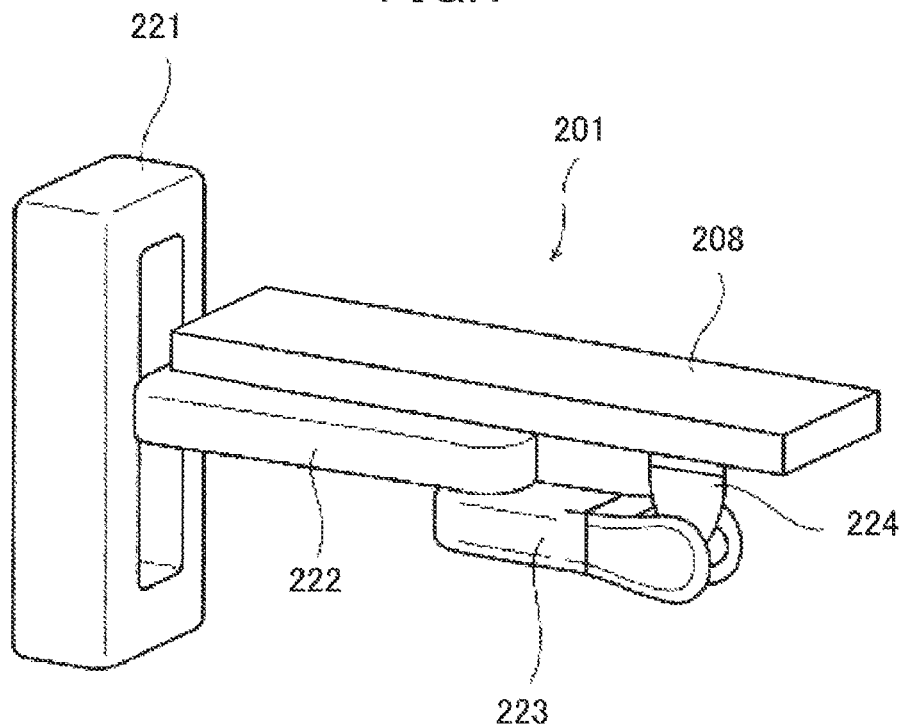
FIG. 1 is a diagram illustrating a perspective view of a robotic bed according to a first example configuration.
Figure 2:
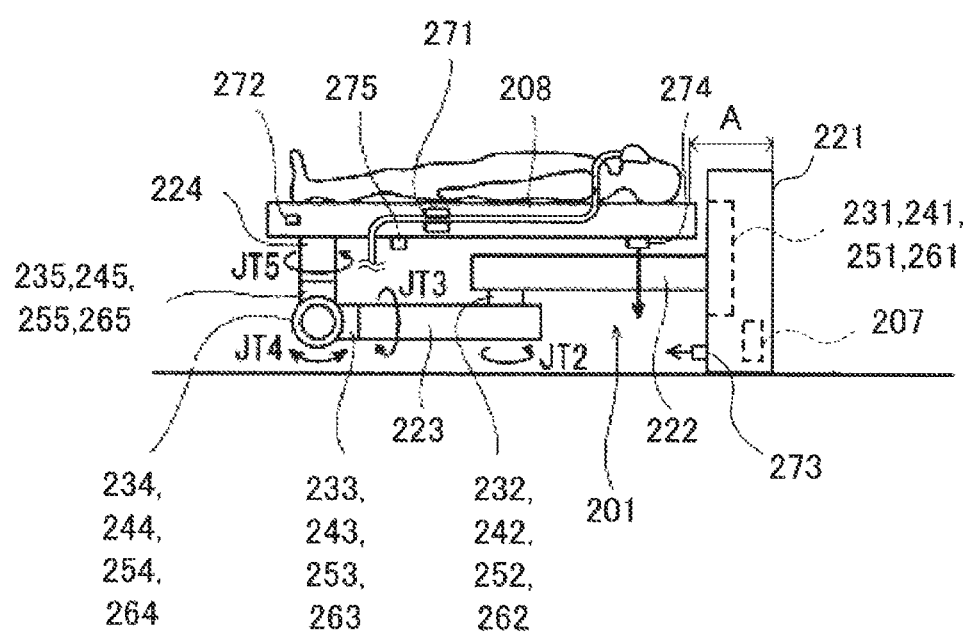
FIG. 2 is a diagram illustrating a side view of the robotic bed according to the first example configuration.

FIG. 1 is a diagram illustrating a perspective view, and FIG. 2 is a diagram illustrating a side view, of a robotic bed according to a first example configuration of one or more embodiments. A robot arm 201 used for the robotic bed has multiple degrees of freedom (i.e., three or more degrees of freedom), and has a distal end supporting a table 208 on which a target is placed. The table 208 and the robot arm 201 form the robotic bed.

As illustrated in FIG. 2, the robot arm 201 includes a base 221, a plurality of movable elements (first to third movable elements 222 to 224 in the present example configuration), and a plurality of joints (first to fifth joints 231 to 235 in the present example configuration).

The base 221 and one end portion of the first movable element 222 are coupled together by the first joint 231 traveling vertically straight, which enables the first movable element 222 to move in a first axial direction (i.e., in a vertical direction). The other end portion of the first movable element 222 and one end portion of the second movable element 223 are coupled together by a horizontally-rotating joint, which enables the second movable element 223 to rotate about a second axis (in the vertical direction). The third to fifth joints 233 to 235 between the second movable element 223 and the third movable element 224 are rotating joints which rotate about third to fifth axes, respectively. The third axis corresponds to a direction in which the second movable element 223 extends. The fourth axis corresponds to a direction orthogonal to the third axis about which the third joint 233 rotates. The fifth axis corresponds to a direction orthogonal to the fourth axis about which the fourth joint 234 rotates.

Each of the first movable element 222 and the second movable element 223 is a rod-like member extending in a particular direction, with its length appropriately designed according to a required range of movement of the robot arm 201. The "one end portion" of a movable element extending in a particular direction refers to either one of the two end regions when the movable element is equally divided into three regions in the particular direction (i.e., the longitudinal direction). The "other end portion" of the movable element extending in the particular direction refers to the end portion opposite to the one end portion of the two end regions of the three equally-divided regions of the movable element in the particular direction (i.e., the longitudinal direction). If it is simply called the "end portion," it refers to either the one end portion or the other end portion. The portion between both of the two end portions is called a "middle portion."

The first movable element 222 moves up and down, while staying parallel to the horizontal plane. The second movable element 223 rotates about the second axis, while staying parallel to the first movable element 222. This configuration does not require the second actuator 242 to compensate for the gravity in the vertical direction, and the motor may thus be reduced in size. This configuration is advantageous in downsizing the robot arm 201, and is advantageous in introducing the robot arm 201 in the medical settings where only a limited space is available, or in giving a larger space for treatment and surgery. For example, a ball screw may be employed as a configuration of the first joint 231 to which load is applied.

Further, the robotic bed according to the present example configuration is configured such that the table 208 does not come in contact with the robot arm 201, no matter how much (e.g., by 360 degrees) the table 208 is rotated while keeping the table 208 parallel to the horizontal plane, in a state in which particular directions (i.e., the longitudinal directions) of the first movable element 222 and the second movable element 223, which are coupled together at their end portions by a horizontally-rotating joint, are parallel to each other when viewed from vertically above. Specifically, the robotic bed according to the present example configuration is configured such that, in a state in which the first movable element 222 and the second movable element 223, which are coupled together at their end portions by a horizontally-rotating joint, and the table 208 are arranged parallel to the horizontal plane, the table 208 is not level with the other movable elements and is located at the top. In other words, in a state in which the distal end of the robot arm 201 is located at the lowermost position of its motion range and the table 208 takes a position parallel to the horizontal plane, the first and second movable elements of the robot arm 201 are lower than the lower surface of the table 208. Further, in the present example configuration, the base 221 is higher than the lower surface of the table 208 in order to provide a greater range of adjustment for the vertical movement of the table 208, even in a state in which the distal end of the robot arm 201 is located at the lowermost position of its motion range and the table 208 takes a position parallel to the horizontal plane. These configurations allow the movable elements of the robot arm 201 to be located and housed under the table 208, and hence allow effective use of a limited space in the medical settings while ensuring a broad range for the vertical movement of the table 208.

Further, for the purpose of space saving and in consideration of the size of the robot arm 201 enough to maintain the strength for supporting the table 208, the dimension A (see FIG. 2) in the longitudinal direction of the table 208 where the robot arm 201 is not hidden under the table 208 is preferably one fourth (i.e., ¼) or less of the longitudinal dimension of the table 208.

Figure 6:
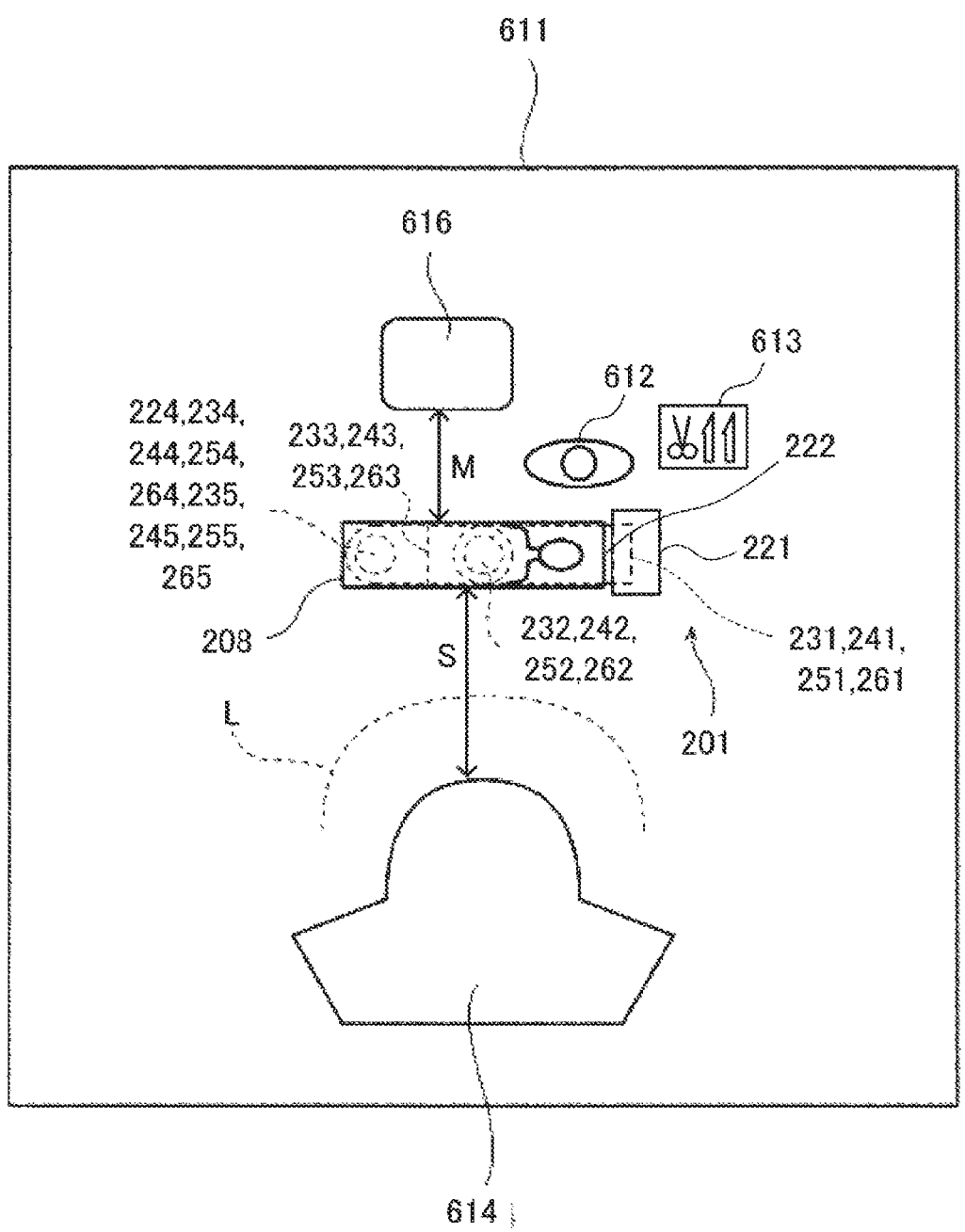
FIG. 6 is a diagram illustrating a plan view of a medical room where the robotic bed according to the first example configuration is placed, and shows a state in which the table is located at a first position.
Figure 7:
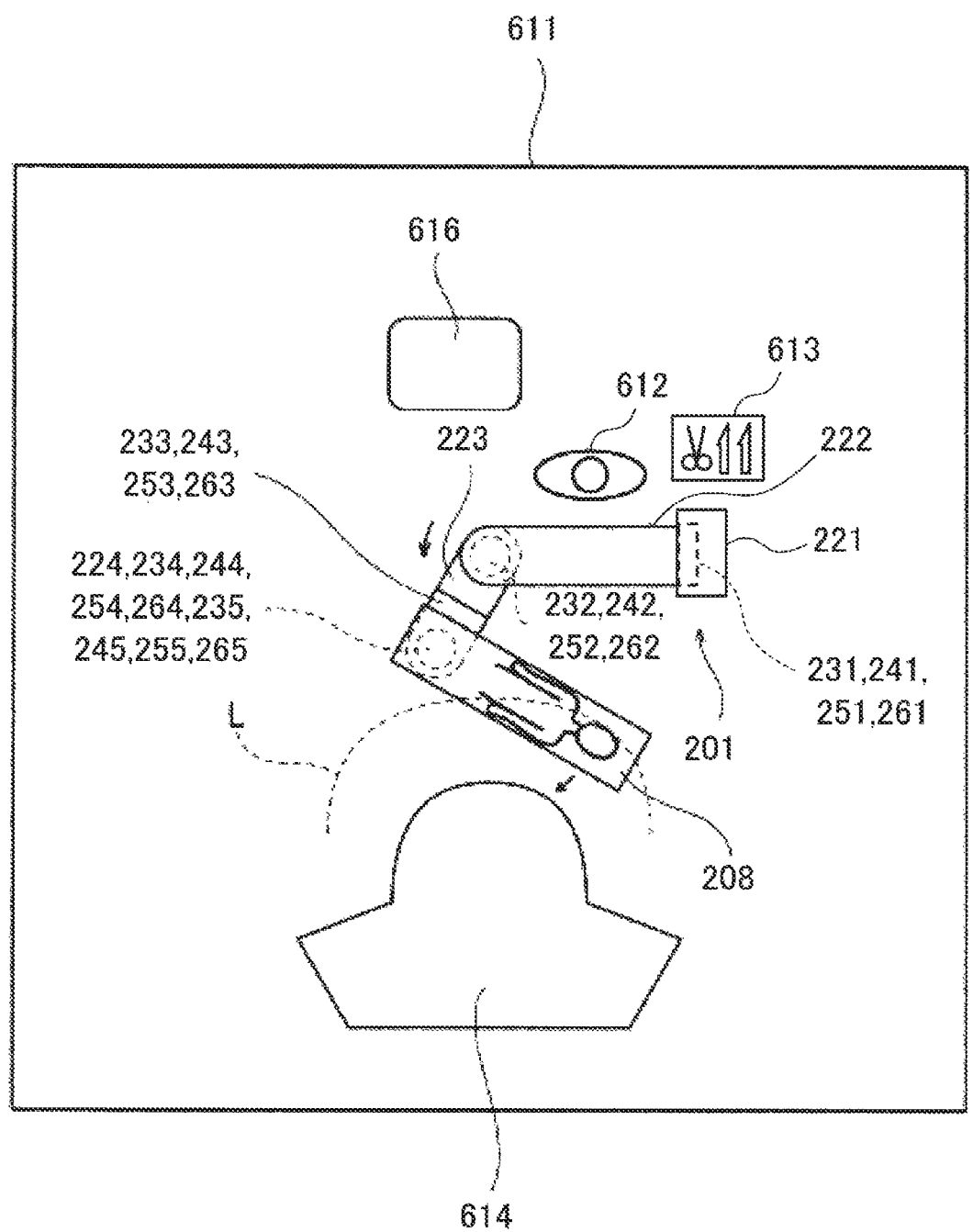
FIG. 7 is a diagram illustrating a plan view of the medical room where the robotic bed according to the first example configuration of the robot arm is placed, and shows the table in the middle of being transferred from the first position to the second position.
Figure 8:
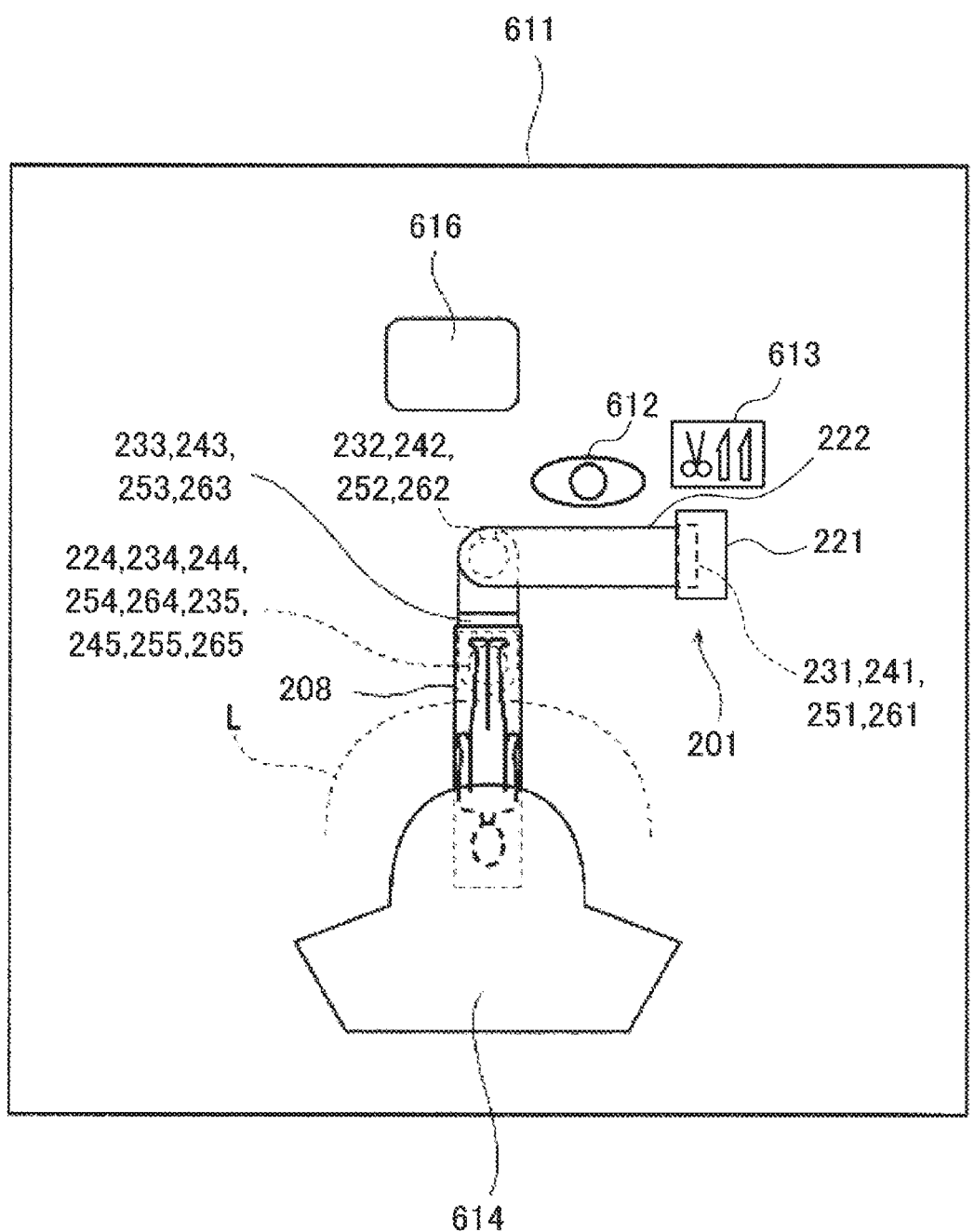
FIG. 8 is a diagram illustrating a plan view of the medical room where the robotic bed according to the first example configuration of the robot arm is placed, and shows a state in which the table is located at the second position.

Advantages of this configuration can be clearly seen from FIGS. 6 to 8 illustrating the movement of the robotic bed according to the first example configuration. As illustrated in FIG. 6, the robotic bed according to the present example configuration can take a position in which the respective movable elements and the table 208 overlap one another when viewed from vertically above. Thus, even in the case, for example, where the table is located as close to the base as possible in order to keep space for treatment, the movable elements do not constitute obstacles.

Preferably, the width of the table 208 is greater than the width of each of the movable elements of the robot arm 201. For example, it is preferable that in a state in which particular directions (i.e., the longitudinal directions) of the first movable element 222 and the second movable element 223, which are coupled together at their end portions by a horizontally-rotating joint, and a particular direction (i.e., the longitudinal direction) of the table 208 are parallel to one another when viewed from vertically above, the first movable element 222 and the second movable element 223 be hidden under the table 208 in the direction (i.e., the width direction of the table 208) orthogonal to the particular direction (i.e., the direction in which the longitudinal directions of the first movable element 222, the second movable element 223, and the table 208 are parallel to each other) at portions where the table 208 overlaps with the first movable element 222 and the second movable element 223 in the particular direction (i.e., the longitudinal direction) when viewed from vertically above. In this configuration, portions of the robot arm 201 (that is, in the example of FIG. 2, all of the first movable element 222 other than the one end portion thereof, and all of the second movable element 223 and the third movable element 224) which overlap with one another in the longitudinal direction of the table 208 are housed under the table 208 at least in the width direction of the table 208 (i.e., the direction orthogonal to the particular direction in which the table 208 extends) (see, e.g., FIG. 6).

In the examples illustrated in FIGS. 1 and 2, one (i.e., the first movable element 222) of the two movable elements (namely, the first movable element 222 and the second movable element 223) which are coupled together at their end portions by a horizontally-rotating joint is directly coupled to the base 221. However, the movable element may also be indirectly coupled to the base via another horizontally-rotating joint or a vertically-rotating joint. In this case, as well, the advantages of ensuring a larger space and downsizing the robot arm can be achieved, as long as the above-described positional relationship is maintained and the plurality of movable elements are housed under the table 208.

The third movable element 224 is provided at the distal end of the robot arm 201. In the present example configuration, the distal end of the robot arm 201 is fixed on a lower surface of the one end portion of the table 208 extending in the particular direction. This configuration allows the robot arm 201 to move such that the other end of the table 208 is positioned as far away from the base 221 as possible. Supporting the table 208 at its one end portion increases the movable range of the table 208. However, the table 208 may be supported at its middle portion if a priority is placed on the supporting strength.

The robot arm 201 includes: a plurality of actuators (first to fifth actuators 241 to 245 in the present example configuration) associated with the first to fifth joints 231 to 235 to move or rotate the first to third movable elements 222 to 224; a plurality of position detectors (first to fifth position detectors 251 to 255 in the present example configuration) built in the respective joints to detect the positions of the respective movable elements; and a controller 207 (see FIG. 2) which controls the actuation of the respective actuators. The controller 207 is provided in the base 221, but may also be an independent external device, for example.

The first to fifth actuators 241 to 245 are servomotors, for example. Encoders, resolvers, and potentiometers may be used as the position detectors.

Preferably, the robot arm 201 further includes first to fifth electromagnetic brakes 261 to 265 associated with the first to fifth joints 231 to 235. If the robot arm 201 does not include any electromagnetic brakes, the posture of the robot arm 201 is maintained by actuating the plurality of actuators 241 to 245. If the robot arm 201 includes the electromagnetic brakes, the posture of the robot arm 201 may be maintained by turning the electromagnetic brakes on even if some of the actuators are turned off.

In the case where the electromagnetic brakes are provided, each of the first to fifth electromagnetic brakes 261 to 265 is configured to turn its brake function on when no drive current is supplied to the associated one of the actuators, and to turn its brake function off when a drive current is supplied to the actuator.

Figure 3:
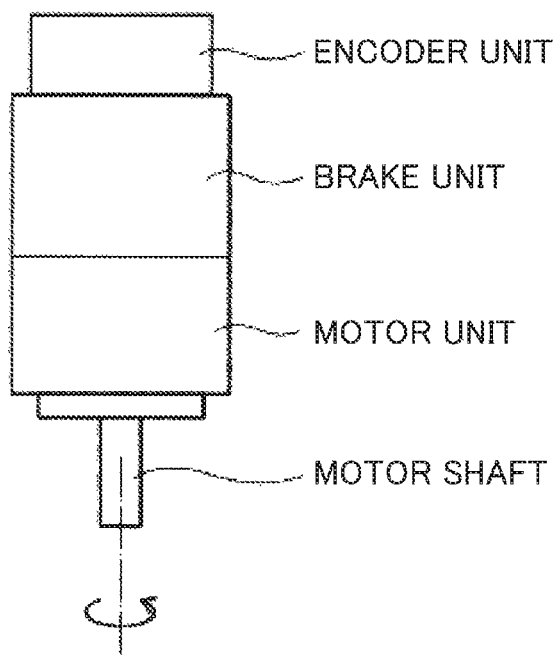
FIG. 3 is a diagram illustrating a conceptual view of an actuator, a position detector, and a braking mechanism configured as a single unit.

In many cases, a motor functioning as the actuator, an encoder functioning as the position detector, and the brake are integrated together as a unit as illustrated in FIG. 3. Further, each of the first to fifth actuators 241 to 245 is provided with a deceleration mechanism, a coupling, etc., for power transmission.

In the example illustrated in FIG. 2, the first movable element 222 is coupled by the horizontally-rotating joint 232 so as to be located above the second movable element 223. Illustrated in FIG. 4 as a variation of the present example configuration is a robot arm 401, the first movable element 422 of which is coupled by a horizontally-rotating joint 432 so as to be located below the second movable element 423.

In this variation, the base 421 and one end portion of the first movable element 422 are coupled together by the first joint 431 traveling vertically straight, which enables the first movable element 422 to move in a first axial direction (i.e., a vertical direction). The other end portion of the first movable element 422 and one end portion of the second movable element 423 are coupled together by a horizontally-rotating joint, which enables the second movable element 423 to rotate about a second axis (the vertical direction) above the first movable element 422. Third to fifth joints 433 to 435 between the second movable element 423 and the third movable element 424 are rotating joints which rotate about third to fifth axes, respectively. The third axis corresponds to a direction in which the second movable element 423 extends. The fourth axis corresponds to a direction orthogonal to the third axis about which the third joint 433 rotates. The fifth axis corresponds to a direction orthogonal to the fourth axis about which the fourth joint 434 rotates.

The third movable element 424 is provided at the distal end of the robot arm 401. In the present example configuration, the distal end of the robot arm 401 is fixed on a lower surface of a middle portion of the table 408 extending in the particular direction. This configuration allows supporting the table 408, while placing a priority on the supporting strength. Of course, the table 408 may be supported at its one end portion to place a priority on the movable range of the table 408. In that case, however, it is necessary to determine the dimensions of the respective movable elements 422 to 424 and the table 408 appropriately in order to avoid contact with the robot arm 401 even when the table 408 is freely rotated while staying parallel to the horizontal plane.

Figure 4:
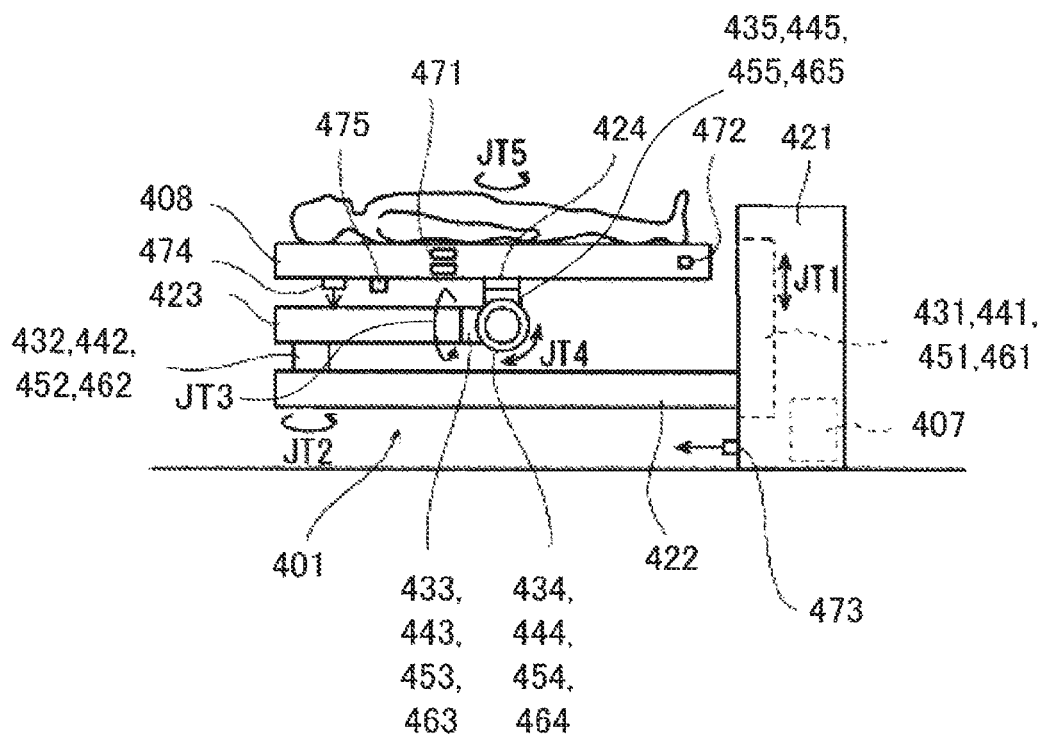
FIG. 4 is a diagram illustrating a perspective view of a robotic bed according to a variation of the first example configuration.
Figure 5:
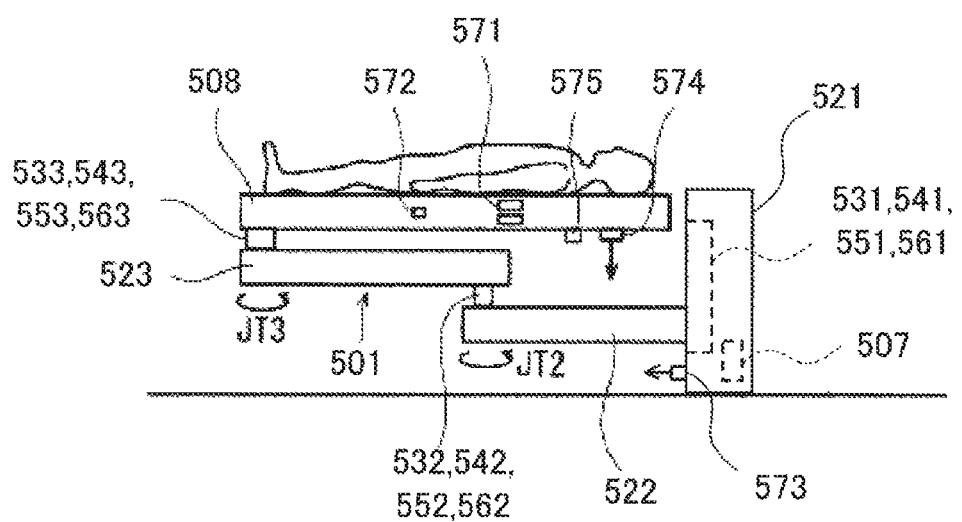
FIG. 5 is a diagram illustrating a side view of a robotic bed configured to have a minimum degree of freedom according to the first example configuration.

The robot arms 201 and 401 illustrated in FIGS. 2 and 4 have 5 degrees of freedom. However, the degrees of freedom of the robot arm of one or more embodiments do not have to be 5, and may be 4 or less or 6 or more. Nevertheless, it is preferable that the degrees of freedom of the robot arm be 3 or more so that the tables 208 and 408 can move at least in a straight manner in the room. FIG. 5 illustrates an example robotic bed having 3 degrees of freedom. In FIG. 5, the robot arm 501 is comprised of a base 521 and two movable elements 522 and 523. The base 521 and one end portion of the first movable element 522 are coupled together by a first joint 531 traveling vertically straight, which enables the first movable element 522 to move in a first axial direction (i.e., a vertical direction). The other end portion of the first movable element 522 and one end portion of the second movable element 523 are coupled together by a second joint 523, which is a horizontally-rotating joint enabling the second movable element 523 to rotate about a second axis (i.e., the vertical direction). The other end of the second movable element 523 serves as the distal end of the robot arm 501, and is coupled to one end portion of the table 508 by a third joint 533, which is a horizontally-rotating joint.

The robotic bed having the above configuration makes it possible to move the tables 208, 408, and 508, on which a target has been placed, to a target position, such as an inspection position and a treatment position, accurately and quickly, thus achieving significant improvement in the efficiency of the inspection and treatment in the medical settings. For example, compared to the configuration in which a table with a caster is used to move the patient, the tables 208, 408, and 508 can be moved more smoothly without shaking the patient too much, and may be prevented from being tangled with a lot of cords of medical equipment and the tubes of medical instruments which run on the floor of the medical room, and may be prevented from being wobbled by stepping over the cords and tubes. Thus, safety and transfer efficiency can be improved.

Further, in the robotic bed according to the present example configuration, the movable elements indicated by the reference characters 223, 423, and 523 are coupled to the table indicated by the reference character 508 by the joints indicated by the reference characters 232, 432, 532, and 533, each of which is a horizontally-rotating joint that enables the movable elements and the table to rotate while always staying parallel to the horizontal plane. This configuration thus provides greater stiffness, compared to the case where each of the movable elements and the table are coupled by a vertically-rotating joint. Specifically, if the movable element and the table are coupled together by a vertically-rotating joint, the posture may not be completely maintained by only the control by the actuator, and sagging may occur, due to, for example, the weight of the placed target, while the table is being moved or staying in a certain posture. The horizontally-rotating joint, on the other hand, does not rotate in the vertical direction, and therefore such sagging hardly occurs. Moreover, it is not necessary to take a vertical rotation into account at a portion where the horizontally-rotating joint, which always enables rotation parallel to the horizontal plane, is provided. Thus, the electromagnetic brake may be omitted even in consideration of a situation in which the power is turned off. In this manner, the present example configuration has greater stiffness and also contributes to providing a larger treatment space, and is designed to be more suitable as a robotic bed used in a medical room.

Examples of the target positions of the robotic bed include: a placement position where a target, such as a human being and an animal, is placed on the robotic bed; an inspection position where an inspection is conducted using specific inspection equipment or measurement equipment; an imaging position where an image of a specific site of the placed target is taken by CT, MRI, angiography, etc.; a treatment preparation position where a nurse or other staff gives medical attention to the patient before treatment; and a treatment position (including the surgery position) where a doctor and an assistant give treatment (including surgery). The robotic bed may be moved to different positions even for the same purpose, if, for example, different treatments need to be given at a plurality of sites. Specifically, the robotic bed may be used, for example, as follows: the table may be moved to the inspection position to inspect the placed target for any objects, like an implant, which affect MRI, before being moved to the MRI scanning position; the table may be moved to the inspection position to detect an amount of radioactive substances deposited using a detector, before the patient, who is a placed target, is moved to the surgery position; the patient, who is a placed target, may be moved to the inspection position to check his/her skin condition, before the patient is moved to the surgery position for skin surgery; and the table may be moved to the imaging position for brain tomography by an MRI apparatus, before being moved to the surgery position for surgery removing a brain tumor.

The movements of the table 208 supported by the robot arm 201 of the present example configuration between the plurality of positions will be described with reference to FIGS. 6 to 8.

FIG. 6 illustrates a state in which the table 208 is located at the placement position (i.e., a first position) in the process of moving a subject, who is a placed target, from the placement position to the inspection position. FIG. 7 illustrates a state in which the second movable element 223 and the table 208 are moved by the control of the controller 207 as the arrows indicate (in some cases, the first movable element 222, too, is moved in the vertical direction to have its height adjusted, and the table 208 is rotated about the third axis and/or the fourth axis to have its tilt with respect to the longitudinal direction and/or the width direction of the table finely adjusted), causing the head of the subject to move toward the inspection device 614 from an oblique angle. FIG. 8 illustrates a state in which the table 208 is inserted in the inspection device 614, and the subject has arrived at the inspection position (i.e., a second position). Note that the position (i.e., the first position) of the table 208 illustrated in FIG. 6 can also be the treatment position. From the inspection position (i.e., the second position) illustrated in FIG. 8, the respective movable elements move in reverse direction until the table 208 returns to the position illustrated in FIG. 6, where a doctor 612 can give a treatment based on the result of the inspection that has just been conducted.

The robot arm 501 illustrated in FIG. 5, as well, enables the table 508 to follow a similar path. Turning to the robot arm 401 illustrated in FIG. 4, the table 408 can arrive at the inspection position by rotating the second movable element 423 and the table 408 in the direction opposite to the direction indicated by the arrows shown in FIG. 7 (in some cases, the first movable element 422, too, moves in the vertical direction to have its height adjusted, and the table 408 is rotated about the third axis and/or the fourth axis to have its tilt with respect to the longitudinal direction and/or the width direction of the table finely adjusted).

The movement of the table 208, 408, 508 by the robot arm 201, 401, 501 between the respective positions may be achieved by, for example, giving an instruction to move the movable elements of the robot arm 201, 401, 501 to the controller 207, 407, 507 through an instruction device, such as a teaching pendant. Alternatively, the respective positions, such as the treatment position and the inspection position, may be stored in the controller 207, 407, 507 in advance. In this configuration, simply giving, for example, a forward-movement instruction to the controller makes the movable elements work in such a manner that allows the table to move to the target position while following the shortest path. The table 208, 408, 508 can thus be moved to the target position more quickly and smoothly. Further, the target position and some points on the intended path to the target position may be designated. In this configuration, the table may automatically travel along the intended path and arrive at the target position by simply giving, for example, a movement start instruction to the controller 208, 408, 508. To record the respective positions, the respective positions may be directly stored by actually guiding the robot arm 201, 401, 501 to the target position through the teaching pendant. Alternatively, the respective positions may be designated by inputting their x, y and z coordinates. Note that the instruction device is not limited to the teaching pendant, and may also be a hand-held, a remote controller, or the like.

Second Example Configuration

Figure 9:
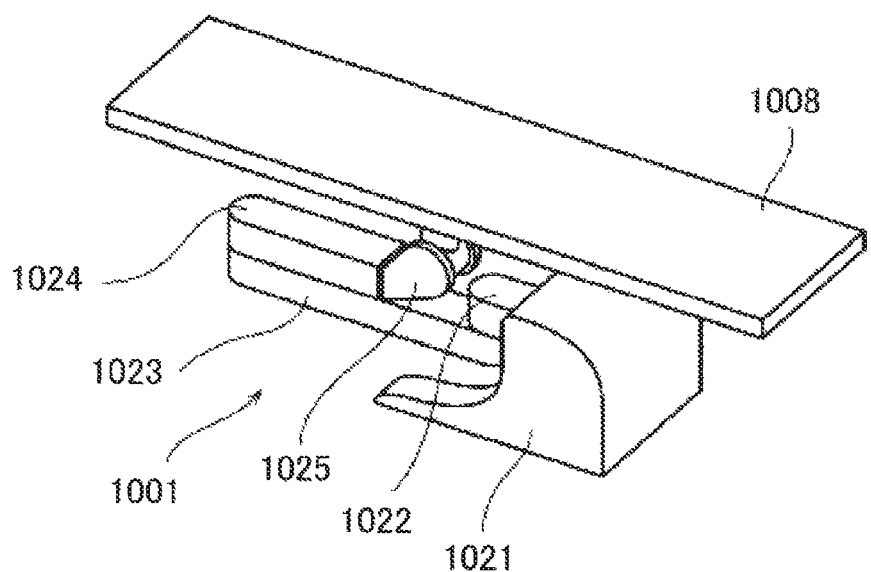
FIG. 9 is a diagram illustrating a perspective view of a robotic bed according to a second example configuration.
Figure 10:
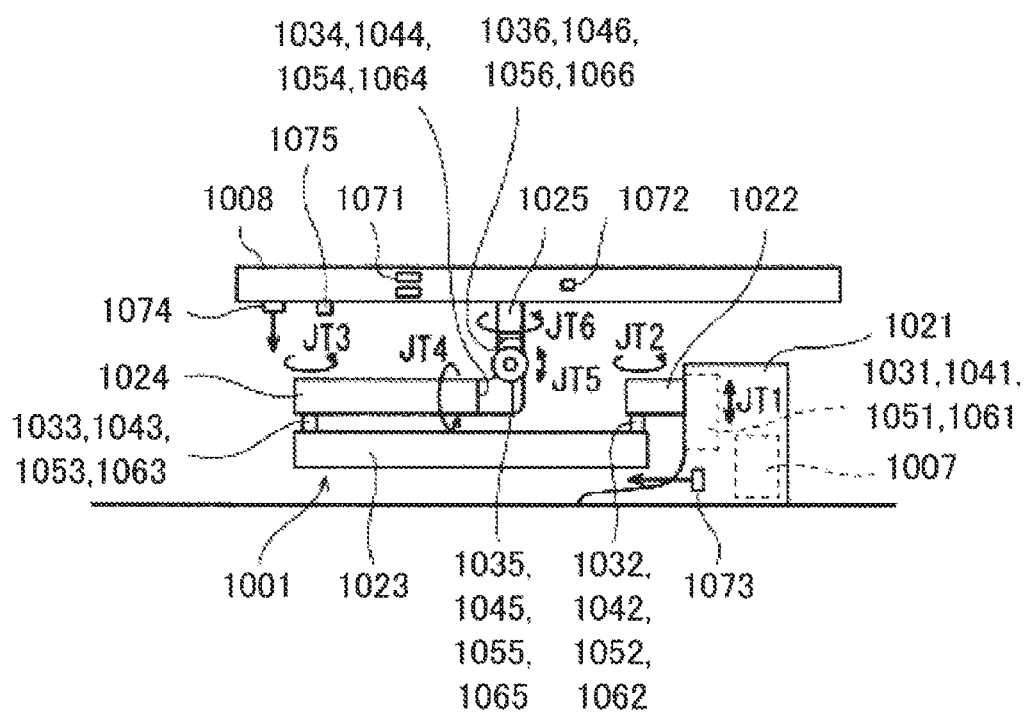
FIG. 10 is a diagram illustrating a side view of the robotic bed according to the second example configuration.

FIG. 9 is a diagram illustrating a perspective view, and FIG. 10 is a diagram illustrating a side view, of a robotic bed according to a second example configuration of the one or more embodiments. A robot arm 1001 used for the robotic bed has multiple degrees of freedom (i.e., three or more degrees of freedom), and has a distal end supporting a table 1008 on which a target is placed. The table 1008 and the robot arm 1001 form the robotic bed.

As illustrated in FIG. 10, the robot arm 1001 includes a base 1021, a plurality of movable elements (first to fourth movable elements 1022 to 1025 in the present example configuration), and a plurality of joints (first to sixth joints 1031 to 1036 in the present example configuration).

The base 1021 and one end portion of the first movable element 1022 are coupled together by a first joint 1031 traveling vertically straight, which enables the first movable element 1022 to move in a first axial direction (i.e., a vertical direction). The other end portion of the first movable element 1022 and one end portion of the second movable element 1023 are coupled together by a horizontally-rotating joint, which enables the second movable element 1023 to rotate about a second axis (i.e., the vertical direction). The other end portion of the second movable element 1023 and one end portion of the third movable element 1024 are coupled together by a horizontally-rotating joint, which enables the third movable element 1024 to rotate about a third axis (i.e., the vertical direction) that is rotated by, and parallel to, the second axis. The fourth to sixth joints 1034 to 1036 between the third movable element 1024 and the fourth movable element 1025 are rotating joints which rotate about fourth to sixth axes, respectively. The fourth axis corresponds to a direction in which the third movable element 1024 extends. The fifth axis corresponds to a direction orthogonal to the fourth axis about which the fourth joint 1034 rotates. The sixth axis corresponds to a direction orthogonal to the fifth axis about which the fifth joint 1035 rotates.

Each of the second movable element 1023 and the third movable element 1024 is a rod-like member extending in a particular direction, with its length appropriately designed according to a required range of movement of the robot arm 1001. The first movable element 1022 moves up and down, while staying parallel to the horizontal plane. The second movable element 1023 and the third movable element 1024 rotate, while staying parallel to the first movable element 1022. This configuration does not require the second and third actuators 1042 and 1043 to compensate for the gravity in the vertical direction, and the motor may thus be reduced in size. This configuration is advantageous in downsizing the robot arm 1001, and is advantageous in introducing the robot arm 1001 in the medical settings where only a limited space is available, or in ensuring a larger space for treatment and surgery.

Further, in the robotic bed of the present example configuration, the height of the base 1021 is reduced instead of limiting the range of movement of the first movable element 1022 by the first joint in the vertical direction. The reduction in height of the base 1021 prevents the table 1008 from coming into contact with the robot arm 1001, even when the first movable element 1022 is moved up and down (i.e., in the vertical direction) with the table 1008 maintained parallel to the horizontal plane, or no matter how much (e.g., 360 degrees) the table 1008 is rotated. Thus, in the present example configuration, the table and the robot arm do not come into contact with each other, no matter what posture the robot arm has, or how much the table 1008 is rotated, as long as the table 1008 is maintained parallel to the horizontal plane. Specifically, the robot arm of this example is configured such that the table 1008 is not level with any movable elements, nor with the base 1021, and is located at the top, even when the first movable element 1022 is moved to the lowermost position, and even when the distal end of the robot arm is located at the lowermost position, in a state in which the second movable element 1023 and the third movable element 1024, which are coupled together at their end portions by a horizontally-rotating joint, and the table 1008 are parallel to the horizontal plane. These configurations allow the movable elements of the robot arm 1001 and the base 1021 to be located and housed under the table 1008, and hence allow effective use of a limited space of the medical settings.

Preferably, the width of the table 1008 is greater than the width of each of the movable elements of the robot arm 1001. For example, it is preferable that all the movable elements may be hidden under the table 1008 when viewed from vertically above, in a state in which particular directions (i.e., the longitudinal directions) of the second movable element 1023 and the third movable element 1024, which are coupled together at their end portions by a horizontally-rotating joint, are parallel to each other when viewed from vertically above. Further, in this example configuration, it is preferable that the length of the table 1008 is longer than the length of each of the movable elements of the robot arm 1001. For example, it is preferable that the base 1021 be hidden under the table 1008 when viewed from vertically above, in a state in which particular directions (i.e., the longitudinal directions) of the second movable element 1023 and the third movable element 1024, which are coupled together at their end portions by a horizontally-rotating joint, are parallel to each other when viewed from vertically above, and in which the middle portions of the second movable element 1023 and the third movable element 1024 overlap with each other when viewed from vertically above.

In the examples illustrated in FIGS. 9 and 10, one (i.e., the second movable element 1023) of the two movable elements (namely, the second movable element 1023 and the third movable element 1024) which are coupled together at their end portions by a horizontally-rotating joint is indirectly coupled to the base 1021 (via the first movable element 1031). However, the second movable element 1023 may be directly connected, for example, to the first joint 1031 traveling vertically straight, or may be more indirectly connected to the base via another horizontally-rotating joint or a vertically-rotating joint. In this case, as well, the advantages of ensuring a larger space and downsizing the robot arm are achieved, as long as the above-described positional relationship is maintained.

The fourth movable element 1025 is provided at the distal end of the robot arm 1001. In the present example configuration, the distal end of the robot arm 1001 is fixed on a lower surface of a middle portion of the table 1008 extending in a particular direction. This configuration allows the robot arm 1001 to support the table 1008 with great supporting strength, and makes it easier to house the movable elements of the robot arm 1001, and the base, under the table 1008. Note that the length of the third movable element 1024 may be shortened, for example, so that the table 1008 is supported at its one end. In this case, as well, the advantages of ensuring a larger space and downsizing the robot arm are achieved.

The definitions of the "one end portion," "other end portion," "end portion" and "middle portion" as adopted in the above description are the same as, or similar to, those adopted in the first example configuration.

The robot arm 1001 includes: a plurality of actuators (first to sixth actuators 1041 to 1046 in the present example configuration) associated with the first to sixth joints 1031 to 1036 to move or rotate the first to fourth movable elements 1022 to 1025; a plurality of position detectors (first to sixth position detectors 1051 to 1056 in the present example configuration) built in the respective joints to detect the positions of the respective movable elements; and a controller 1007 (see FIG. 10) which controls the actuation of the respective actuators. The controller 1007 is provided in the base 1021, but may also be an independent external device, for example.

The first to sixth actuators 1041 to 1046 are servomotors, for example. Similarly to the first example configuration, encoders, resolvers or potentiometers may be used as the position detectors.

Preferably, the robot arm 1001 further includes first to sixth electromagnetic brakes 1061 to 1066 associated with the first to sixth joints 1031 to 1036. If the robot arm 1001 does not include any electromagnetic brakes, the posture of the robot arm 1001 is maintained by actuating the plurality of actuators 1041 to 1046. If the robot arm 1001 includes the electromagnetic brakes, the posture of the robot arm 1001 may be maintained by turning the electromagnetic brakes on even if some of the actuators are turned off.

In the case where the electromagnetic brakes are provided, each of the first to sixth electromagnetic brakes 1061 to 1066 is configured to turn its brake function on when no drive current is supplied to the associated one of the actuators, and to turn its brake function off when a drive current is supplied to the actuator.

Similarly to the first example configuration, in many cases, a motor functioning as the actuator, an encoder functioning as the position detector, and the brake are integrated together as a unit as illustrated in FIG. 3. Further, each of the first to sixth actuators 1041 to 1046 is provided with a deceleration mechanism, a coupling, etc., for power transmission.

In the example illustrated in FIG. 10, the first movable element 1022 is coupled by the horizontally-rotating joint 1032 so as to be located above the second movable element 1023. However, the first movable element 1022 may be coupled by the horizontally-rotating joint 1032 so as to be located under the second movable element 1023. This configuration may compensate for the reduction in height of the base 1721.

Figure 11:
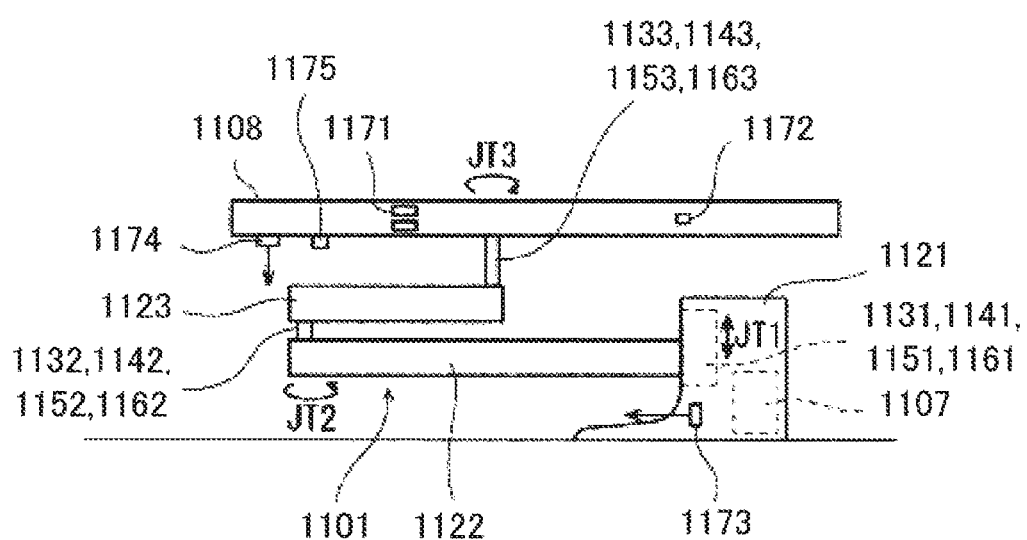
FIG. 11 is a diagram illustrating a side view of an example robotic bed configured to have a minimum degree of freedom according to the second example configuration.

The robot arm 1001 illustrated in FIGS. 9 and 10 has 6 degrees of freedom. However, the degrees of freedom of the robot arm of one or more embodiments do not have to be 6, and may be 5 or less or 7 or more. Nevertheless, it is preferable that the degrees of freedom of the robot arm be 3 or more so that the table 1008 can move at least in a straight manner in the room. FIG. 11 illustrates an example robotic bed according to the present configuration having 3 degrees of freedom. In FIG. 11, the robot arm 1101 is comprised of a base 1121 and two movable elements 1122 and 1123. The base 1121 and one end portion of the first movable element 1122 are coupled together by a first joint 1131 traveling vertically straight, which enables the first movable element 1122 to move in a first axial direction (i.e., a vertical direction). The other end portion of the first movable element 1122 and one end portion of the second movable element 1123 are coupled together by a second joint 1132, which is a horizontally-rotating joint enabling the second movable element 1123 to rotate about a second axis (i.e., the vertical direction). The other end of the second movable element 1123 serves as the distal end of the robot arm 1101, and is coupled to a lower surface of a middle portion of the table 1108 by a third joint 1133, which is a horizontally-rotating joint.

The robotic bed having the above configuration makes it possible to move the tables 1008 and 1108, on which a target has been placed, to a target position, such as an inspection position and a treatment position, accurately and quickly, thus achieving significant improvement in the efficiency of the inspection and treatment in the medical settings. For example, compared to the configuration in which a table with a caster is used to move the patient as a target, the tables 1008 and 1108 can be moved more smoothly without shaking the patient too much, and may be prevented from being tangled with a lot of cords of medical equipment and the tubes of medical instruments which run on the floor of the medical room, and may be prevented from being wobbled by stepping over the cords and tubes. Thus, safety and transfer efficiency can be improved.

Examples of the target positions of the robotic bed are the same as, or similar to, those described in the first example configuration, and description thereof will be omitted here.

According to the present example configuration, the robot arm can be completely hidden under the table. However, in some cases, such as when the table has a shorter length and when the base is more laterally placed to ensure a larger space under the table, part of the robot arm may not be hidden under the table, when viewed from vertically above, on any one of the four sides of the table in the longitudinal direction and the width direction. In terms of space saving, similarly to the first example configuration, the amount of protrusion of the robot arm is preferably less than one fourth (i.e., ¼) of the longitudinal dimension of the table.

The movements of the table supported by the robot arm of the present example configuration between the plurality of positions will be described with reference to FIGS. 12 to 14 by taking, as an example, the robot arm 1001 having 6 degrees of freedom illustrated in FIG. 10.

Figure 12:
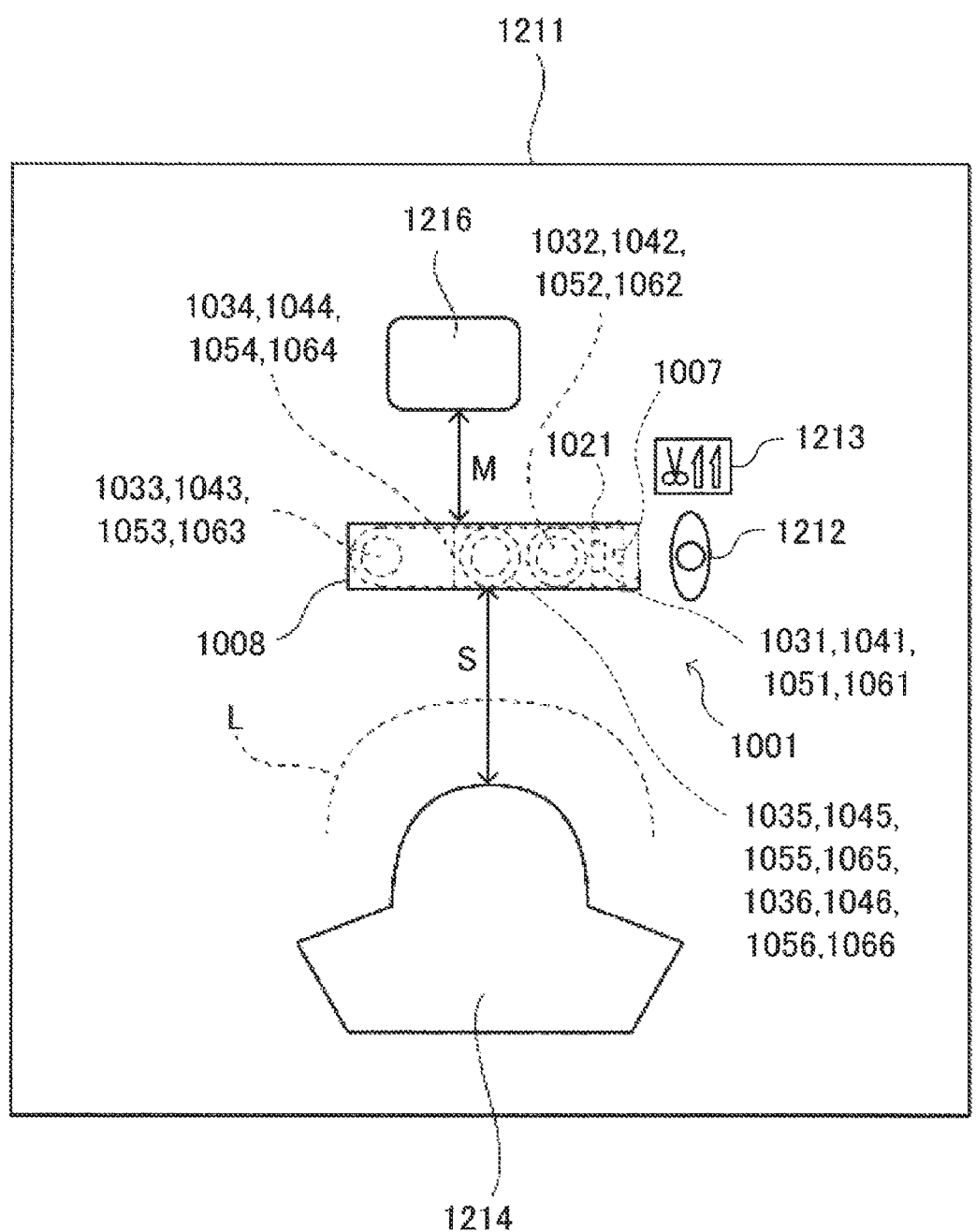
FIG. 12 is a diagram illustrating a plan view of a medical room where the robotic bed according to the second example configuration is placed, and shows a state in which the table is located at a first position.

FIG. 12 illustrates a state in which the table 1008 is located at the placement position (i.e., the first position) in the process of moving a subject, who is a placed target, from the placement position to the inspection position (i.e., a second position). FIG. 13 illustrates a state in which the second movable element 1023 and the third movable element 1024 are moved by the control of the controller 1007 as the arrows indicate, and the table 1008 is rotated about the sixth axis as the arrow indicates (in some cases, the first movable element 1022, too, is moved in the vertical direction to have its height adjusted, and the table 1008 is rotated about the fourth axis and/or the fifth axis to have its tilt with respect to the longitudinal direction and/or the width direction of the table finely adjusted), causing the head of the subject to move toward the inspection device 1214 from an oblique angle. FIG. 14 illustrates a state in which the table 1008 is inserted in the inspection device 1214, and the subject has arrived at the inspection position (i.e., the second position). Note that the position (i.e., the first position) of the table 1008 illustrated in FIG. 12 can also be the treatment position. From the inspection position (i.e., the second position) illustrated in FIG. 14, the respective movable elements move in reverse direction until the table 1008 returns to the position (i.e., the first position) illustrated in FIG. 12, where a doctor 1212 can give a treatment based on the result of the inspection that has just been conducted.

In the case of the robot arm 1101 illustrated in FIG. 11, the second and third joints move like a scalar to enable the table 1108 to move back and forth between the first and second positions.

Note that the head of the subject may be placed opposite in the longitudinal direction of the table 1008, 1108. In that case, the table 1008, 1108 moves to the inspection device 1214, while rotating in the opposite direction to the direction in which the table illustrated in FIG. 13 rotates. Once the base 1021, 1121 is housed in this manner under the table 1008, 1108, the target may be placed in either direction. If the position of the table 1008, 1108 illustrated in FIG. 12 is the treatment position, a surgeon 1212 may perform surgery from either side of the table 1008, 1108, and the surgeon 1212, and assistants, as well, may surround the table during the surgery, which is advantageous. Since the base 1021, 1121 does not constitute an obstacle, the doctor 1212 is able to give treatment while seated.

Third Example Configuration

Figure 15:
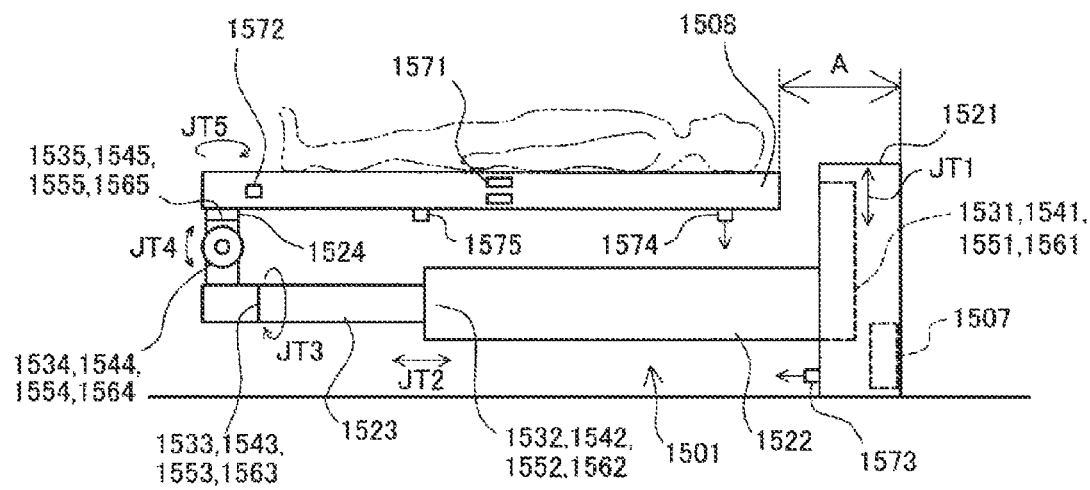
FIG. 15 is a diagram illustrating a side view of a robotic bed according to a third example configuration.

FIG. 15 is a diagram illustrating a side view of a robotic bed according to a third example configuration of one or more embodiments. A robot arm 1501 used for the robotic bed has multiple degrees of freedom (i.e., three or more degrees of freedom), and has a distal end supporting a table 1508 on which a target is placed. The table 1508 and the robot arm 1501 form the robotic bed.

As illustrated in FIG. 15, the robot arm 1501 includes a base 1521, a plurality of movable elements (first to third movable elements 1522 to 1524 in the present example configuration), and a plurality of joints (first to fifth joints 1531 to 1535 in the present example configuration).

The base 1521 and one end portion of the first movable element 1522 are coupled together by the first joint 1531 traveling vertically straight, which enables the first movable element 1522 to move in a first axial direction (i.e., in a vertical direction). The other end portion of the first movable element 1522 has an opening into which one end of the second movable element 1523 is fitted. The first movable element 1522 and the second movable element 1523 are coupled together by a joint traveling horizontally straight. This configuration allows the second movable element 1523 to move straight in the second axis direction (i.e., the horizontal direction). Third to fifth joints 1533 to 1535 between the second movable element 1523 and the third movable element 1524 are rotating joints which rotate about third to fifth axes, respectively. The third axis corresponds to a direction in which the second movable element 1523 extends. The fourth axis corresponds to a direction orthogonal to the third axis about which the third joint 1533 rotates. The fifth axis corresponds to a direction orthogonal to the fourth axis about which the fourth joint 1534 rotates.

Each of the first movable element 1522 and the second movable element 1523 is a rod-like member extending in a particular direction, with its length appropriately designed according to a required range of movement of the robot arm 1501. The first movable element 1522 moves up and down, while staying parallel to the horizontal plane. The second movable element 1523 moves in the second axis direction (i.e., in the lateral direction indicated by JT2 in FIG. 15), while staying parallel to the first movable element 1522. In this configuration, the first and second movable elements overlap each other in the vertical direction (that is, the first and second movable elements share the same horizontal axis). Reduction in height of the table 1508 can thus be achieved. This configuration allows the target to be easily placed on the table 1508, which is advantageous when the table is used in a treatment room or an inspection room.

Preferably, in this example configuration, the width of the table 1508 is greater than the width of each of the movable elements of the robot arm 1501. For example, it is preferable that in a state in which particular directions (i.e., the longitudinal directions) of the table 1508, the first movable element 1522, and the second movable element 1523 coincide with one another when viewed from vertically above, the first movable element 1522 and the second movable element 1523 be hidden under the table 1508 in the direction (i.e., the width direction of the table 1508) orthogonal to the particular direction (i.e., the longitudinal directions of the first movable element 1522, the second movable element 1523, and the table 1508) at portions where the table 1508 overlaps with the first movable element 1522 and the second movable element 1523 in the particular direction (i.e., the longitudinal direction) when viewed from vertically above. In this configuration, portions of the robot arm 1501 (that is, in the example of FIG. 15, all of the first movable element 1522 other than the one end portion thereof, and all of the second movable element 1523 and the third movable element 1524) which overlap with one another in the longitudinal direction of the table 1508 are housed under the table 1508 at least in the width direction of the table 1508 (i.e., the direction orthogonal to the particular direction in which the table 1508 extends) (see, e.g., FIG. 17).

Further, in the present example configuration, the base 1521 is higher than the lower surface of the table 1508 in order to provide a greater range of adjustment for the vertical movement of the table 1508, even in a state in which the distal end of the robot arm 1501 is located at the lowermost position of its motion range and the table 1508 takes a position parallel to the horizontal plane. These configurations allow the movable elements of the robot arm 1501 to be located and housed under the table 1508, and hence allow effective use of a limited space in the medical settings while ensuring a broad range for the vertical movement of the table 1508.

In the example illustrated in FIG. 15, the first movable element 1522 is directly coupled to the base 1521. However, the movable element may also be indirectly coupled to the base via another horizontally-rotating joint or a vertically-rotating joint. In this case, as well, the advantages of ensuring a larger space, downsizing the robot arm, and keeping the table at a lower height can be achieved, as long as the above-described positional relationship is maintained (that is, the plurality of movable elements are located on the same horizontal plane, i.e., overlap with one another when viewed from the horizontal direction) and the plurality of movable elements are housed under the table 1508.

Further, similarly to the first example configuration, for the purpose of space saving and in consideration of the size of the robot arm 1501 enough to maintain the strength for supporting the table 1508, the dimension A (see FIG. 15) in the longitudinal direction of the table 1508 where the robot arm 1501 is not hidden under the table 1508 is preferably one fourth (i.e., ¼) or less of the longitudinal dimension of the table 1508.

The third movable element 1524 is provided at the distal end of the robot arm 1501. In the present example configuration, the distal end of the robot arm 1501 is fixed on a lower surface of the one end portion of the table 1508 extending in the particular direction. This configuration allows the robot arm 1501 to move such that the other end of the table 1508 is positioned as far away from the base 1521 as possible. Supporting the table 1508 at its one end portion increases the movable range of the table 1508. However, the table 1508 may be supported at its middle portion if a priority is placed on the supporting strength.

The definitions of the "one end portion," "other end portion," "end portion" and "middle portion" as adopted in the above description are the same as, or similar to, those adopted in the first and second example configurations.

The robot arm 1501 includes: a plurality of actuators (first to fifth actuators 1541 to 1545 in the present example configuration) associated with the first to fifth joints 1531 to 1535 to move or rotate the first to third movable elements 1522 to 1524; a plurality of position detectors (first to fifth position detectors 1551 to 1555 in the present example configuration) built in the respective joints to detect the positions of the respective movable elements; and a controller 1507 (see FIG. 15) which controls the actuation of the respective actuators. The controller 1507 is provided in the base 1521, but may also be an independent external device, for example.

The first to fifth actuators 1541 to 1545 are servomotors, for example. Similarly to the first and second example configurations, encoders, resolvers, and potentiometers may be used as the position detectors.

Preferably, the robot arm 1501 further includes first to fifth electromagnetic brakes 1561 to 1565 associated with the first to fifth joints 1531 to 1535. If the robot arm 1501 does not include any electromagnetic brakes, the posture of the robot arm 1501 is maintained by actuating the plurality of actuators 1541 to 1545. If the robot arm 1501 includes the electromagnetic brakes, the posture of the robot arm 1501 may be maintained by turning the electromagnetic brakes on even if some of the actuators are turned off.

In the case where the electromagnetic brakes are provided, each of the first to fifth electromagnetic brakes 1561 to 1565 is configured to turn its brake function on when no drive current is supplied to the associated one of the actuators, and to turn its brake function off when a drive current is supplied to the actuator.

Similarly to the first and second example configurations, in many cases, a motor functioning as the actuator, an encoder functioning as the position detector, and the brake are integrated together as a unit as illustrated in FIG. 3. Further, each of the first to fifth actuators 1541 to 1545 is provided with a deceleration mechanism, a coupling, etc., for power transmission.

The robotic bed having the above configuration makes it possible to move the table 1508, on which a target has been placed, to a target position, such as an inspection position and a treatment position, accurately and quickly, thus achieving significant improvement in the efficiency of the inspection and treatment in the medical settings. For example, compared to the configuration in which a table with a caster is used to move the patient, the table 1508 can be moved more smoothly without shaking the patient too much, and may be prevented from being tangled with a lot of cords of medical equipment and the tubes of medical instruments which run on the floor of the medical room, and may be prevented from being wobbled by stepping over the cords and tubes. Thus, safety and transfer efficiency can be improved.

Examples of the target positions of the robotic bed are the same as, or similar to, those described in the first and second example configurations, and description thereof will be omitted here.

In the first and second example configurations, the robot arm is configured such that the movable elements are coupled together at their end portions by a horizontally-rotating joint. Thus, the movable elements overlap each other in the vertical direction. On the other hand, a joint traveling horizontally straight is employed in the present example configuration. Thus, the overlapping in the vertical direction does not occur, which is more advantageous in placing the table 1508 at a lower position.

The movements of the table 1508 supported by the robot arm 1501 of the present example configuration between the plurality of positions will be described with reference to FIGS. 17 to 19.

Figure 17:
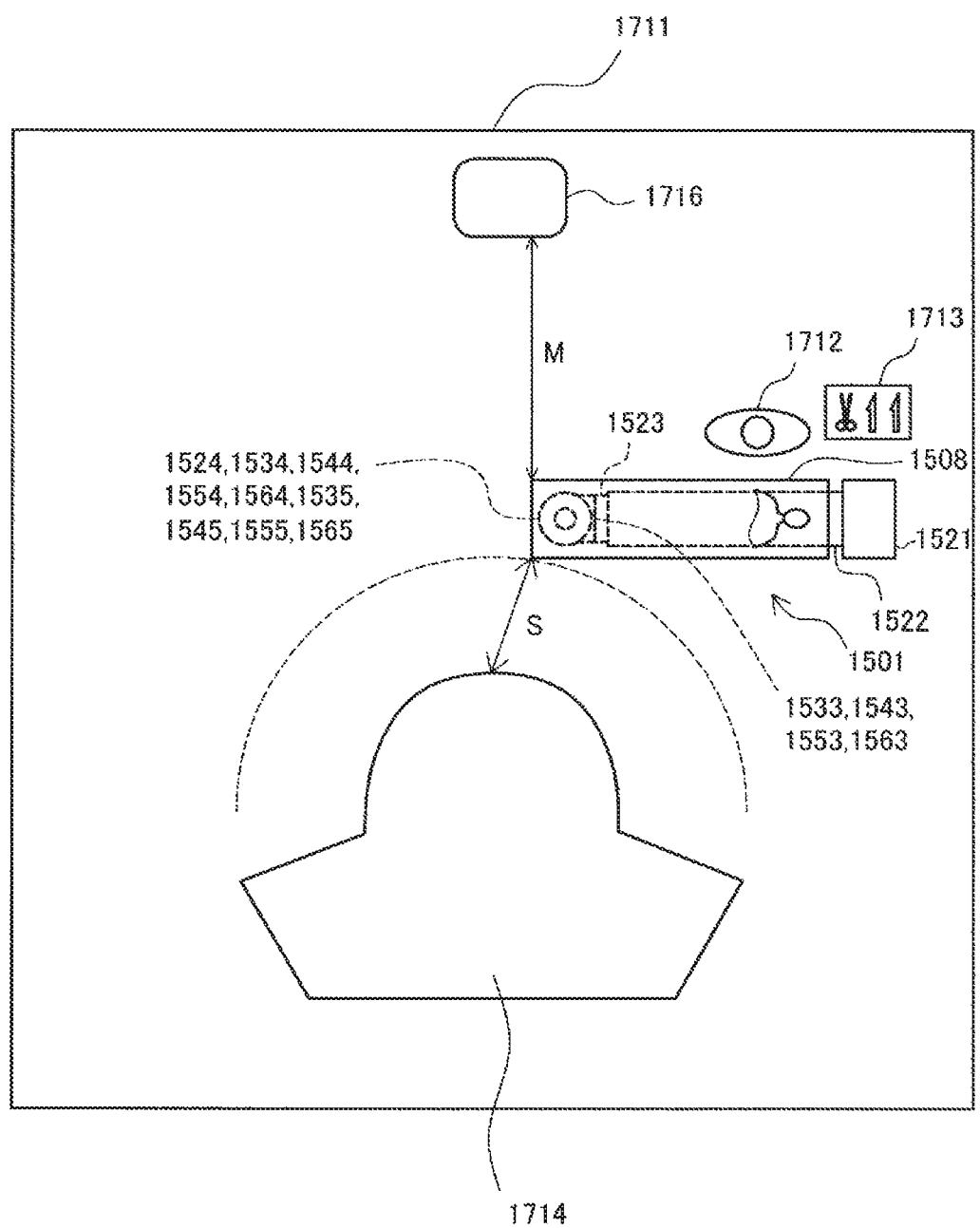
FIG. 17 is a diagram illustrating a plan view of a medical room where the robotic bed according to the third example configuration is placed, and shows a state in which the table is located at a first position.

FIG. 17 illustrates a state in which the table 1508 is located at the placement position (i.e., a first position) in the process of moving a subject, who is a placed target, from the placement position to the inspection position. FIG. 18 illustrates a state in which the second movable element 1523 and the table 1508 are moved by the control of the controller 1507 as the arrows indicate (in some cases, the first movable element 1522, too, is moved in the vertical direction to have its height adjusted, and the table 1508 is rotated about the third axis and/or the fourth axis to have its tilt with respect to the longitudinal direction and/or the width direction of the table finely adjusted), causing the head of the subject to move toward the inspection device 1714 from an oblique angle. FIG. 19 illustrates a state in which the table 1508 is inserted in the inspection device 1714, and the subject has arrived at the inspection position (i.e., a second position). Note that the position (i.e., the first position) of the table 1508 illustrated in FIG. 17 can also be the treatment position. From the inspection position illustrated in FIG. 19, the respective movable elements move in reverse direction until the table 1508 returns to the position illustrated in FIG. 17, where a doctor 1712 can give a treatment based on the result of the inspection that has just been conducted.

The robot arm 1501 illustrated in FIG. 15 has 5 degrees of freedom. However, the degrees of freedom of the robot arm of one or more embodiments do not have to be 5, and may be 4 or less or 6 or more. Nevertheless, it is preferable that the degrees of freedom of the robot arm be 3 or more so that the table 1508 can move at least in a straight manner in the room.

Figure 16:
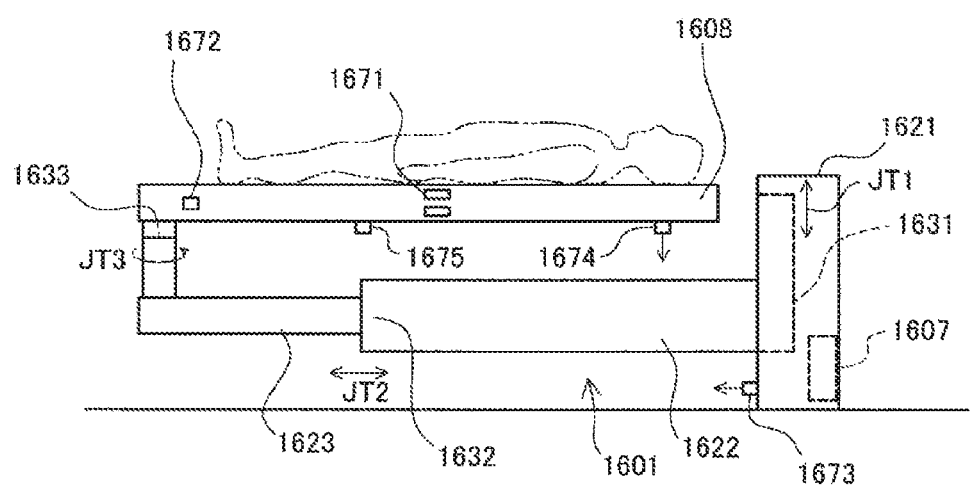
FIG. 16 is a diagram illustrating a side view of a robotic bed configured to have a minimum degree of freedom according to the third example configuration.

FIG. 16 illustrates an example robotic bed having 3 degrees of freedom. In FIG. 16, the robot arm 1601 is comprised of a base 1621 and two movable elements 1622 and 1623. The base 1621 and one end portion of the first movable element 1622 are coupled together by a first joint 1631 traveling vertically straight, which enables the first movable element 1622 to move in a first axial direction (i.e., in a vertical direction). The other end portion of the first movable element 1622 has an opening into which one end of the second movable element 1623 is fitted. The first movable element 1622 and the second movable element 1623 are coupled together by a joint traveling horizontally straight. This configuration allows the second movable element 1623 to move in the second axis direction (i.e., the horizontal direction). The other end of the second movable element 1623 serves as the distal end of the robot arm 1601, and is coupled to one end portion of the table 1608 by a third joint 1633, which is a horizontally-rotating joint.

Figure 18:
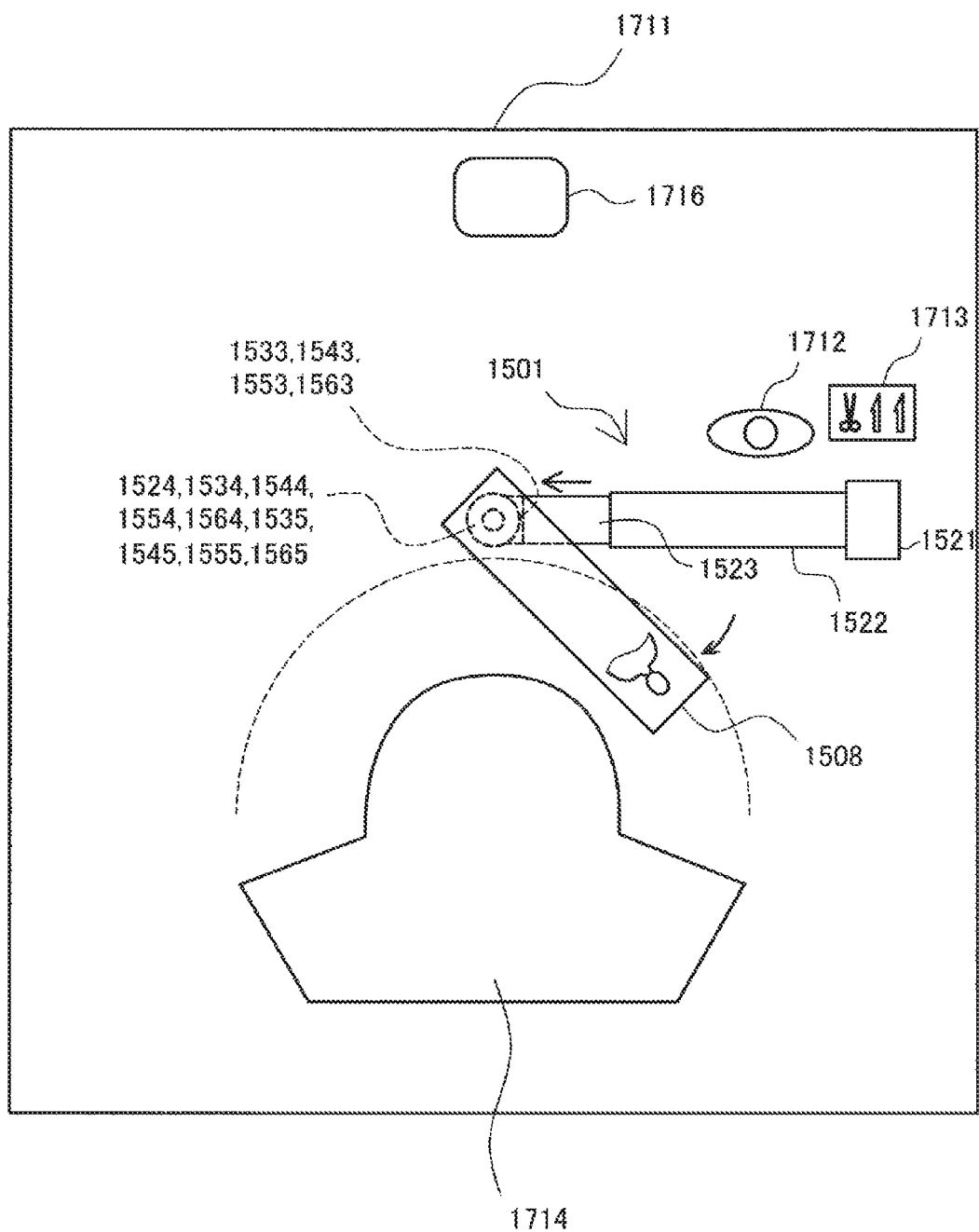
FIG. 18 is a diagram illustrating a plan view of the medical room where the robotic bed according to third example configuration is placed, and shows the table in the middle of being transferred from the first position to a second position.
Figure 19:
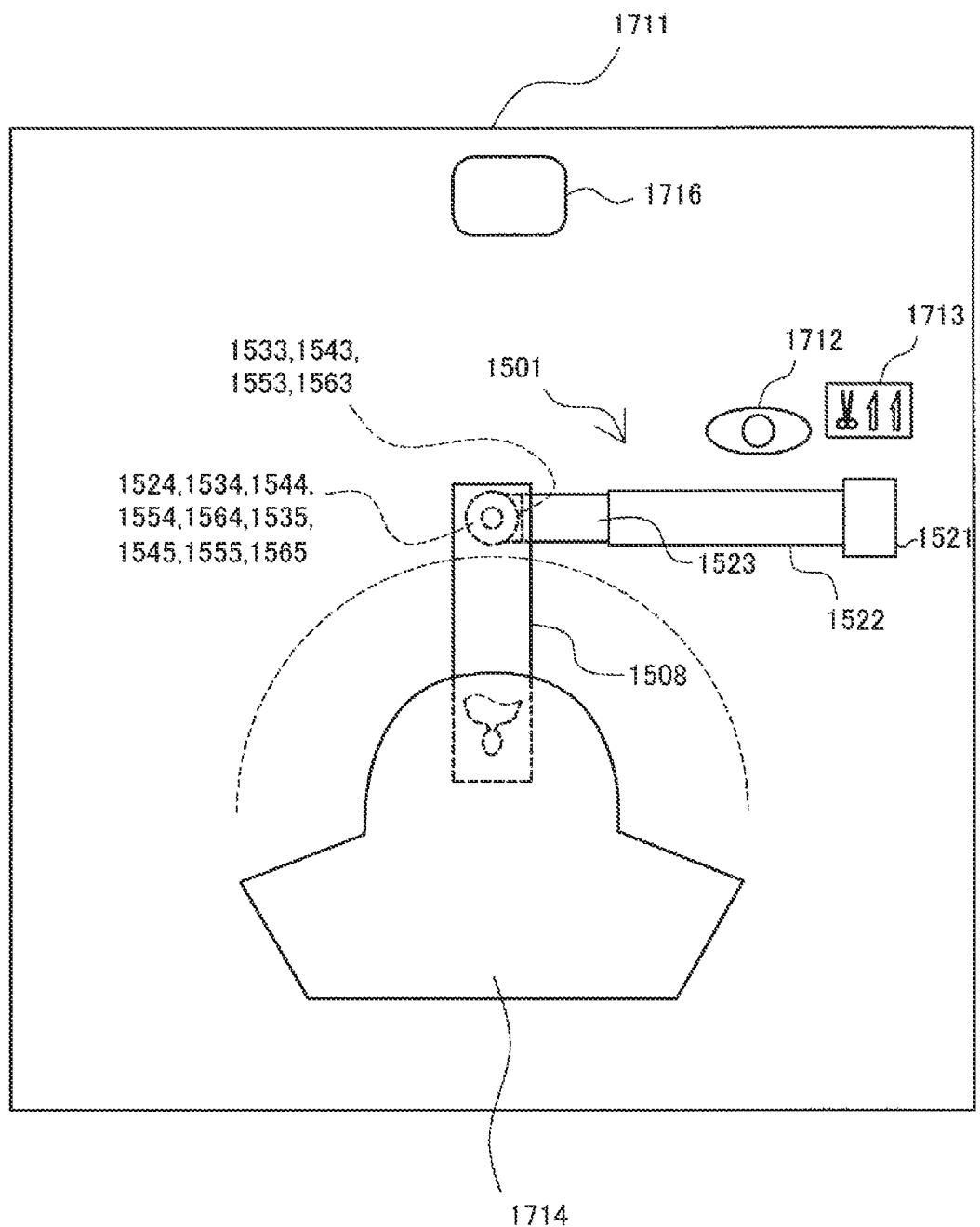
FIG. 19 is a diagram illustrating a plan view of the medical room where the robotic bed according to the third example configuration is placed, and shows a state in which the table is located at the second position.

According to the robotic bed illustrated in FIG. 16, although the adjustment of tilt of the table 1608 about the axes in the longitudinal direction and width direction of the table 1608 is limited, the table 1608 can move as illustrated in FIGS. 17 to 19 when viewed from vertically above.

Using a joint which travels horizontally straight as in the present example configuration provides an advantage of preventing the movable elements from protruding from the table in a movement causing the table to move simply straight, unlike the case of the scalar type in the first and second example configurations. For example, a ball screw or a rack and pinion mechanism may be employed as a configuration of the joint traveling straight.

Fourth Example Configuration

Figure 20:
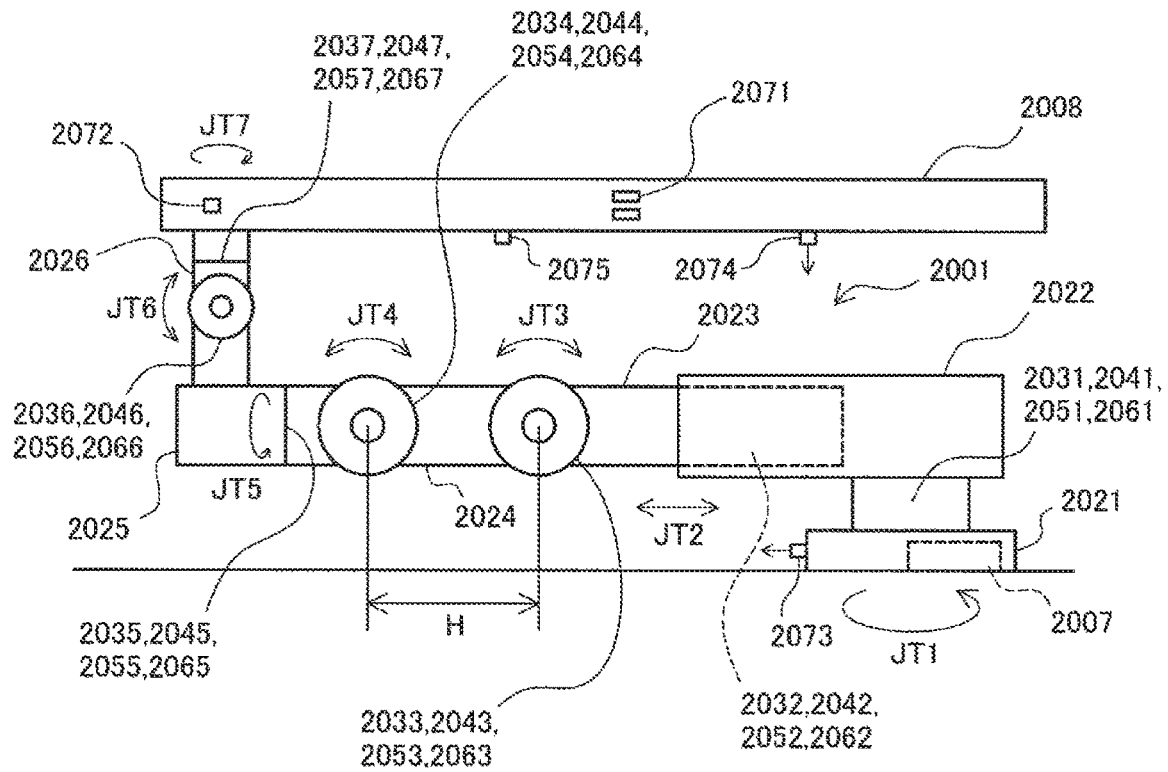
FIG. 20 is a diagram illustrating a side view of a robotic bed according to a fourth example configuration.

FIG. 20 is a diagram illustrating a side view of a robotic bed according to a fourth example configuration of one or more embodiments. A robot arm 2001 used for the robotic bed has multiple degrees of freedom (i.e., three or more degrees of freedom), and has a distal end supporting a table 2008 on which a target is placed. The table 2008 and the robot arm 2001 form the robotic bed.

As illustrated in FIG. 20, the robot arm 2001 includes a base 2021, a plurality of movable elements (first to fourth movable elements 2022 to 2026 in the present example configuration), and a plurality of joints (first to seventh joints 2031 to 2037 in the present example configuration).

The base 2021 and one end portion of the first movable element 2022 are coupled together by a first joint 2031 (i.e., a horizontally-rotating joint, which enables the first movable element 2022 to move in a first axial direction (i.e., a vertical direction). The other end portion of the first movable element 2022 has an opening at least on the other end portion side in a particular direction. One end of the second movable element 2023 is fitted in the opening. The first movable element 2022 and the second movable element 2023 are coupled together by a joint traveling straight. This configuration allows the second movable element 2023 to move in a second axis direction (i.e., the horizontal direction). The other end portion of the second movable element 2023 and one end portion of the third movable element 2024 are coupled together by a vertically-rotating joint, which enables the third movable element 2024 to rotate about a third axis orthogonal to both of the longitudinal direction (i.e., the extending direction of the third movable element 2024) and the vertical direction. The other end portion of the third movable element 2024 and one end portion of the fourth movable element 2025 are coupled together by a vertically-rotating joint, which enables the fourth movable element 2025 to rotate about a fourth axis orthogonal to both of the longitudinal direction (i.e., the extending direction of the fourth movable element 2025) and the vertical direction and parallel to the third axis. The rotation of the third axis and the rotation of the fourth axis can be controlled independently. For example, the third and fourth movable elements 2024 and 2025 may be configured such that when the third movable element 2024 makes a 15 degree clockwise rotation about the third axis, the fourth movable element 2025 makes a 15 degree counterclockwise rotation about the fourth axis in synchronization (see FIG. 21). As a result, the fourth movable element 2025 is movable up and down, with the entire fourth movable element 2025 staying parallel to the horizontal plane. The fifth to seventh joints 2035 to 2037 between the fourth movable element 2025 and the fifth movable element 2026 are rotating joints which rotate about fifth to seventh axes, respectively. The fifth axis corresponds to a direction in which the fourth movable element 2024 extends. The sixth axis corresponds to a direction orthogonal to the fifth axis about which the fifth joint 2035 rotates. The seventh axis corresponds to a direction orthogonal to the sixth axis about which the sixth joint 2036 rotates.

Each of the first to fourth movable elements 2022 to 2025 is a rod-like member extending in the particular direction, with its length appropriately designed according to a required range of movement of the robot arm 2001 and a range of movement of the table 2008 in the vertical direction. In the present example configuration, the up and down movement of the table 2008 in the vertical direction is realized by two rotating joints (i.e., the third vertically-rotating joint 2033 and the fourth vertically-rotating joint 2034) capable of being positioned on the same horizontal plane (i.e., at the same height). Thus, the base is not as high as the bases in the first to third example configurations which need to be high enough. That is, the traveling range of the table 2008 in the vertical direction is adjustable not based on the height of the base in the vertical direction, but based on the length of the third movable element 2024. In this manner, the two movable elements (2023 and 2024, or 2024 and 2025), coupled together by the vertically-rotating joint (2033 and 2034) to move the table 2008 in the vertical direction, overlap with each other when viewed from the horizontal direction, while taking a particular position (e.g., while the robot arm 2001 takes a position where the table 2008 is located at the lowermost position in the range of movement in the vertical direction). Thus, the table can be further lowered in height, making it possible to ensure treatment at a lower position and placement of a target at a lower position. The configuration of the base 2021 capable of hiding under the table 2008 is advantageous in introducing the robot arm in the medical settings where only a limited space is available, or in ensuring a larger space for treatment and surgery. The range of adjustment in the height of the table 2008 depends on the length H of the third movable element. The height H is therefore determined in consideration of the range of movement of the table in the vertical direction.

The two movable elements do not have to be coupled together by the vertically-rotating joint at their end portions as illustrated in FIG. 20. For example, the two movable elements may be coupled together at their side surfaces by the vertically-rotating joint. The configuration in which the movable elements coupled together by a vertically-rotating joint overlap with each other when viewed from the horizontal direction does not necessarily require the linear motion joint to be used together. For example, such a configuration may also be used as a substitute for the vertically traveling joint used in the first and second example configurations, and is not limited to the case described in the present example configuration. The configuration is an independent feature for achieving a space saving robotic bed.

In the first and second example configurations, the robot arm is configured such that the movable elements are coupled together at their end portions by a horizontally-rotating joint. Thus, the movable elements overlap each other in the vertical direction. On the other hand, a joint traveling horizontally straight is employed in the present example configuration. Thus, the overlapping does not occur, which is more advantageous in placing the table 2008 at a lower position.

Further, the robotic bed of the present example configuration is configured to prevent the table 1008 from coming into contact with the robot arm 2001, even when the table 2008 is moved up and down (i.e., in the vertical direction) with the table 2008 maintained parallel to the horizontal plane, or no matter how much (e.g., 360 degrees) the table 2008 is rotated. Thus, in the present example configuration, the table and the robot arm do not come into contact with each other, no matter what posture the robot arm has, or how much the table 2008 is rotated, as long as the table 2008 is maintained parallel to the horizontal plane.

It is preferable that the width of the table 2008 be greater than the width of each of the movable elements of the robot arm 2001 and the width of the base, and therefore that the entire robot arm 2001, including the base 2021, be hidden under the table 2008 when viewed from vertically above. For example, it is preferable that all the movable elements and the base 2021 may be hidden under the table 2008 when the table 2008 is viewed from vertically above, in a state in which the longitudinal direction of the table 2008 and the particular directions of the first and second movable elements 2022 and 2023 are parallel to each other when viewed from vertically above.

Figure 21:
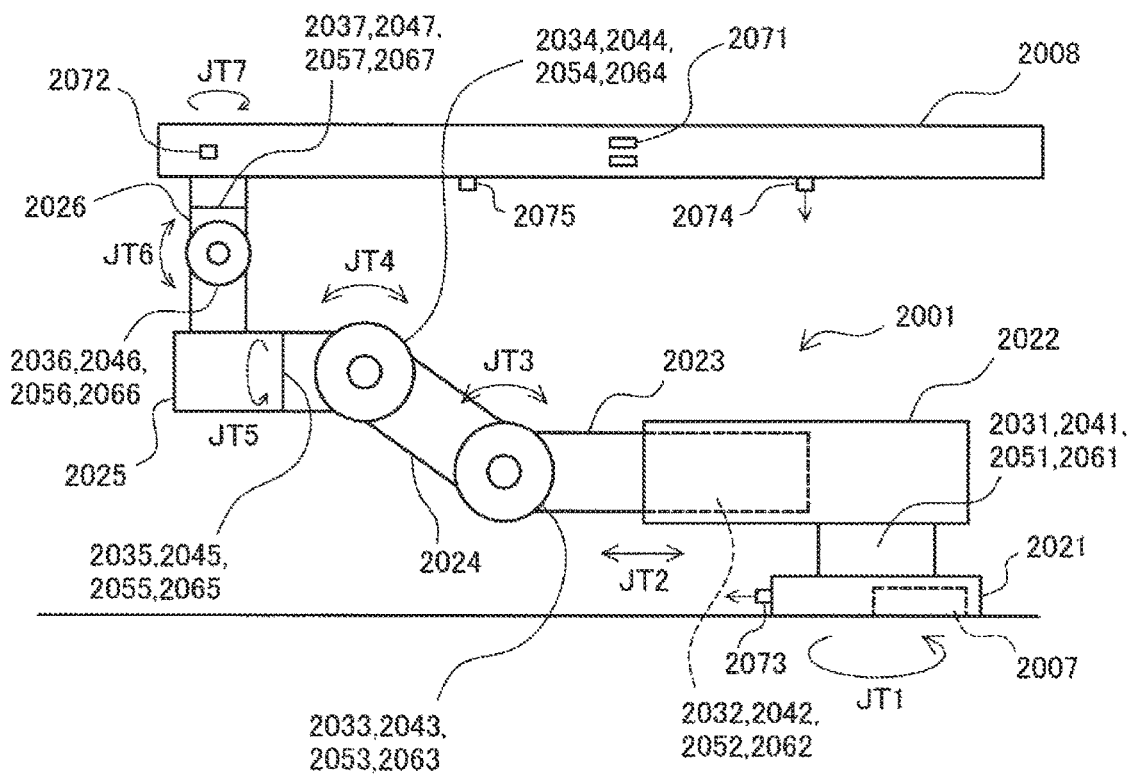
FIG. 21 is a diagram illustrating a side view of the robotic bed according to the fourth example configuration, in which the robotic bed is moved upward.

In the present example configuration, the fifth movable element 2026 is provided at the distal end of the robot arm 2001. In FIGS. 20 and 21, the distal end of the robot arm 2001 is fixed on a lower surface of an end of the table 2008 extending in the particular direction. The range of movement of the table 2008 can thus be increased.

The definitions of the "one end portion," "other end portion," "end portion" and "middle portion" as adopted in the above description are the same as, or similar to, those adopted in the first and second example configurations.

The robot arm 2001 includes: a plurality of actuators (first to seventh actuators 2041 to 2047 in the present example configuration) associated with the first to seventh joints 2031 to 2037 to move or rotate the first to fifth movable elements 2022 to 2026; a plurality of position detectors (first to seventh position detectors 2051 to 2057 in the present example configuration) built in the respective joints to detect the positions of the respective movable elements; and a controller 2007 (see FIG. 20) which controls the actuation of the respective actuators. In the present example configuration, the controller 2007 is provided in the base 2021, but may also be an independent external device, for example.

The first to seventh actuators 2041 to 2047 are servomotors, for example. Similarly to the first to third example configurations, encoders, resolvers or potentiometers may be used as the position detectors.

Preferably, the robot arm 2001 further includes first to seventh electromagnetic brakes 2061 to 2067 associated with the first to sixth joints 2031 to 2037. If the robot arm 2001 does not include any electromagnetic brakes, the posture of the robot arm 2001 is maintained by actuating the plurality of actuators 2041 to 2047. If the robot arm 2001 includes the electromagnetic brakes, the posture of the robot arm 2001 may be maintained by turning the electromagnetic brakes on even if some of the actuators are turned off.

In the case where the electromagnetic brakes are provided, each of the first to seventh electromagnetic brakes 2061 to 2067 is configured to turn its brake function on when no drive current is supplied to the associated one of the actuators, and to turn its brake function off when a drive current is supplied to the actuator.

Similarly to the first to third example configurations, in many cases, a motor functioning as the actuator, an encoder functioning as the position detector, and the brake are integrated together as a unit as illustrated in FIG. 3. Further, each of the first to seventh actuators 2041 to 2047 is provided with a deceleration mechanism, a coupling, etc., for power transmission.

(Variations)

Figure 22:
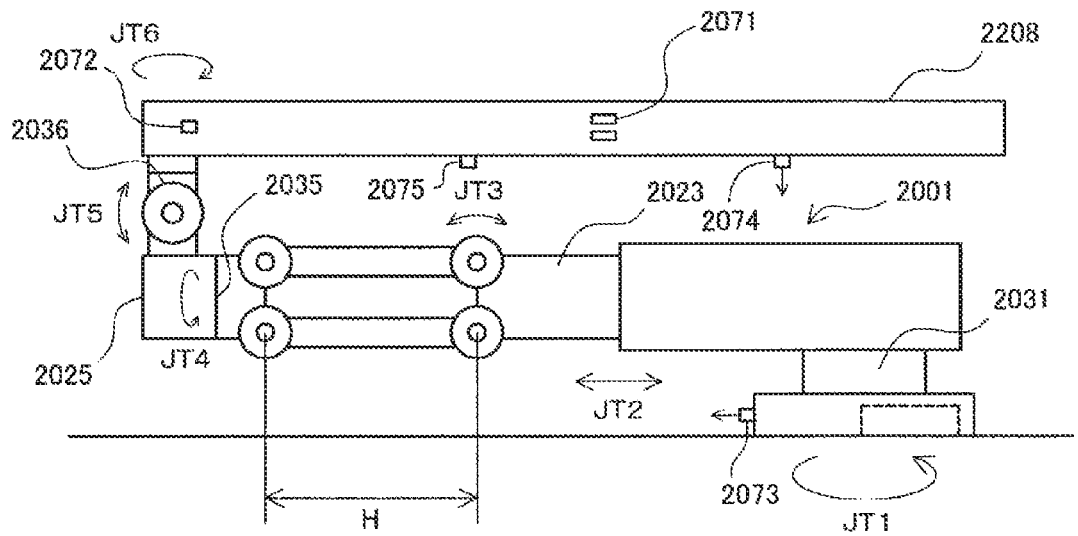
FIG. 22 is a diagram illustrating a side view of a robotic bed according to a variation of the fourth example configuration.

FIG. 22 is a diagram illustrating a side view of a variation according to the fourth example configuration of one or more embodiments. The present variation differs from the fourth example configuration in that the third movable element 2024 and the third and fourth joints are replaced with a parallel link mechanism. That is, the third movable element 2024 is replaced with a movable element comprised of two links (i.e., upper and lower links). One end portion of this movable element is coupled to the second movable element 2023 through an axis parallel to the third axis. The other end portion of this movable element is coupled to the fourth movable element 2025 through an axis parallel to the fourth axis.

The parallel link is provided with an actuator associated with only one of the four rotational shafts which consists of two rotational shafts connected to the second movable element 2023 and two rotational shafts connected to the fourth movable element 2025. In the present variation illustrated in FIG. 22, the actuator (and a position detector and a brake) is provided at the upper rotational shaft of the rotation shafts which are connected to the second movable element 2023.

Figure 23:
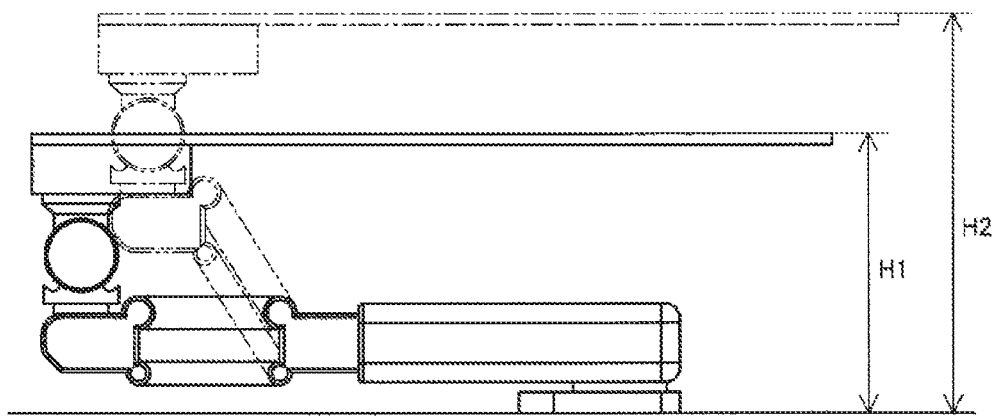
FIG. 23 is a diagram illustrating a side view of the robotic bed according to the variation of the fourth example configuration, and shows the transition state of the robotic bed moved up and down.

The parallel link of the present example configuration serves as an interacting mechanism in which a clockwise rotation of the rotational shaft provided with the actuator causes the other rotational shaft on the same side to rotate clockwise by the same rotational amount, and causes the two rotational shafts on the opposite side to rotate counterclockwise by the same rotational amount. As a result, the fourth movable element 2025 is movable up and down in the vertical direction, while keeping the same state with respect to the horizontal plane. FIG. 23 is a diagram illustrating a side view of the table 2008 moved up and down in the present variation.

With the parallel link mechanism employed in the present variation, it is not the rotational shifts provided at the second movable element 2023, but the rotational shafts provided at the fourth movable element 2025, that receive the weight of the target placed on the table 2008, while the table 2008 moves up and down in the vertical direction. It is therefore possible to reduce torque for moving the table 2008 up and down in the vertical direction. The actuator for driving the parallel link can thus be reduced in size, and hence the robot arm 2001 can be reduced in size. Reduction in size of the robot arm 2001 is advantageous in the configuration in which the entire robot arm 2001 is housed under the table 2008.

Note that one joint can be omitted from the present variation since the number of actuators (and the position detector and the brake) is decreased by one. That is, the fourth joint 2034 in FIG. 20 is omitted, and the fifth to seventh joints in FIG. 20 function as the fourth to sixth joints in FIG. 21.

The robotic bed having the above configuration makes it possible to move the table 2008, on which a target has been placed, to a target position, such as an inspection position and a treatment position, accurately and quickly, thus achieving significant improvement in the efficiency of the inspection and treatment in the medical settings. For example, compared to the configuration in which a table with a caster is used to move the patient as a target, the table 2008 can be moved more smoothly without shaking the patient too much, and may be prevented from being tangled with a lot of cords of medical equipment and the tubes of medical instruments which run on the floor of the medical room, and may be prevented from being wobbled by stepping over the cords and tubes. Thus, safety and transfer efficiency can be improved.

Examples of the target positions of the robotic bed are the same as, or similar to, those described in the first to third example configurations, and description thereof will be omitted here.

Figure 24:
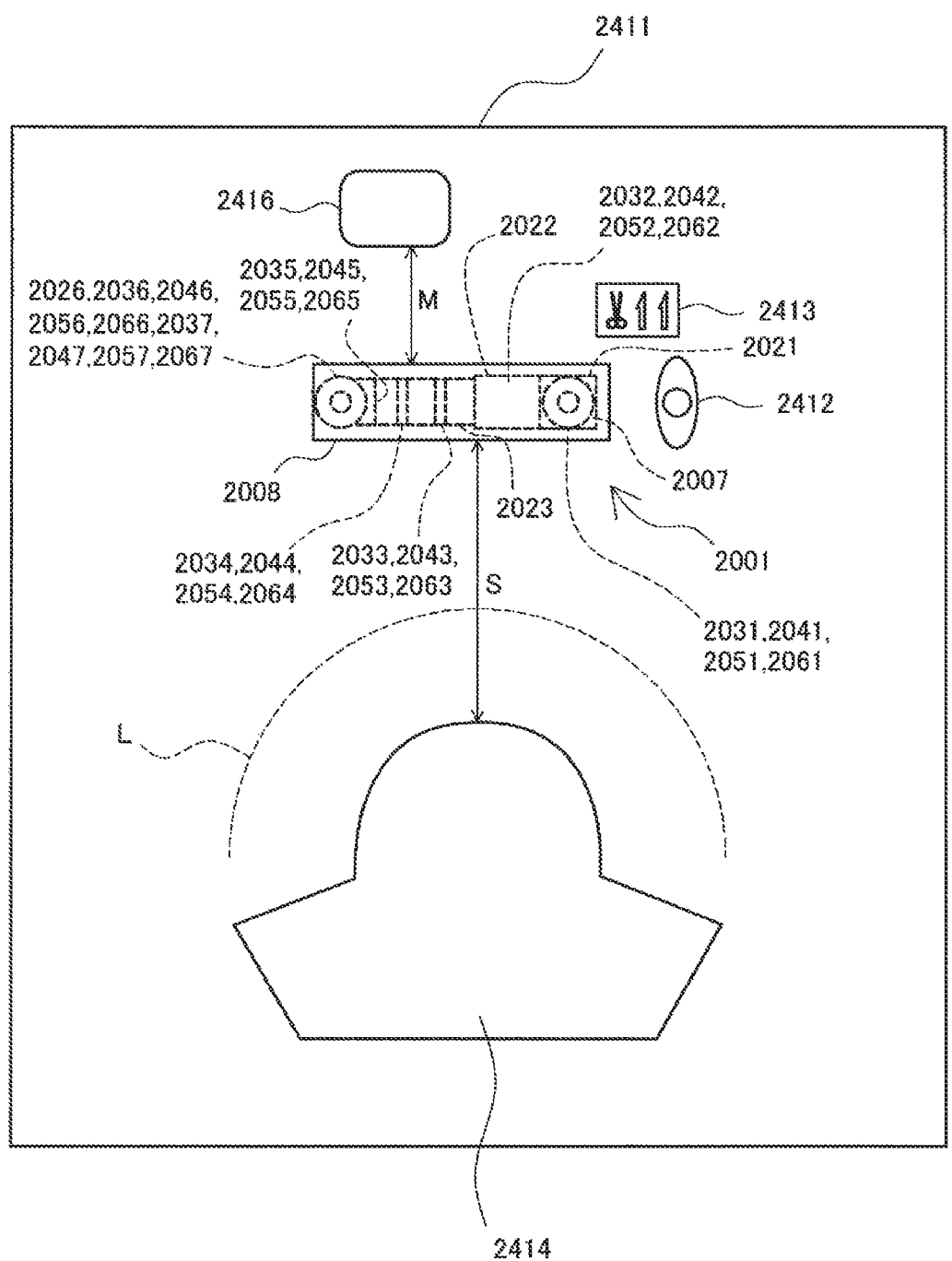
FIG. 24 is a diagram illustrating a plan view of the medical room where the robotic bed according to the fourth example configuration is placed, and shows a state in which the table is located at the first position.
Figure 25:
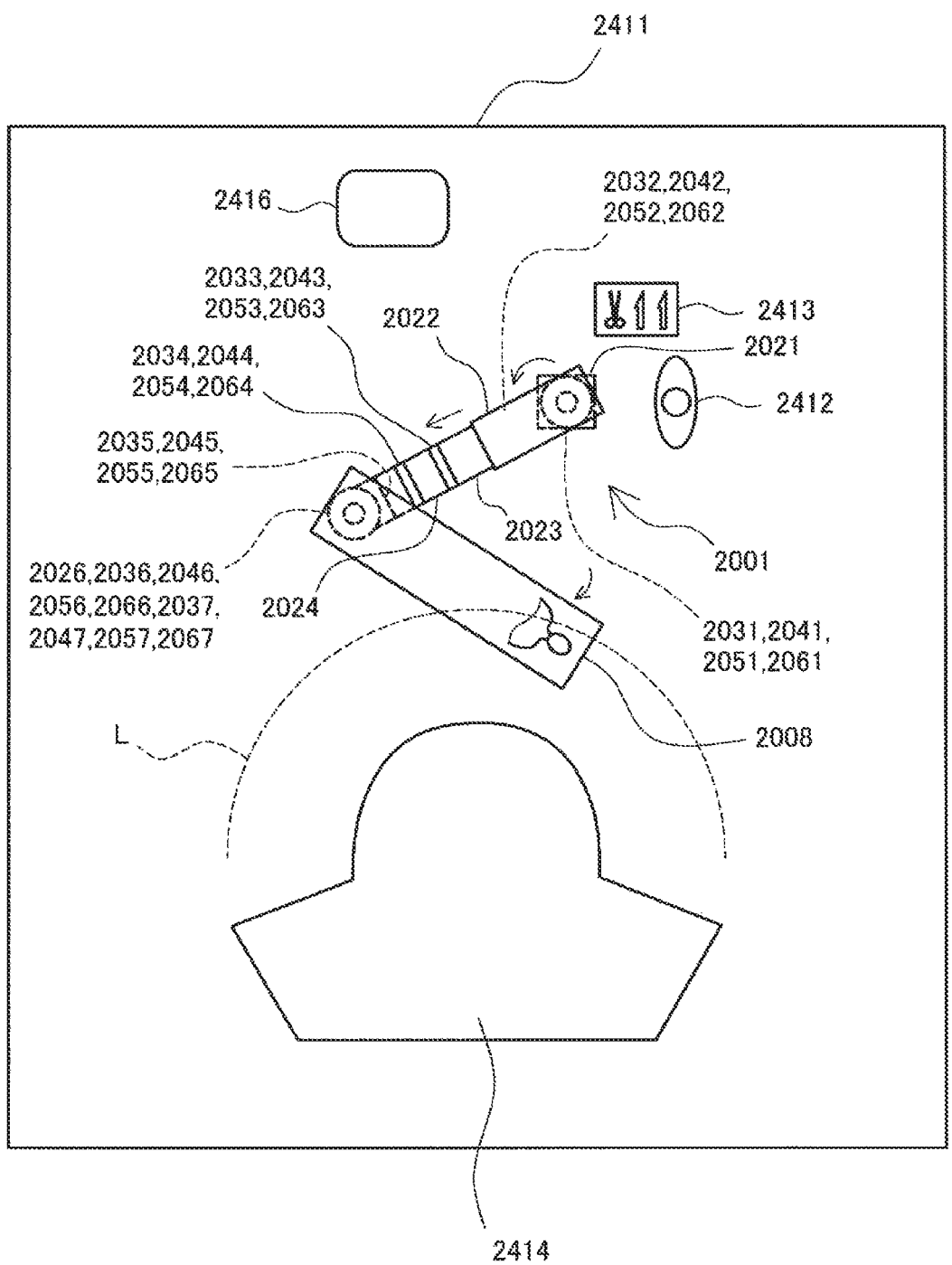
FIG. 25 is a diagram illustrating a plan view of the medical room where the robotic bed according to fourth example configuration is placed, and shows the table in the middle of being transferred from the first position to a second position.
Figure 26:
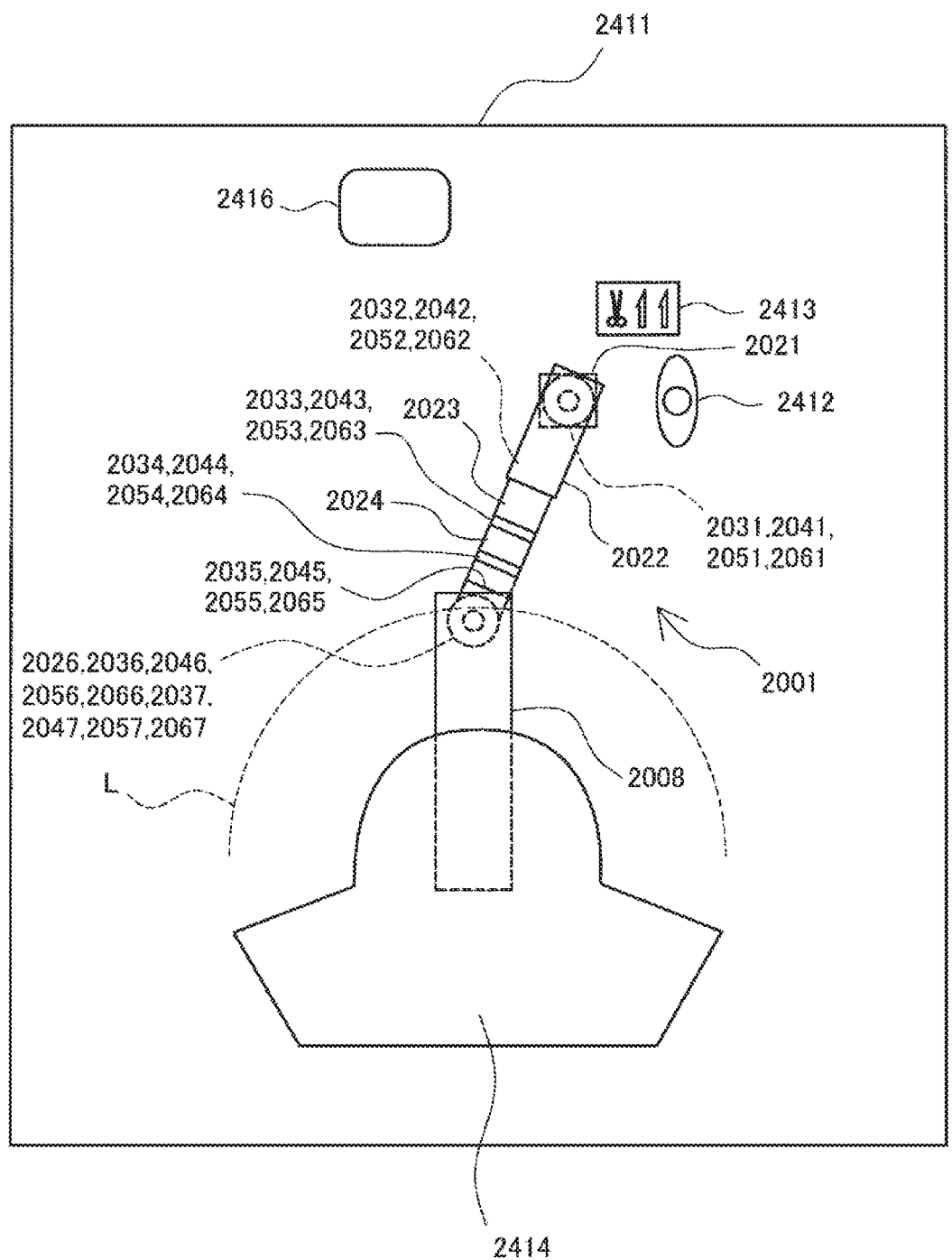
FIG. 26 is a diagram illustrating a plan view of the medical room where the robotic bed according to the fourth example configuration is placed, and shows a state in which the table is located at the second position.

FIG. 24 illustrates a state in which the table 2008 is located at the placement position (i.e., a first position) in the process of moving a subject, who is a placed target, from the placement position (i.e., the first position) to the inspection position (i.e., a second position) using a robotic bed according to the present example configuration. FIG. 25 illustrates a state in which the first movable element 2022, the second movable element 2023, and the table 2008 are moved by the control of the controller 2007 as the arrows indicate (in some cases, the height is adjusted by the third movable element 2024, and the table 2008 is rotated about the fifth axis and/or the sixth axis (the fourth axis and/or the fifth axis in the variation) to have its tilt with respect to the longitudinal direction and/or the width direction of the table finely adjusted), causing the head of the subject to move toward the inspection device 2414 from an oblique angle. FIG. 26 illustrates a state in which the table 2008 is inserted in the inspection device 2414, and the subject has arrived at the inspection position. Note that the position of the table 2008 illustrated in FIG. 24 can also be the treatment position. From the inspection position illustrated in FIG. 26, the respective movable elements move in reverse direction until the table 2008 returns to the position illustrated in FIG. 24, where a doctor 2412 can give a treatment based on the result of the inspection that has just been conducted.

The robot arm 2001 according to the present example configuration illustrated in FIGS. 20 and 22 has 6 or 7 axes, but is not limited thereto. The robot arm 2001 may have 5 or 6 or less axes or may have 7 or 8 or more axes. Nevertheless, it is preferable that the degrees of freedom of the robot arm be 3 or more so that the table 2008 can move at least in a straight manner in the room. For example, omission of the first, fourth, and fifth joints 2031, 2035, and 2036 in FIG. 22 will restrict the movement of the first movable element 2022 in FIG. 25, but it is still possible to make movements similar to those illustrated in FIGS. 17 to 19.

Similarly to the third example configuration, a joint which travels horizontally straight is used in the present example configuration, as well, which provides an advantage of preventing the movable elements from protruding from the table in a movement causing the table to move simply straight, unlike the case of the scalar type in the first and second example configurations. For example, a ball screw or a rack and pinion mechanism may be employed as a configuration of the joint traveling horizontally straight.

According to the present example configuration, as well, the robot arm can be completely hidden under the table. Similarly to the second example configuration, however, in some cases, such as when the table has a shorter length and when the base is more laterally placed to ensure a larger space under the table, part of the robot arm may not be hidden under the table, when viewed from vertically above, on any one of the four sides of the table in the longitudinal direction and the width direction. In terms of space saving, similarly to the first to third example configurations, the amount of protrusion of the robot arm is preferably less than one fourth (i.e., ¼) of the longitudinal dimension of the table.

Fifth Example Configuration

The robotic bed according to the present example configuration is characterized by a slide mechanism provided at the table of the robotic bed in the first to fourth example configurations.

Figure 27A:
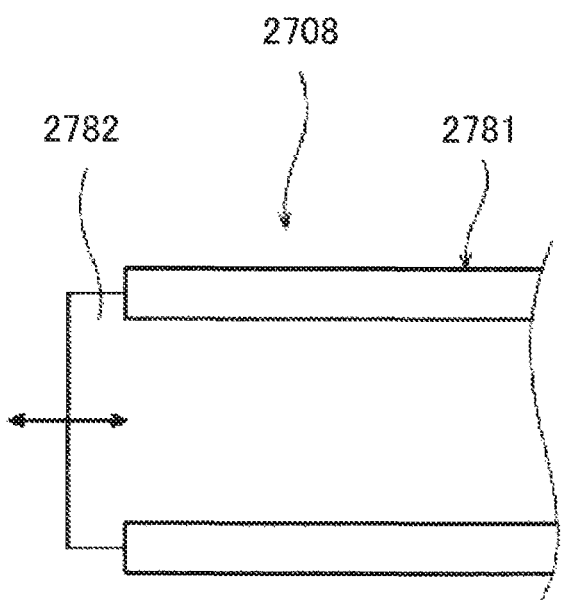
FIGS. 27A and 27B are diagrams illustrating an example slide mechanism used for a robotic bed according to a fifth example configuration.
Figure 27B:
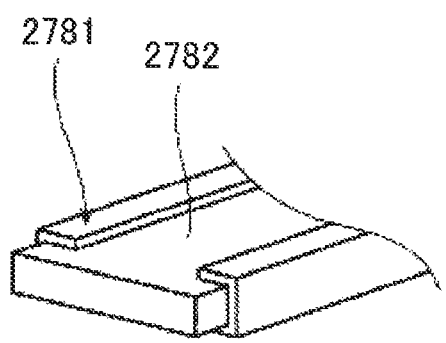

FIGS. 27A and 27B are diagrams illustrating that the table 2708 is comprised of a body 2781 having rails, and a slide plate 2782 fitted in the grooves of the rails. If the table of the robotic bed has this configuration, the slide plate 2282 may be slid by human power to move the placed target farther to an inspection position after the table has been moved to an inspection preparation position by the robot arm, for example.

Figure 28A:
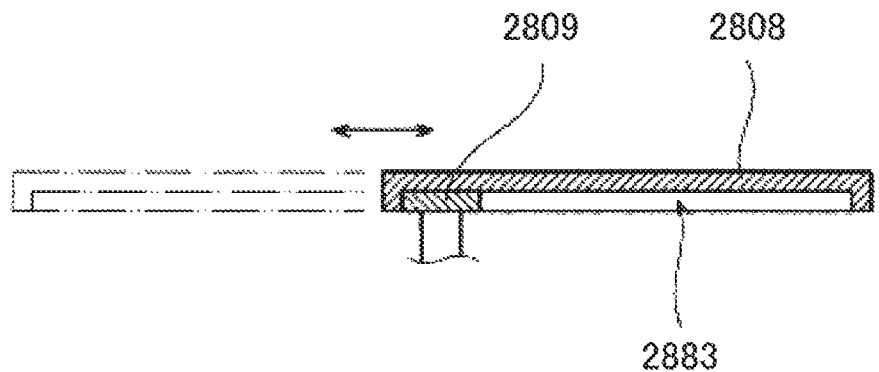
FIGS. 28A and 28B are diagrams illustrating an example slide mechanism which is used for the robotic bed according to the fifth example configuration, and the sliding movement of which can be controlled by the actuation of the actuator.
Figure 28B:
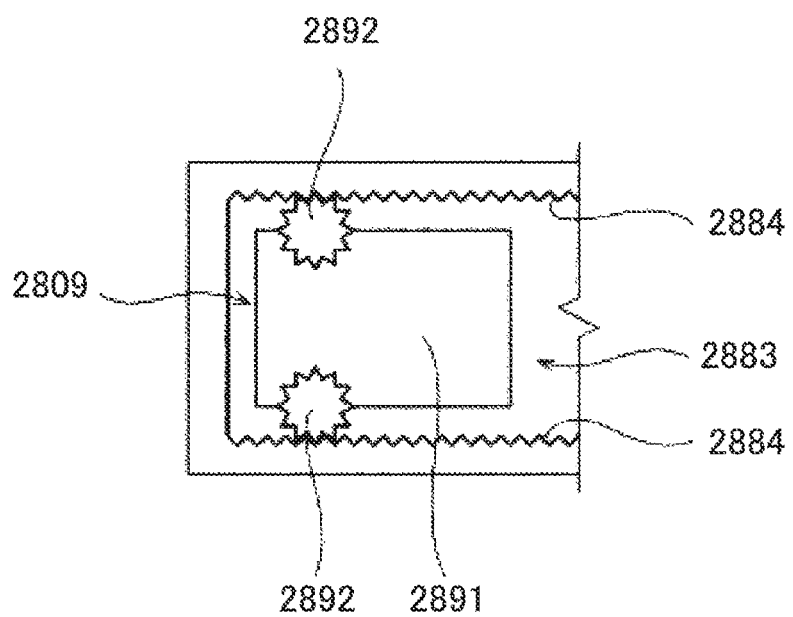

FIGS. 28A and 28B are diagrams illustrating that the table 2808 has, in its lower surface, a groove 2883 in which the slide mechanism 2809 is fitted, and that both sides of the groove 2883 are provided with racks 2884 each having a plurality of teeth. The slide mechanism 2809 includes a body 2891 coupled to a distal end of the robot arm, a pair of pinions 2892 movably supported by the body 2891 and engaged with the racks 2884, and an actuator (not shown) which rotates the pinions 2982. If the table 2808 of the robotic bed has this configuration, the table 2808 may be slid by actuating the actuator to move the placed target farther to an inspection position after the table has been moved to an inspection preparation position by the robot arm, for example. The actuator may be a servo motor, for example.

Note that by providing the slide mechanism, the degree of freedom in each of the example configurations increments by one. In addition, if the slide mechanism is configured to be driven by the actuator, the actuator of the slide mechanism and the plurality of actuators of the robot arm in the respective example configurations may be actuated simultaneously so that the movable elements of the robot arm and the slide mechanism operate simultaneously to transfer the table to the target position efficiently.

Now, example movement of a placed target in a case in which an actuator-driven slide mechanism is adopted as a slide mechanism for the robotic bed of the first example configuration will be described.

Figure 29:
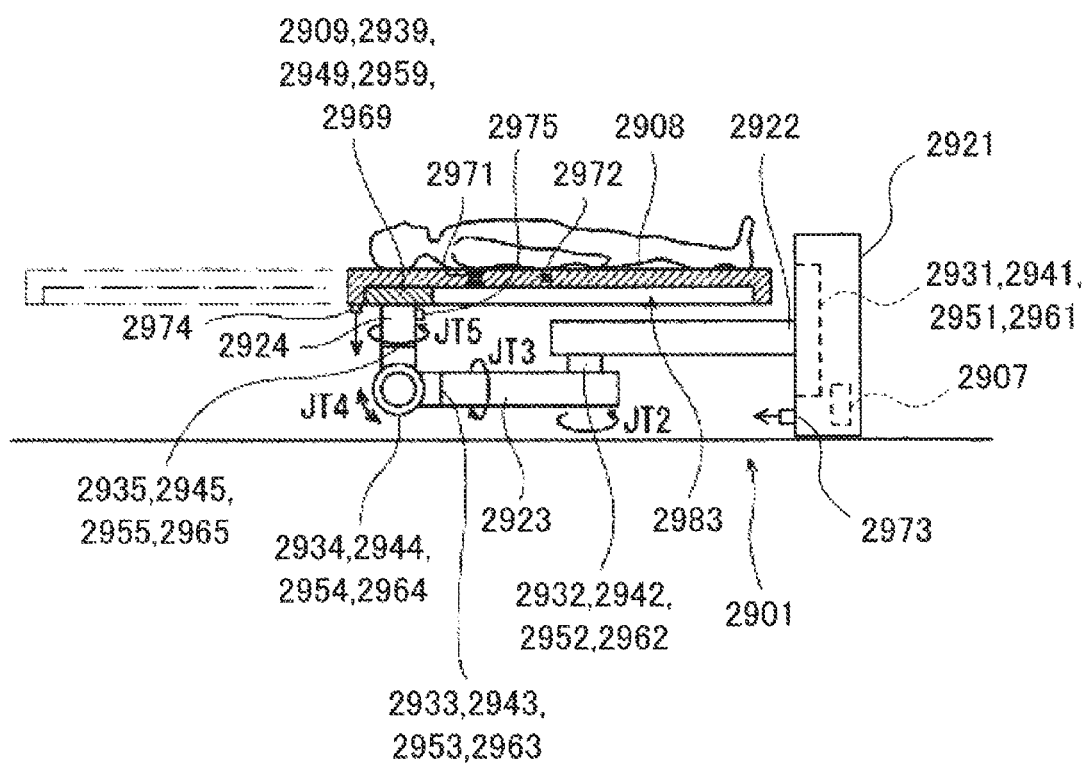
FIG. 29 is a diagram illustrating a side view of the robotic bed according to the fifth example configuration.

FIG. 29 is a diagram illustrating a side view of a robotic bed according to the first example configuration which is provided with a slide mechanism.

A robot arm 2901 used for the robotic bed has multiple degrees of freedom (i.e., three or more degrees of freedom), and has a distal end supporting a table 2908 on which a target is placed. The table 2908 and the robot arm 2901 form the robotic bed.

The robot arm 2901 includes a base 2921, a plurality of movable elements (first to third movable elements 2922 to 2924 in the present example configuration), and a plurality of joints (first to fifth joints 2931 to 2935 in the present example configuration).

The base 2921 and one end portion of the first movable element 2922 are coupled together by the first joint 2931 traveling vertically straight, which enables the first movable element 2922 to move in a first axial direction (i.e., a vertical direction). The other end portion of the first movable element 2922 and one end portion of the second movable element 2923 are coupled together by a horizontally-rotating joint, which enables the second movable element 2923 to rotate about a second axis (i.e., the vertical direction). Third to fifth joints 2933 to 2935 between the second movable element 2923 and the third movable element 2924 are rotating joints which rotate about third to fifth axes, respectively. The third axis corresponds to a direction in which the second movable element 2923 extends. The fourth axis corresponds to a direction orthogonal to the third axis about which the third joint 2933 rotates. The fifth axis corresponds to a direction orthogonal to the fourth axis about which the fourth joint 2934 rotates.

Each of the first movable element 2922 and the second movable element 2923 is a rod-like member extending in a particular direction, with its length appropriately designed according to a required range of movement of the robot arm 2901. The first movable element 2922 moves up and down, while staying parallel to the horizontal plane. The second movable element 2923 rotates about the second axis, while staying parallel to the first movable element 2922. This configuration does not require the second actuator 2942 to compensate for the gravity in the vertical direction, and the motor may thus be reduced in size. This configuration is advantageous in downsizing the robot arm 2901, and is advantageous in introducing the robot arm 1001 in the medical settings where only a limited space is available, or in ensuring a larger space for treatment and surgery.

The third movable element 2924 is provided at the distal end of the robot arm 2701. In the present example configuration, the distal end of the robot arm 2901 is coupled to a slide mechanism 2909 of the table 2908.

The robot arm 2901 includes: a plurality of actuators (first to fifth actuators 2941 to 2945 and a slide mechanism actuator 2949 in the present example configuration) associated with the first to fifth joints 2931 to 2935 and the slide mechanism 2909 to move or rotate the first to third movable elements 2922 to 2924 and the slide mechanism 2909; a plurality of position detectors (first to fifth position detectors 2951 to 2955 and a slide mechanism position detector 2959 in the present example configuration) built in the respective joints to detect the positions of the respective movable elements; and a controller 2907 which controls the actuation of the respective actuators. The controller 2907 is provided in the base 2921, but may also be an independent external device, for example.

The first to fifth actuators 2941 to 2945 and the slide mechanism actuator 2949 are servomotors, for example. Similarly to the first to fourth example configurations, encoders, resolvers, and potentiometers may be used as the position detectors.

Preferably, the robot arm 2901 further includes first to fifth electromagnetic brakes 2961 to 2965 and a slide mechanism electromagnetic brake 2969 associated with the first to fifth joints 2931 to 2935 and the slide mechanism 2909. If the robot arm 2901 does not include any electromagnetic brakes, the posture of the robot arm 2901 is maintained by actuating the plurality of actuators 2941 to 2945 and the slide mechanism actuator 2949. If the robot arm 2901 includes the electromagnetic brakes, the posture of the robot arm 2901 may be maintained by turning the electromagnetic brakes on even if some of the actuators are turned off.

In the case where the electromagnetic brakes are provided, each of the first to fifth electromagnetic brakes 2961 to 2965 is configured to turn its brake function on when no drive current is supplied to the associated one of the actuators, and to turn its brake function off when a drive current is supplied to the actuator.

Figure 30:
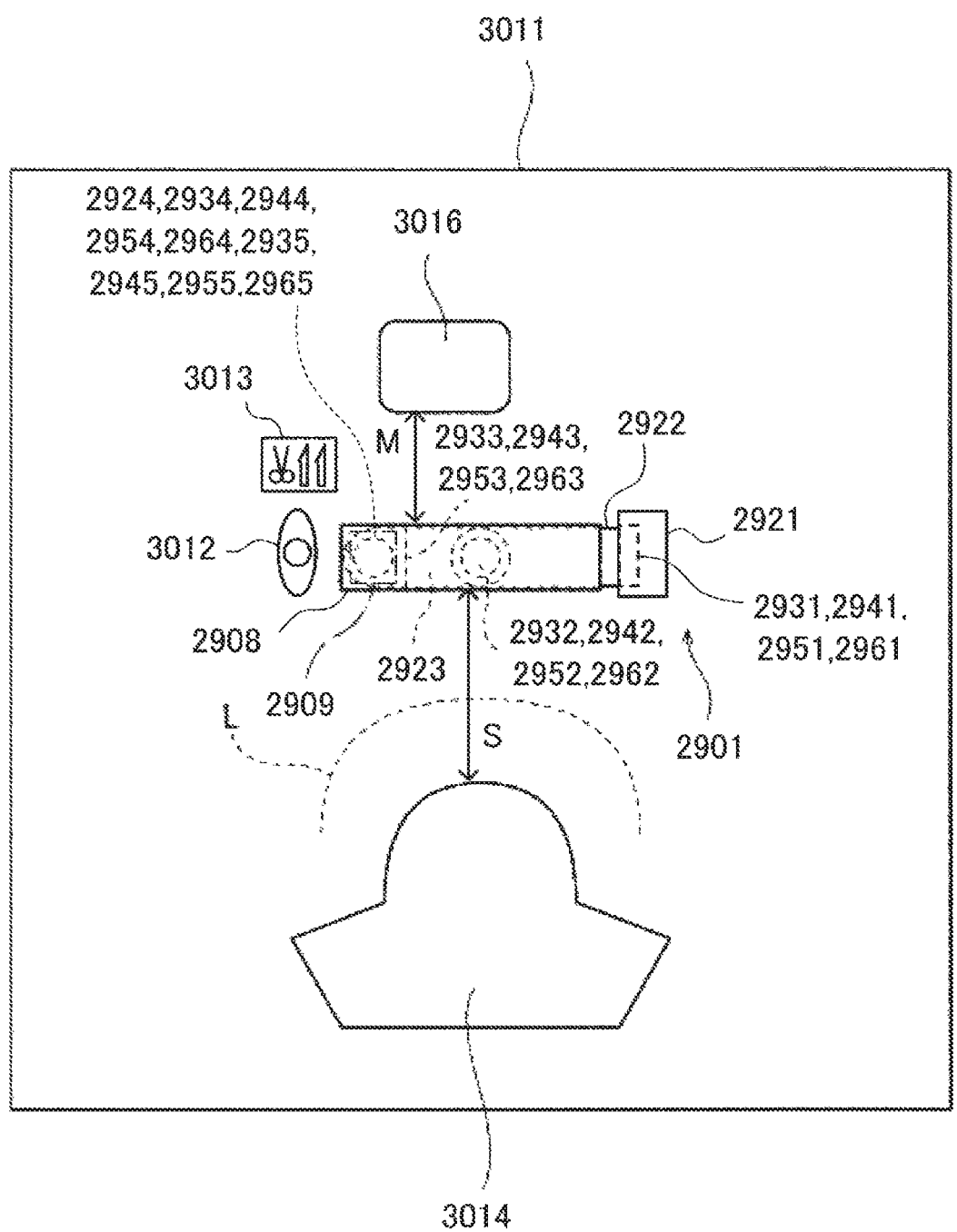
FIG. 30 is a diagram illustrating a plan view of the medical room where the robotic bed according to the fifth example configuration is placed, and shows a state in which the table is located at the first position.
Figure 31:
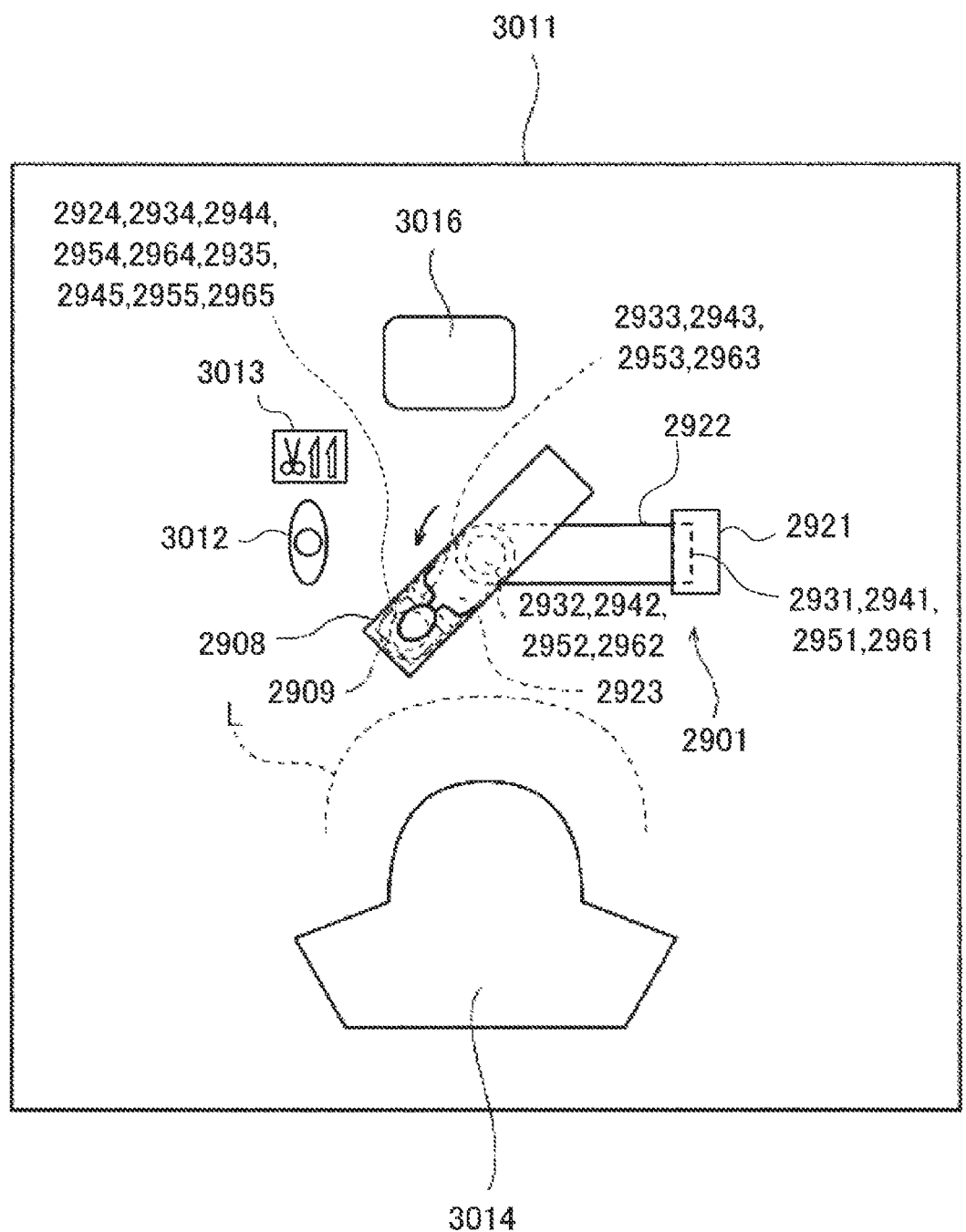
FIG. 31 is a diagram illustrating a plan view of the medical room where the robotic bed according to the fifth example configuration is placed, and shows the table in the middle of being transferred to the second position.

The placement position (i.e., the first position) illustrated in FIG. 30 where a target is to be placed is the same as the position illustrated in FIG. 6. However, the robotic bed having the slide mechanism inserts the table 2908 into the inspection device 3014 in the opposite direction. In other words, the table 208 illustrated in FIGS. 6 to 8 is inserted into the inspection device 614 from one end of the table 208, whereas the table 2908 illustrated in FIGS. 30 to 32 is inserted into the inspection device 3014 from the other end of the table 2908.

Figure 32:
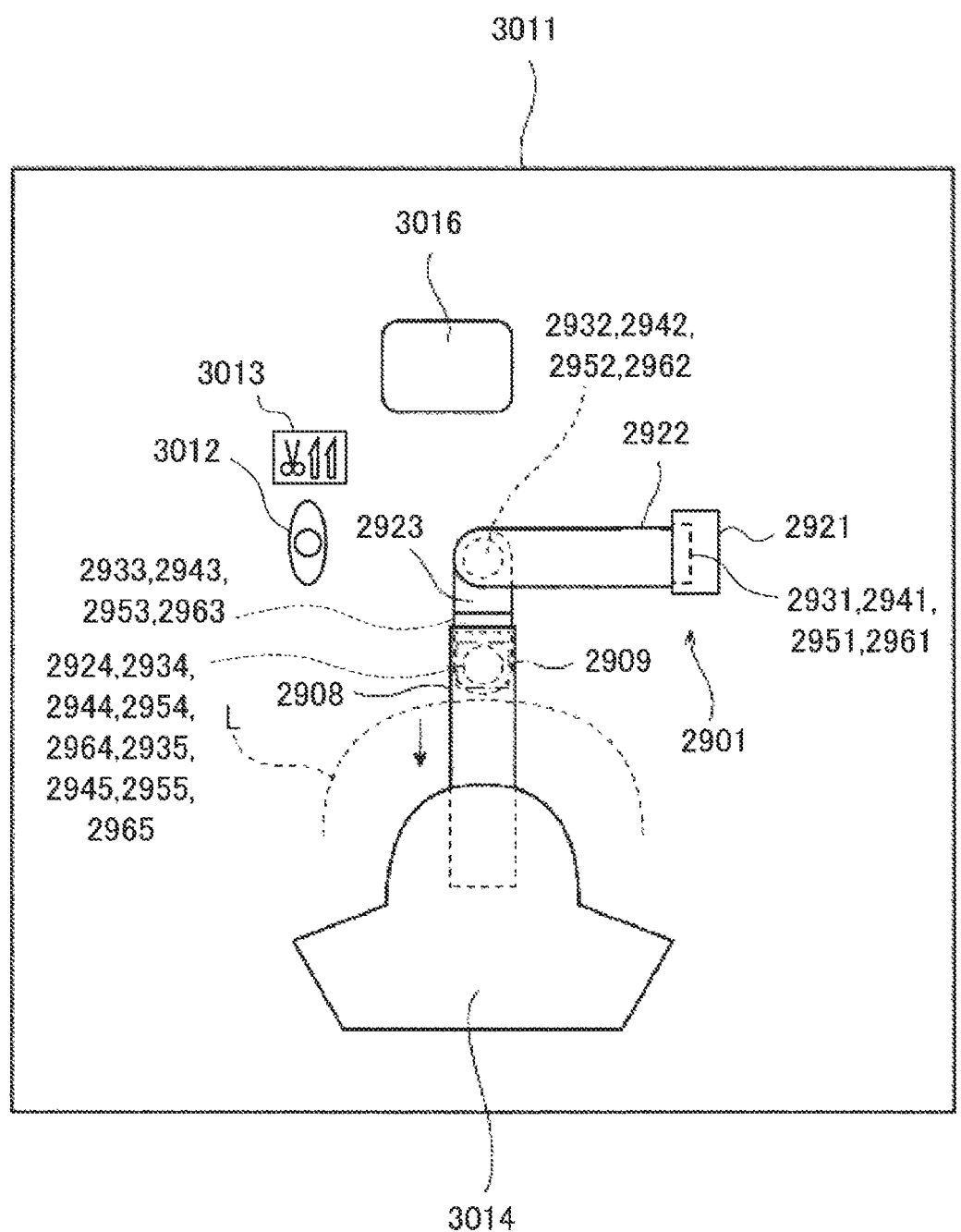
FIG. 32 is a diagram illustrating a plan view of the medical room where the robotic bed according to the fifth example configuration is placed, and shows a state in which a slide plate of the table is located at the second position.

The position (i.e., the inspection position) illustrated in FIG. 8 where the target is inserted into the inspection device 614 from his/her head is the same as the position shown in FIG. 32. In the first example configuration, the table 208 is transferred into the inspection device 614 from an oblique angle by simply operating the movable elements of the robot arm 201, whereas in the present example configuration, the table 2908 is located at an inspection preparation position, and then made to slide into the inspection device 2914 by the actuation of the actuator. The inspection preparation position is a position which is different from the inspection position and where the particular direction (i.e., the longitudinal direction) of the table is directed to an opening of the inspection device 614 and parallel to the particular direction (i.e., the longitudinal direction) of the table located at the inspection position.

Provision of such a slide mechanism provides an advantage of downsizing the robot arm, and also an effect that the orientation of the placed target at the placement position (i.e., the first position) is changeable in the first example configuration illustrated in FIG. 6 (in which the robot arm 201 supports one end portion of the table 208). As for the latter advantage, in a case, for example, where the first position is also a surgery position where surgery of the upper body (e.g., brain or teeth surgery) is performed, the surgeon 612 may have difficulty in performing the surgery if the patient comes back from the inspection device 614 with his/her head directed toward the base 221 as illustrated in FIG. 6, because the base 221 constitutes an obstacle. On the other hand, if the patient comes back from the inspection device 3014 with his/her head directed away from the base 2921 as illustrated in FIG. 29, it is easy to perform the surgery of the upper body. Since the base 2921 does not constitute an obstacle, the doctor 3012 is able to give treatment while seated.

In the examples described herein, the distal end of the robot arm supports the end portion of the table, but the man-powered slide mechanism may be adopted in a configuration in which the distal end of the robot arm supports a middle portion of the table. Further, the groove 2883 in the table, in which the actuator-driven slide mechanism 2909 is fitted, may be provided so as to extend only within the length of the middle portion. In that case, the sliding width decreases, but sagging of the table is less likely to occur compared to the case of a greater sliding width.

Further, the above examples illustrate a case in which an actuator-driven slide mechanism is employed in the first example configuration. However, a slide mechanism of either type, i.e., a manually-operated slide mechanism and an actuator-driven slide mechanism, may be employed in any of the example configurations.

If the slide mechanism is employed in the second and fourth example configurations, the robotic bed may be configured such that no matter how much the table position is changed by means of the slide mechanism, and how much the table is rotated, the table and the robot arm do not come into contact with each other as long as the table is maintained parallel to the horizontal plane. As for the first example configuration, it is preferable that the robotic bed is designed such that the table having the slide mechanism does not come into contact with the robot arm, no matter how much (e.g., by 360 degrees) the table is rotated from a position where the table is located closest to the base, while staying parallel to the horizontal plane without moving in the sliding direction, in a state in which particular directions of two movable elements, which are coupled together at their end portions by the horizontally-rotating joint, are parallel to each other when viewed from vertically above. As for the third example configuration, it is preferable that the robotic bed is designed such that the table having the slide mechanism does not come into contact with the robot arm, no matter how much (e.g., by 360 degrees) the table is rotated from a position where the table is located closest to the base, while staying parallel to the horizontal plane without moving in the sliding direction, in a state in which the second movable element 1523 is located deepest in the first movable element 1501 when viewed from vertically above. Designing the robotic bed in this manner may provide an advantage of the slide mechanism, as well, in addition to the advantage of the robotic bed of each example configuration.

[Common Features Among Example Configurations]

Additional features applicable to all of the first to fifth example configurations will be described below.

(Fixing Member for Tubes/Cords)

If the placed target on the table in each of the example configurations is a patient, the patient may sometimes be put on a life support system, a drip, or any other equipment necessary for the treatment. For example, the patient is connected to an anesthesia machine 616, 1216, 1716, 2416, and 3016 by a tube, for which measures need to be taken in moving the table.

As described above, compared to the configuration in which a table with a caster is moved, the robotic beds of the first to fifth example configurations may be prevented from being tangled with such tubes (tubes and/or cables) and from being wobbled by stepping over the tubes during the movement of the placed target. To ensure further safety, it is preferable that the robotic bed of one or more embodiments include a fixing member 271, 471, 571, 1071, 1171, 1571, 1671, 2071, and 2971 attached to at least one of the table, the base of the robot arm, or the movable element so as to bundle the tubes extending from the equipment mentioned above. This may prevent a situation in which tubes are tangled during the operation of the robot arm more reliably. Moreover, doctors or assistants are prevented from tripping over the tubes, which may further increase the safety. Tubes for which measures to prevent tangles are necessary are not limited to those connected to the equipment, such as a life support system. It is preferable that cords, such as electrical cords for medical equipment and displays, as well, be fixed with the same or similar fixing member. Further, if it is known to which position the table is to be moved, it is preferable that the movement of the robot arm be roughly predicted to determine how much of the lengths of the tubes/cords should be left unfixed, and where on the tubes/cords the fixing member is to be fitted.

(Manual Off-Brake Function)

If an electromagnetic brake associated with a horizontally-rotating joint is provided, a switch or a lever for manually turning the brake function off when no drive current is supplied to the actuator may be provided.

For example, in the case of the robot arm 201 illustrated in FIG. 2, of the first to fifth electromagnetic brakes 261 to 265, the second and fifth electromagnetic brakes 262 and 265 respectively associated with the second and fifth joints 232 and 235, which are horizontally-rotating joints, may be configured such that their brake functions can be turned off manually. In the case of the robot arm 1001 illustrated in FIG. 10, of the first to sixth electromagnetic brakes 1061 to 1066, the second, third, and sixth electromagnetic brakes 1062, 1063, and 1066 respectively associated with the second, third, and sixth joints 1032, 1033, and 1036, which are horizontally-rotating joints, may be configured such that their brake functions can be turned off manually. In the case of the robot arm 1501 illustrated in FIG. 15, of the first to fifth electromagnetic brakes 1561 to 1566, the fifth electromagnetic brake 1565 associated with the fifth joint 1535, which is a horizontally-rotating joint, and the second electromagnetic brake 1562 associated with the joint 1532 traveling horizontally straight, may be configured such that their brake functions can be turned off manually. In the case of the robot arm 2001 illustrated in FIG. 20, of the first to seventh electromagnetic brakes 2061 to 2067, the seventh electromagnetic brake 2067 associated with the seventh joint 2037, which is a horizontally-rotating joint, and the second electromagnetic brake 2062 associated with the joint 2032 traveling horizontally straight, may be configured such that their brake functions can be turned off manually. Further, in the case of the robotic bed illustrated in FIG. 29 which has a motor-driven slide mechanism, the motor which drives the slide mechanism, too, may be provided with an electromagnetic brake, and may be configured such that its brake function is turned off manually.

This configuration allows medical staff, for example, to transfer a patient (i.e., a placed target) to a safe place in the event of a power failure by turning off the brake functions of the movable elements and moving the movable elements of the robot arm.

Note that the manual off-brake function does not have to be applied to all of the above-listed electromagnetic brakes. Of course, it may be applied to at least some of the electromagnetic brakes or may be selectively applied to an electromagnetic brake provided at a joint that is movable only parallel to the horizontal plane.

(Distance Sensor)

It is preferable that the robot arm of each of the example configurations be equipped with a distance sensor 273, 473, 573, 1073, 1173, 1573, 1673, 2073, and 2973 (hereinafter referred to as "273 to 2973") which scans the range of movement of the robotic bed.

For example, in FIG. 2, the range of movement of the robot arm 201 forms a sector, of which the radius corresponds to the length from the second axis, about which the second joint 232 rotates, to the distal end of the table 208 when the robot arm 201 and the table 208 are extended to the maximum. In FIG. 10, the range of movement of the robot arm 1001 forms a sector, of which the radius corresponds to the length from the second axis, about which the second joint 1032 rotates, to the distal end of the table 1008 when the robot arm 1001 and the table 1008 are extended to the maximum. In FIG. 15, the range of movement of the robot arm 1501 forms a sector that is formed by the table 1508 rotated about the fifth axis at a position where the movable element 1523 is extended to the maximum away from the base 1521. In FIG. 20, the range of movement of the robot arm 2001 forms a sector that is formed by the table 2008 rotated about the seventh axis at a position where the movable element 2023 is extended to the maximum away from the base 2021. In FIG. 29, the range of movement of the robot arm 2901 forms a sector, of which the radius corresponds to the length from the second axis, about which the second joint 2932 rotates, to the distal end of the table

2908 when the table 2908 is extended to the maximum to one side (i.e., away from the base 2921) by the robot arm 2901 and the slide mechanism.

When such a distance sensor 273 to 2973 detects a foreign object (a human being or an object) within the range of movement of the robot arm, the controller 207, 407, 507, 1007, 1107, 1507, 1607, 2007, and 2907 (hereinafter referred to as "207 to 2907") stops or prohibits the actuation of all the actuators. This configuration reduces risks, such as contact and collision of a human being with the robot arm or the table, even when the human being, such as medical staff, who is not well acquainted with the robot operation and thus has difficulty in predicting the movement of the robot arm, is staying close to the robotic bed. Further, other risks, such as contact and collision of the robot arm with medical equipment, are also avoidable.

It is preferable that the state of the distance sensor be controlled to be active or inactive according to the location of the table in order to prevent the distance sensor from reacting to the doctor or assistant who surrounds the table when, for example, the table arrives at the treatment position. In this case, a manually operated switch for switching the state of the distance sensor between the active and inactive states should be provided. Alternatively, a controller may control the switching of the state of the distance sensor between the active and inactive states.

(Height Sensor)

It is preferable that the table or the robot arm be equipped with a height sensor 274, 474, 574, 1074, 1174, 1574, 1674, 2074, and 2974 (hereinafter referred to as "274 to 2974") configured to detect the height of the table 208, 408, 508, 1008, 1108, 1508, 1608, 2008, and 2908 (hereinafter referred to as "208 to 2908"). In this case, the controller 207 to 2907 determines whether or not the height of the table 208 to 2908 detected by the height sensor 274 to 2974 is in a predetermined range, before the table 208 to 2908 is moved into the inspection device. If the detected height is not in the predetermined range, the controller 207 to 2907 does not allow the table 208 to 2908 to move into the inspection device. This configuration reduces risks, such as contact and collision of the table or the subject with the inspection device. Although in the above description the inspection position is adopted as an example target position to which the table is transferred, the target position may also be, for example, the measurement position and the imaging position, where the table is inserted in a device related to medical care (i.e., a measurement device and an imaging device, respectively).

(Sagging Compensation)

Figure 33A:
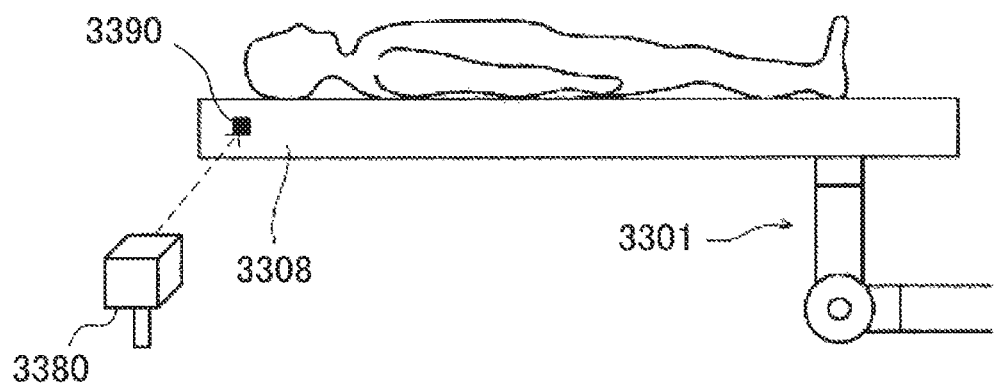
FIGS. 33A, 33B, and 33C are diagrams illustrating an example in which the robot arm is controlled by a sagging correction function.
Figure 33B:
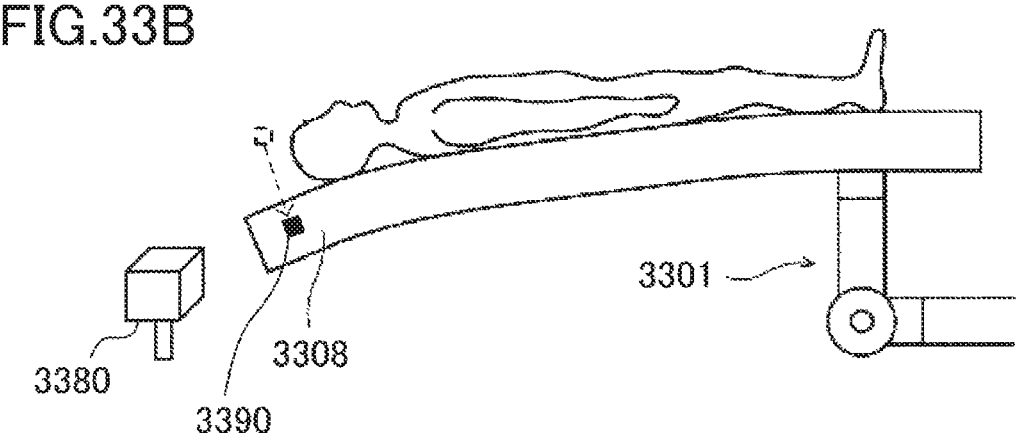
Figure 33C:
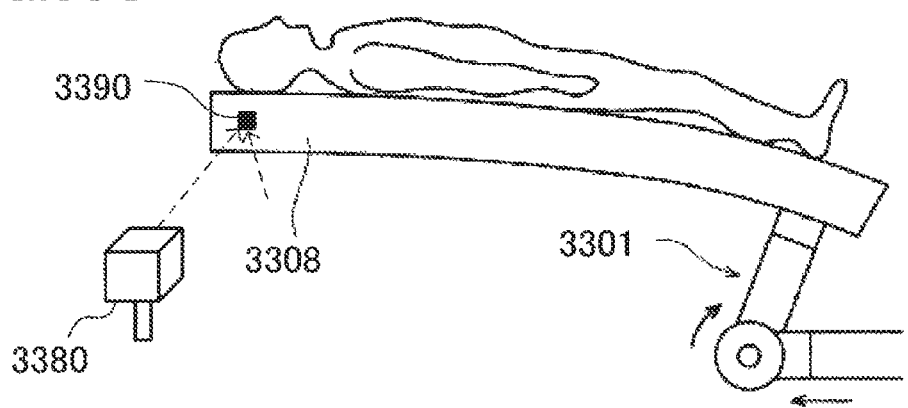

Further, the robot arm of each of the example configurations has the function of compensating for the sagging of the table or the robot arm by controlling the robot arm through the controller 207 to 2907 according to the degree of sagging of the table or the robot arm. FIGS. 33A, 33B, and 33C are diagrams illustrating examples of how to make correction to the sagging of the table 3308 caused by the weight of the placed target, for instance. For example, a visible or invisible marker 3390 is provided at a side surface of the end portion of the table 3308. The position of the table 3308 is detected by detecting the position of the marker through image detection by an external camera or by a position recognition device 3380, such as an infrared camera. The detected position can be stored in the controller 207 to 2907 (FIG. 33A). The position recognition device 3380 is disposed such that the position of the table can be detected in a space where an image is taken. If the table warps as illustrated in FIG. 33B, the marker 3390 moves to lower right, for example. The external camera detects this shift of the position of the table 3308. The controller controls at least one of the actuators so as to return the marker back to the position stored in advance and correct the shift. In the example illustrated in FIG. 33C, the shift is corrected by moving one of the movable elements of the robot arm to the left, and rotating the vertically-rotating joint clockwise.

Figure 34A:
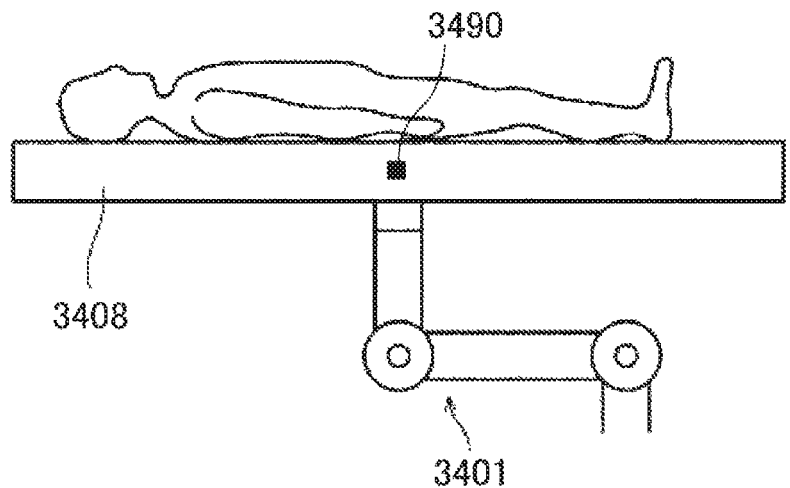
FIGS. 34A, 34B, and 34C are diagrams illustrating another example in which the robot arm is controlled by a sagging correction function.
Figure 34B:
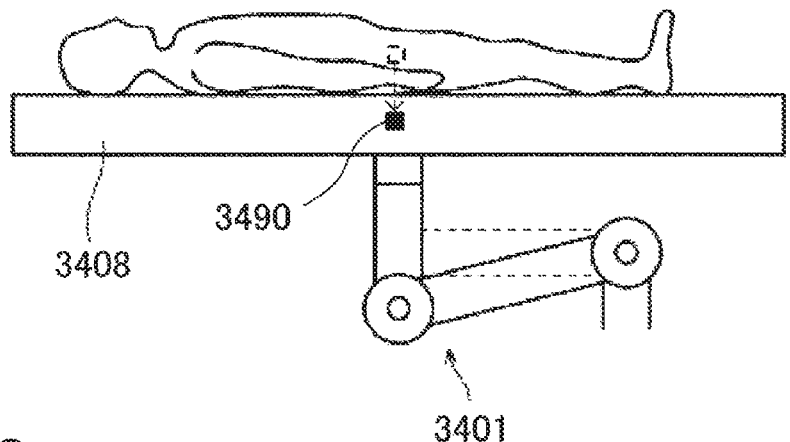
Figure 34C:
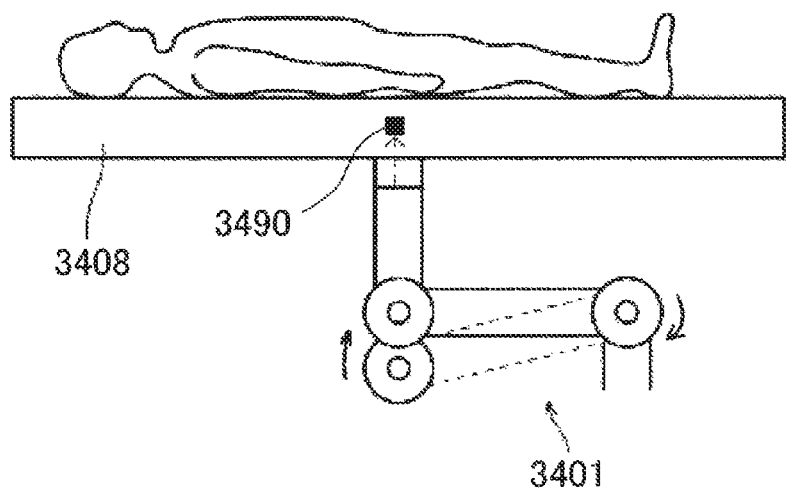

FIGS. 34A, 34B, and 34C are diagrams illustrating other examples of sagging compensation. For example, if the marker 3490 is positioned at a middle portion of the table, the controller 207 to 2907 can store this position as an initial position of the table 3408 (FIG. 34A). If the table warps and the marker 3490 moves down, for example, as illustrated in FIG. 34B, the controller 207 to 2907 of the robot arm detects the shift of the position of the marker 3490, and controls at least one of the actuators so as to return the marker 3490 back to the position stored in advance and correct the shift. In the example illustrated in FIG. 34C, two vertically-rotating joints of the robot arm are rotated clockwise to correct the shift.

Other examples of correcting the sagging include providing a current measurement device which measures a current value of the actuator provided at each of the joints. A load is estimated from the measured current value. Sagging can be corrected according to the estimated load. In this case, a sagging amount corresponding to a load amount may be stored in advance in a memory, or the sagging amount may be appropriately obtained through a known calculation, thereby making it possible to determine an amount of sagging correction by each joint. The position of the table can be corrected according to the amount of sagging correction by controlling at least one of the joints as in the examples illustrated in FIGS. 33 and 34.

These configurations allow the table to stay at a target position all the time. For example, even when the table is moved away from the base by the operation of the slide mechanism, the vertical position of the table is appropriately corrected during the movement. This configuration allows the placed target to be transported to an accurate position, for example, and also reduces risks, such as contact and collision of the table or the placed target with an inspection device, a measurement device, an imaging device, etc.

(Weight Sensor)

It is preferable that the table or the robot arm be equipped with a weight sensor 275, 475, 575, 1075, 1175, 1575, 1675, 2075, and 2975 (hereinafter referred to as "275 to 2975") which measures the weight of the placed target. This configuration allows monitoring of the weight of the patient, who is a placed target, all the time, for example. According to this configuration, the patient, who is a placed target, may be monitored in terms of his/her weight. For example, the weight before the start of the surgery may be stored, and the weight reduced by bleeding may be monitored as a reference in determining surgery procedure and changing the surgery strategy. Thus, it is preferable that the table or the robot arm have a display unit (e.g., a display window or a display) on which numerical values detected by the weight sensor are displayed. Further, it is preferable that this display unit be configured to display a plurality of values recorded (e.g., values recorded before surgery and immediately after the surgery with bleeding) and/or a difference between a stored value and a current value (e.g., a difference between a pre-surgery value and a current value). To achieve this, it is preferable that a storage device, such as a memory, be provided to store the weight of a placed target in the storage device at some point of time, and that an arithmetic unit, such as a CPU, which calculates a difference between the current weight of the placed target detected by the weight sensor and the weight that has been stored, be provided as well. Further, in order to provide such management for an individual patient, who is a placed target, it is preferable that the storage device be configured to select the patient in association with his/her patient ID, store the weight of the patient at some point of time, calculate the difference between the stored weight and the current weight, and display the difference on the display unit.

(Temperature Sensor)

It is preferable that the table be equipped with a temperature sensor 272, 472, 572, 1072, 1172, 1572, 1672, 2072, and 2972 (hereinafter referred to as "272 to 2972") which measures the temperature of the placed target. This configuration allows monitoring of the temperature of the patient, who is a placed target, all the time, for example. According to this configuration, the patient, who is a placed target, may be monitored in terms of his/her body temperature. For example, the body temperatures before the start of surgery, while waiting for the start of the surgery, during the surgery, and after the surgery may be monitored. It is therefore preferable that the table or the robot arm have a display unit for displaying thereon the numerical values detected by the temperature sensor.

It is preferable that a temperature increasing device (e.g., a heater) for increasing a surface temperature of the table 208 to 2908 or a temperature decreasing device (e.g., a cooling device) for decreasing the surface temperature of the table 208 to 2908 be provided for an event that the body temperature of the patient is too low or too high. This configuration can maintain the patient at a desired body temperature.

In each of FIGS. 2, 4, 5, 10, 11, 15, 16, 20, 21, 22, and 29, the temperature sensor is arranged on a side surface of the table 208 to 2908. However, the temperature sensor may be embedded in the table.

Further, another temperature sensor which detects an ambient temperature around the table may be provided to keep the patient at a desired body temperature while he or she is waiting for the start of the surgery and resting after the surgery. The robot arm may be controlled to move the table to an area where the temperature is low (e.g., to a lower position or close to a cooler) if the ambient temperature is high, or to an area where the temperature is high (e.g., to a higher position or close to a heater) if the ambient temperature is low. Since these automatic movements may be made while the patient is at rest after the surgery or while the patient is waiting for treatment, it is preferable that the table be moved so slowly that the person placed on the table does not sense the movement. However, since the robot arm should not move automatically during surgery, sensors may be switched between active and inactive states according to the area where the table is located. For example, sensors may be set to be inactive when the table is located at the treatment position.

It is preferable that the temperature sensor and the ambient temperature sensor be configured such that the sensor function thereof may be switched manually between the active and inactive states.

(Object Sensor)

Further, it is preferable that the table be equipped with at least one object sensor for detecting an object around the table, and that the actuation of the actuator driving the robot arm be stopped or prohibited if the object sensor detects an object while the robot arm is in motion. Since ensuring safety is highly prioritized in employing, in a medical room, such a robotized bed as described in the first to fifth example configurations, it is preferable that the safety of the patient and medical staff be ensured by devices such as this object sensor.

Note that the object sensor may be switched between active and inactive states according to the area where the table is located. For example, the object sensor may be set to be inactive when the table is at the treatment position, or may be set to be active only while the table moves between the placement position where the target is placed and the inspection position. The object sensor may be switched between the active and inactive states by the controller, or may be switched between the active and inactive states with a manual switching member provided at the object sensor.

It is preferable that the temperature sensor and the ambient temperature sensor be configured such that the sensor function thereof may be switched manually between the active and inactive states.

(Configuration of Controller)

Figure 48:
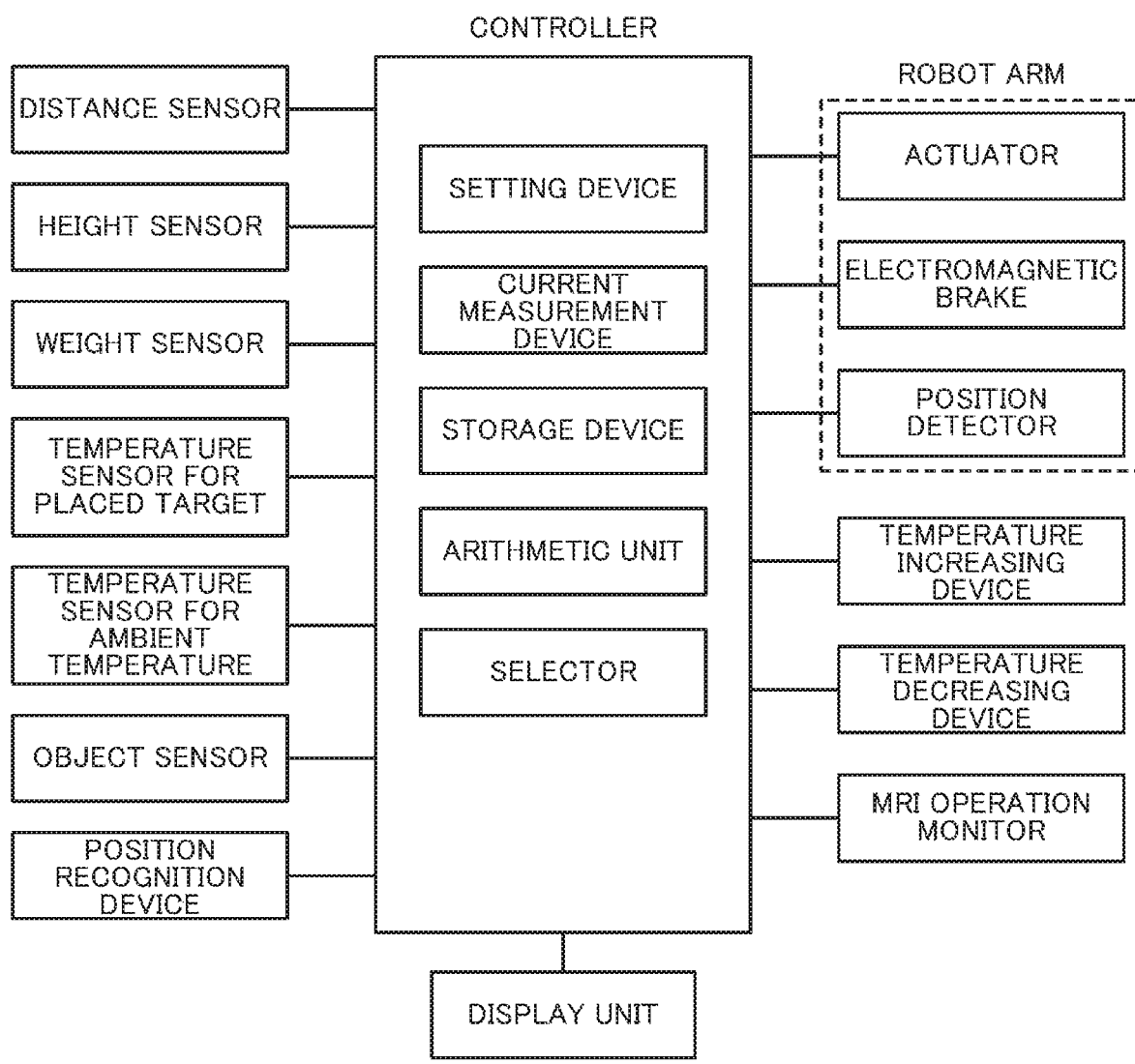
FIG. 48 is a block diagram illustrating a configuration of a controller.

As illustrated in FIG. 48, the controller 207 to 2907 is connected to the actuator, the electromagnetic brake, and the position detector of the robot arm 201, 401, 501, 1001, 1101, 1501, 1601, 2001, and 2901 (hereinafter referred to as "201 to 2901"). Further, the controller 207 to 2907 may be connected to the above-described distance sensor 273 to 2973, the height sensor 274 to 2974, the weight sensor 275 to 2975, and the temperature sensor 272 to 2972. Moreover, the controller 207 to 2907 may include a storage device, and may also include, as a configuration that achieves the above-described sagging compensation, a setting device configured to specify the position of a target point, and a tracking device configured to track the target point. The storage device is a non-volatile memory, such as a ROM.

Further, the controller 207 to 2907 may include the above-described storage device and arithmetic unit, or may be connected to the above-described display unit. The display unit may be built in the base of the robot arm, or may be independent of the robot arm. Further, if the weights of a plurality of different targets are stored in the storage device of the controller, the controller may include a selector configured to select a particular target to be placed as illustrated in FIG. 48.

The controller 207 to 2907 may be connected to the above-described temperature increasing device and temperature decreasing device. Further, the controller 207 to 2907 may be connected to the above-described object sensor.

(Table Design)

The table 208 to 2908 of each of the above-described example configurations can be appropriately designed according to the circumstances, such as the size of the medical room and a surgical method. Considering the function of the table as a table top, the table should have a length of at least 210 cm so that a tall patient, for example, can be placed on the table as a target.

Figure 50A:
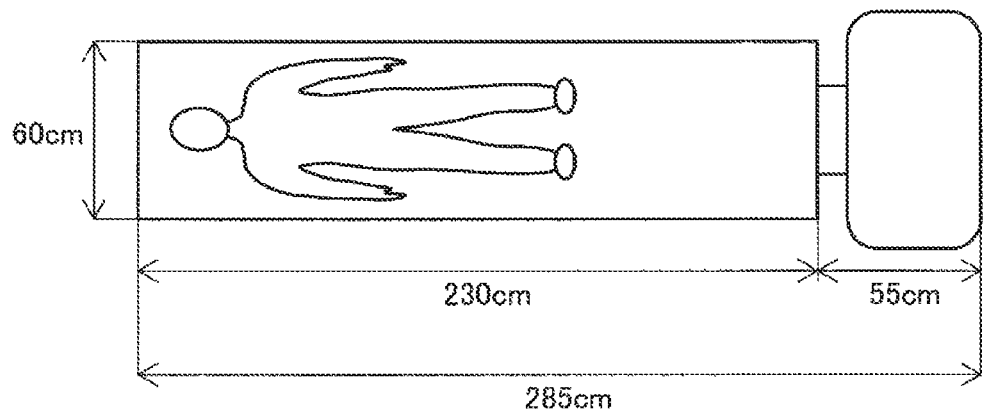
FIGS. 50A and 50B are diagrams illustrating dimensions of the table and other parts of the robotic bed.

As illustrated in FIG. 50A, if the robotic bed is configured to allow the robot arm to protrude from under the table while the robotic bed is taking a position requiring a minimum space in the medical room, it is desirable that the size of the entire robotic bed be determined in consideration of the robot arm protruded from under the table. If the robot arm protrudes in the longitudinal direction of the table, the longitudinal dimension of the table should be determined to be shorter than 240 cm because the total length of the robotic bed in the space-saving position is desirably shorter than 300 cm. Preferably, the protrusion amount of the robot arm from under the table is one fourth (i.e., ¼) or less of the longitudinal dimension of the table. Thus, if the longitudinal dimension of the table is about 240 cm, the maximum allowable dimension of the protrusion of the robot arm from under the table in the space-saving position is about 60 cm. The table exemplified in FIG. 50A has a longitudinal dimension of 230 cm. The dimension of the robot arm not hidden under the table is therefore set to be 55 cm, which is shorter than one fourth (i.e., ¼) of the longitudinal dimension of the table (i.e., 230 cm). A shorter longitudinal dimension of the table allows the driving force (i.e., the motor) to have reduced size. Thus, the protrusion amount of the robot arm from under the table can be slightly reduced.

Figure 50B:
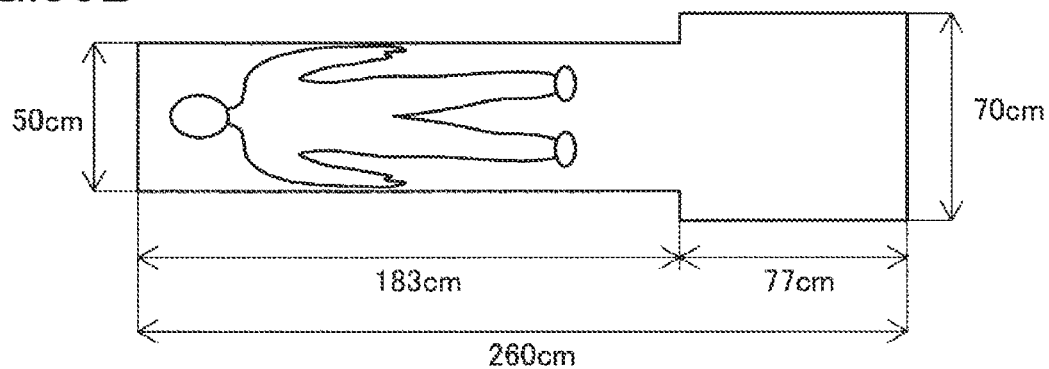

On the other hand, if the robotic bed is configured such that the robot arm is completely hidden under the table while the robotic bed is taking a space-saving position, as illustrated in FIG. 50B, the table is often required to be larger in size so that the robot arm is housed under the table, because the robot arm capable of withstanding a load of about 200 kg, for example, needs to be relatively large in size. Thus, the longitudinal dimension of the table is preferably at least 240 cm, which is longer, for example, than the longitudinal dimension of the table in the configuration allowing the robot arm to protrude from the table. Further, it is preferable that the longitudinal dimension of the table in the configuration allowing the robot arm to be completely hidden under the table be determined to be shorter than 300 cm because the total length of the robotic bed in the space-saving position is desirably shorter than 300 cm. The table exemplified in FIG. 50B has a longitudinal dimension of 260 cm. In the above description, the case where the robot arm to protrude from under the table and the case where the robot arm is completely hidden under the table are differenciated based on the criteria whether the length of the table is more than 240 cm. However the cases do not always need to be differenciated based on a certain value of the length of the table. It is not intended to exclude a case in which a range of length values of the table in one case may overlap with a range of length values of the table in the other case.

If the width dimension of the table is too small, it may increase the risk of falling of the patient (i.e., a placed target) from the table. If the width dimension of the table is too large, it may serve as an obstacle in reducing the space required. It is therefore preferable to design the width dimension of the table appropriately according to a customer request. Preferably, the width of the table is about 45 cm or wider, and shorter than 90 cm not as big as a regular sized single bed. The width of the table is set to be 60 cm in the example illustrated in FIG. 50A. A T-shaped table is adopted in the example illustrated in FIG. 50A. The width of the T-shaped table on one end (a narrow portion) is set to be 50 cm. The width of the T-shaped table on the other end (a wide portion) is set to be 70 cm. Note that a dimension simply referred to as a "width dimension" in the present specification refers to a maximum width of the table unless otherwise specified. Note that the table having a rectangular shape as in FIG. 50A and a T-shape as in FIG. SOB as viewed from vertically above is useful in bringing a stretcher close to and along a side of the table and moving the patient (i.e., a placed target) onto the table.

[Application to Hybrid Operation]

The term "hybrid operation" as used herein refers to carrying out surgery on a patient and capturing of an image of a specific site (an affected area) alternately (at least one back-and-forth movement). The term "hybrid operating room" refers to an operating room equipped with an operation table on which a patient is placed for surgery, and a medical imaging device (i.e., a modality) used to capture an image of a specific site (an affected area). Examples of the medical imaging device include a computerized tomography (CT) scanner, a magnetic resonance imaging (MRI) device, a digital radiographic (DR) imager, a computed radiographic (CR) system, an angiographic X-ray system (an angiographic device, XA), and an ultrasonographic (US) system.

A medical system employing the robotic beds which have been described so far in a hybrid operation will be described below. The medical system is provided with a base, a robotic bed configured to support a table by a robot arm having movable elements coupled together by a joint, and a medical imaging device.

In the medical system which will be described below, the robot arm is capable of moving the table between a first position where a large portion of the robot arm other than at least the base and the one end portion of the movable element connected to the base is hidden under the table, when viewed from vertically above, and a second position where at least a portion of the robot arm other than the base and the one end portion of the movable element connected to the base is not hidden under the table, when viewed from vertically above. The second position is an imaging position where an image is taken by the medical imaging device or an imaging preparation position. The first position is determined to be a position where the shortest distance between the robotic bed and a location of the medical imaging device at the imaging position or a setback position of the medical imaging device is at least a predetermined distance.

In the hybrid operation, in general, an anesthesia introducing process is carried out subsequent to a placement process for placing a patient on the table. Preferably, an anesthesia introducing position of the table is located at a third position where at least a portion of the robot arm other than the base and the one end portion of the movable element connected to the base is not hidden, when viewed from vertically above, and different from the second position. If the surgery position (the first position) and the anesthesia introducing position (the third position) are located at the same position, it is necessary to bring the anesthesia machine closer to the table during the introduction of anesthesia, and set back the anesthesia machine during the surgery to keep a surgery space. In such a situation, it is more efficient to move the patient by using the robotic bed according to the various example configurations described above, than to move the anesthesia machine. Moreover, it is possible to avoid the risk of falling of the anesthesia machine. Further, the anesthesia introducing position is located at the third position because if the anesthesia introducing position is located at the same position as the second position (i.e., the imaging position), the imaging device and the anesthesia machine are brought close to each other, casing a situation in which the device or machine not in use during an imaging process or the anesthesia introducing process constitutes an obstacle, and adversely affecting the efficiency and the safety.

Note that the patient placement position may be the same as, or different from, the anesthesia introducing position. If the placement position is the same as the anesthesia introducing position, the transfer process from the placement position to the anesthesia introducing position can be omitted. If the placement position is different from the anesthesia introducing position, preparations for a first stage of the anesthesia introducing process can be made at a place with sufficient space apart from the anesthesia machine.

(Case Using MRI Apparatus as Medical Imaging Device)

The robotic beds described above are expected to provide significant effects when used in an intraoperative MRI, in which surgery on an affected area and capturing of an image of the affected area by the MRI apparatus are alternately carried out (at least one back-and-forth movement). In the intraoperative MRI for removing brain tumors, the number of times of moving the patient and imaging his/her brain with the MRI apparatus is defined to be 2 to 4, and 3 on average (see "JIYUKUKAN" Vol. 25, Appendix of "Frontline system for total removal of brain tumor which allows increasing survival rate and ensuring postoperative QOL," Hitachi Medical Corporation, INNERVISION, September (2012)). Thus, there is a high need for moving the patient back and forth between the imaging position, where images are taken by the MRI apparatus, and the treatment position accurately and quickly during surgery.

Described below is a technique for applying the robotized beds having the first to fifth example configurations (in some cases, the robotized beds with the above-described common additional features) to the intraoperative MRI, in which images of a specific site of a patient as a placed target are taken by an MRI apparatus, and thereafter the patient is moved to a surgery position where surgery is performed immediately.

In the following description, it will be described, with reference to the drawings, how the table 208 to 2908 is moved between the surgery position and the MRI scanning position by actuating the robot arm 201 to 2901.

If the robotic beds of the respective example configurations are applied to the intraoperative MRI, the apparatuses 614, 1214, 1714, 2414, and 3014 placed in the operating room in the description of the movement of the table having the respective example configurations are MRI apparatuses.

Figure 35:
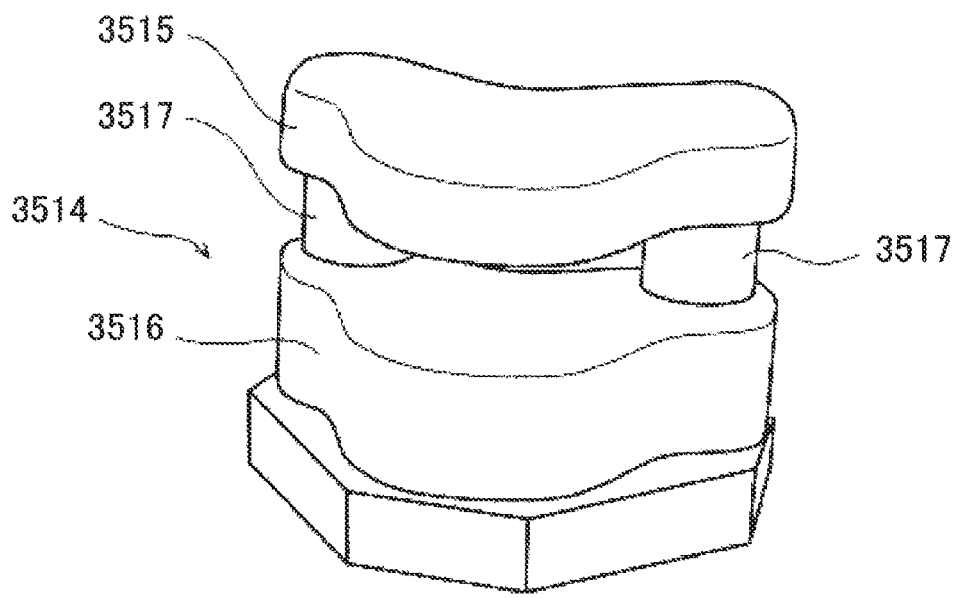
FIG. 35 is a diagram illustrating a perspective view of an MRI apparatus.

FIG. 35 illustrates an open MRI apparatus 3514. The open MRI apparatus 3514 is open at the front and lateral sides. Specifically, the open MRI apparatus 3514 includes an upper inspection section (an upper magnet) 3515 and a lower inspection section (a lower magnet) 3516, each of which is in an approximately T-shape with its middle portion protruding forward. Formed between these inspection sections 3515 and 3516 is a space in which the table, where the patient is placed, is to be inserted. The upper and lower inspection sections 3515 and 3516 are coupled together by a pair of support columns 3517 at their respective end portions. The MRI apparatus 3514 may also be a donut-shaped MRI apparatus. However, if the donut-shaped MRI apparatus 3514 is applied to a case (e.g., the case illustrated in FIG. 7) in which the patient is easily inserted in the MRI apparatus from an oblique angle, the table needs to be positioned in front of the hollow of the donut before being inserted into the hollow, which may make the movement of the robot arm a little less flexible.

The space defined between the upper inspection section (i.e., the upper magnet) 3515 and the lower inspection section (i.e., the lower magnet) 3516 is an imaging space. It can be said that the table 208 to 2908 is in the MRI scanning position when at least part of the table 208 to 2908 overlaps with this imaging space. The position of the table 208 to 2908 in the imaging space is not always the same, and differs depending on a site to be imaged of the patient and the height and size of the patient. However, a particular position in the imaging space can be stored in a memory in the controller. In a typical hybrid operation, the table moves back and forth between the surgery position and the imaging position multiple times. Thus, the imaging position and/or the surgery position for each surgery may be stored in the memory.

FIG. 6 illustrates a state in which the table 208 on which the patient is to be placed is located at the surgery position (i.e., the first position) in the process of moving the table 208 from the surgery position (i.e., the first position) to the MRI scanning position (i.e., the second position) using the robotic bed according to the first example configuration. As illustrated in FIG. 6, since the table 208 is located at the first position, portions of the robot arm 201 which are the base and the one end portion of the movable element connected to the base are not hidden under the table 208 on one of the longitudinal ends of the table 208, and the rest of the robot arm 201 is hidden under the table 208, when the table 208 is viewed from vertically from above. The maximum dimension of the robot arm 201 not hidden under the table 208 is less than one fourth (i.e., ¼) of the longitudinal dimension of the table 208.

FIG. 7 illustrates a state in which the second movable element 223 and the table 208 are moved by the control of the controller 207 as the arrows indicate (in some cases, the first movable element 222, too, is moved in the vertical direction to have its height adjusted, and the table 208 is rotated about the third axis and/or the fourth axis to have its tilt with respect to the longitudinal direction and/or the width direction of the table finely adjusted), causing the head of the patient to move toward the MRI apparatus 614 from an oblique angle. FIG. 8 illustrates a state in which one end portion of the table 208 is inserted in the MRI apparatus 614, and the patient has arrived at the MRI scanning position which is the second position. As illustrated in FIG. 8, of the robot arm 201, the entire movable element 222 directly connected to the base 221, and one end portion of the movable element 223 not directly connected to the base 221, are not hidden under the table 208. The maximum dimension of the robot arm 201 not hidden under the table 208 is at least one fourth (i.e., ¼) of the longitudinal dimension of the table 208.

If the table 208 needs to be moved to the surgery position after the capturing of images by the MRI apparatus 614 so that the surgeon 612 can perform surgery on the patient, the respective movable elements are controlled by the controller 207 to cause the table 208 to move in reverse direction from the MRI scanning position (i.e., the second position) illustrated in FIG. 8 to the surgery position (i.e., the first position) illustrated in FIG. 6. The table 208 returns to the surgery position in this manner, where the surgeon 612 can immediately start appropriate surgery while viewing the images taken by the MRI apparatus 614.

Now, a case in which the table 208 is transferred also to the anesthesia introducing position (i.e., the third position) in addition to the surgery position (i.e., the first position) and the imaging position (i.e., the second position) will be described.

In the intraoperative MRI, in general, an anesthesia introducing process is carried out subsequent to a placement process for placing a patient on the table. Note that the patient placement position may be the same as, or different from, the anesthesia introducing position.

Figure 39:
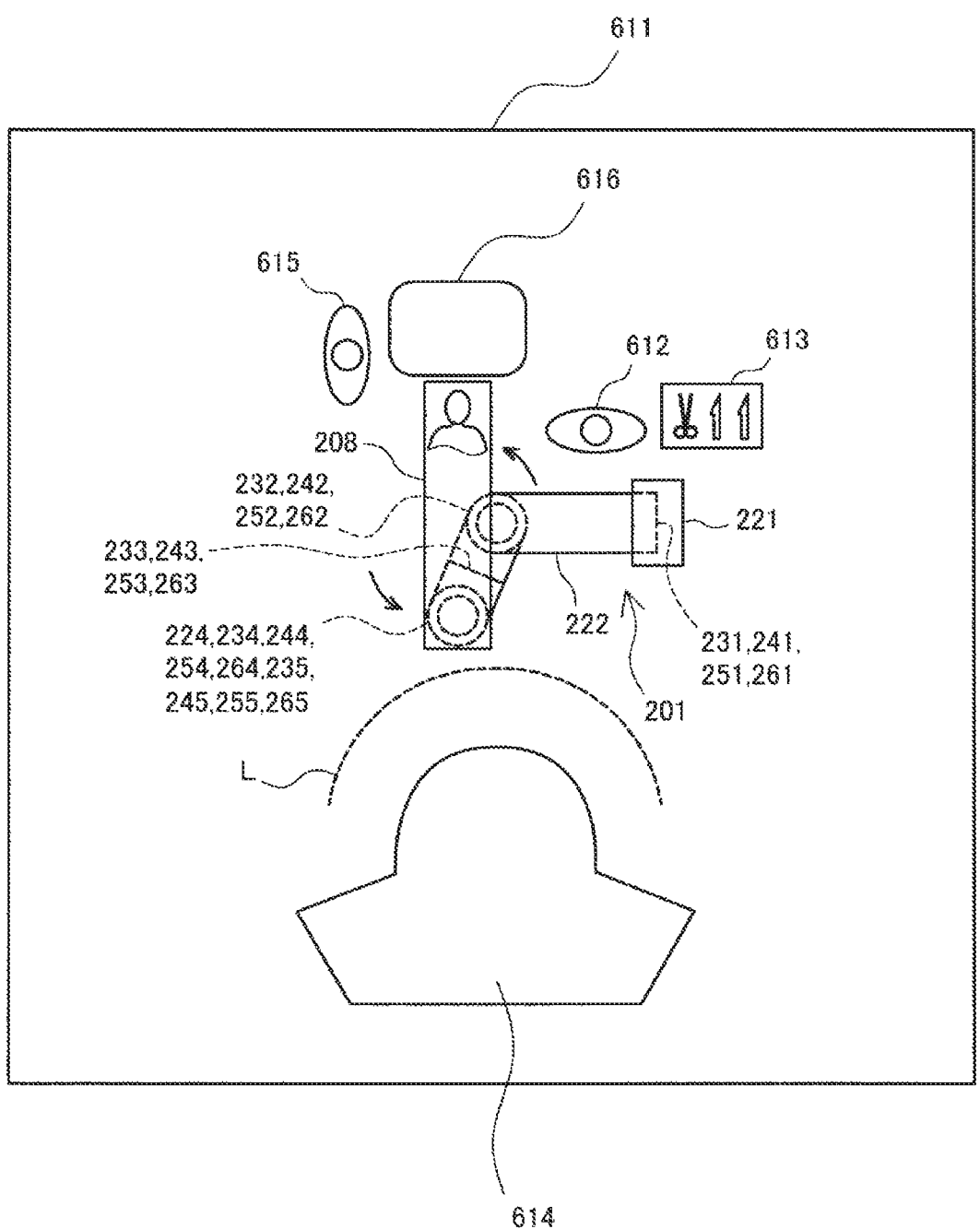
FIG. 39 is a diagram illustrating a plan view of the medical room where the robotic bed according to the first example configuration is placed, and shows a state in which the table is located at a third position.

FIG. 39 illustrates a case in which the patient placement position is different from the anesthesia introducing position, and the same as the surgery position. In FIG. 39, the table 208 is transferred from the placement position located at the first position to the anesthesia introducing position located at the third position.

After the patient is placed on the table 208 at the first position, the second and fifth joints 232 and 235 are rotated (in some cases, the height of the table 208 is adjusted by the first joint 231, and the tilt of the table 208 with respect to the longitudinal direction and/or the width direction of the table 208 is adjusted by the third and/or fourth joint 233, 234) to cause the table 208 to move as the arrows indicate in FIG. 39 to a position where one end of the table 208 is close to the anesthesia machine 616. The distance between the anesthesia machine and the table at this position close to the anesthesia machine is about 10 cm to 40 cm (although the distance may vary depending on the location of the patient on the table), considering that an anesthesiologist uses one hand to put a mask or the like provided at the end of tube on the patient's mouth, and the other hand to handle a pump of the anesthesia machine. At the anesthesia introducing position (i.e., the third position) illustrated in FIG. 39, the base 221 and the movable element 222 directly connected to the base 221 are not hidden under the table 208, when the table 208 is viewed from vertically above. The maximum dimension of the robot arm 201 not hidden under the table 208 is at least one fourth (i.e., ¼) of the longitudinal dimension of the table 208. Note that this transfer process is omitted if the placement position is the same as the anesthesia introducing position.

The anesthesiologist 615 then gives anesthesia to the patient. After the completion of the anesthesia, the respective movable elements are moved to cause the table 208 to move in the direction opposite to the direction of the arrows illustrated in FIG. 39, so that the table 208 is transferred to the surgery position, which is the first position. The surgeon 612 performs surgery on the patient based on the information of the image captured by the MRI apparatus prior to the surgery. After brain tumors, for example, are removed, the table 208 is transferred to the imaging position, which is the second position, as described above, where the affected area (e.g., brain) is subjected to MRI. The table 208 is then transferred back to the surgery position located at the first position. If there is a remaining tumor, for example, the surgeon 612 continues to perform the surgery.

FIG. 12 illustrates a state in which the table 1008 on which the patient is to be placed is located at the surgery position (i.e., the first position) in the process of moving the table 1008 from the surgery position (i.e., the first position) to the MRI scanning position (i.e., the second position) using the robotic bed according to the second example configuration. As illustrated in FIG. 12, since the table 1008 is located at the first position, the entire robot arm 1001 is hidden under the table 1008 when the table 1008 is viewed from vertically above.

Figure 13:
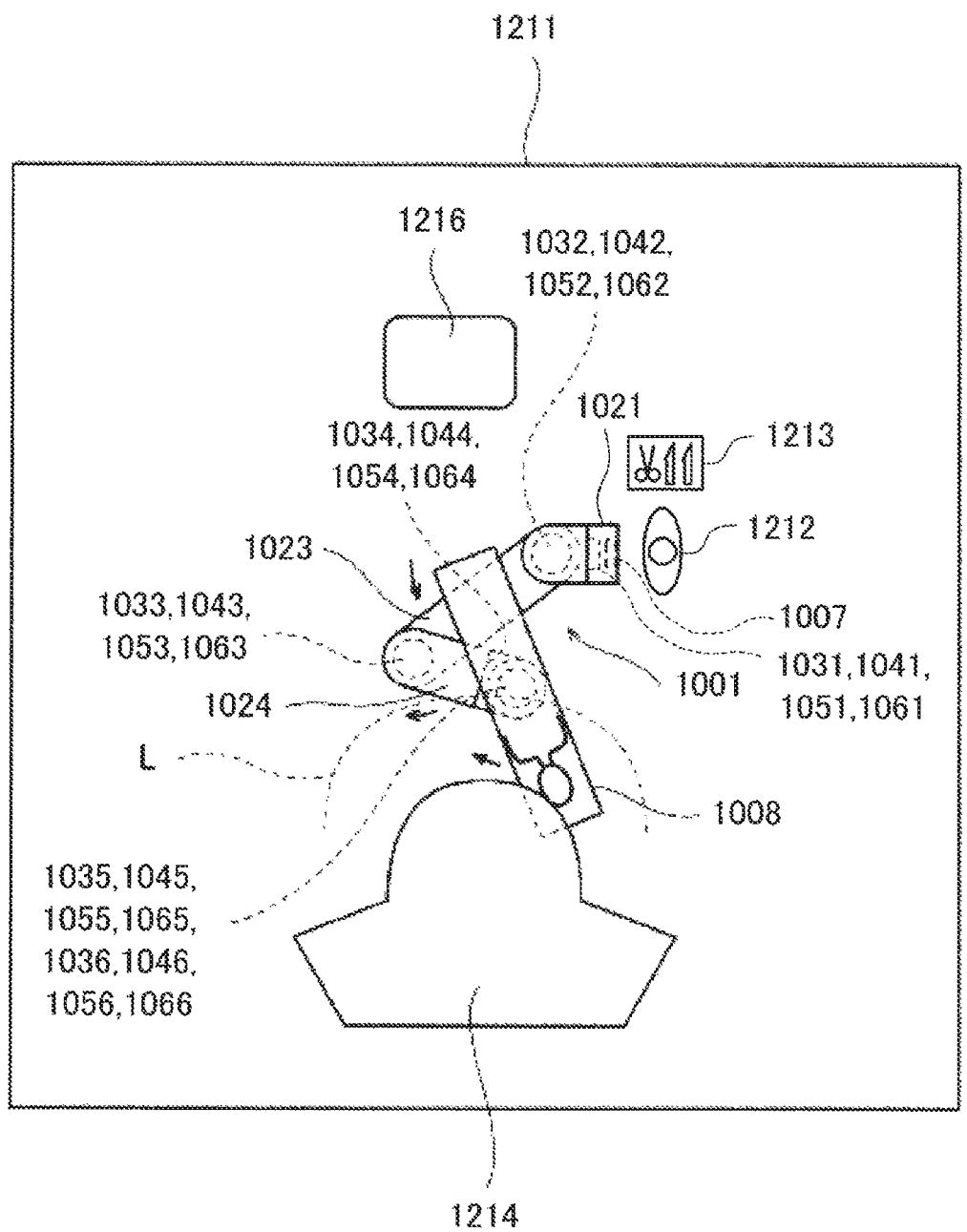
FIG. 13 is a diagram illustrating a plan view of the medical room where the robotic bed according to the second example configuration is placed, and shows the table in the middle of being transferred from the first position to a second position.

FIG. 13 illustrates a state in which the second movable element 1023 and the third movable element 1024 are moved by the control of the controller 1007 as the arrows indicate, and the table 1008 is rotated about the sixth axis as the arrow indicates (in some cases, the first movable element 1022, too, is moved in the vertical direction to have its height adjusted, and the table 1008 is rotated about the fourth axis and/or the fifth axis to have its tilt with respect to the longitudinal direction and/or the width direction of the table finely adjusted), causing the head of the patient to move toward the MRI apparatus 1214 from an oblique angle. FIG. 14 illustrates a state in which the table 1008 is inserted in the MRI apparatus 1214, and the table 1008 has arrived at the MRI scanning position. As illustrated in FIG. 14, of the robot arm 1001, the entire movable element 1022 directly connected to the base 1021, and the second movable element 1023 not directly connected to the base 1021, except the other end portion thereof, are not hidden under the table 1008 at the imaging position, which is the second position. The maximum dimension of the robot arm 1001 not hidden under the table 1008 is at least one fourth (i.e., ¼) of the longitudinal dimension of the table 1008.

Figure 14:
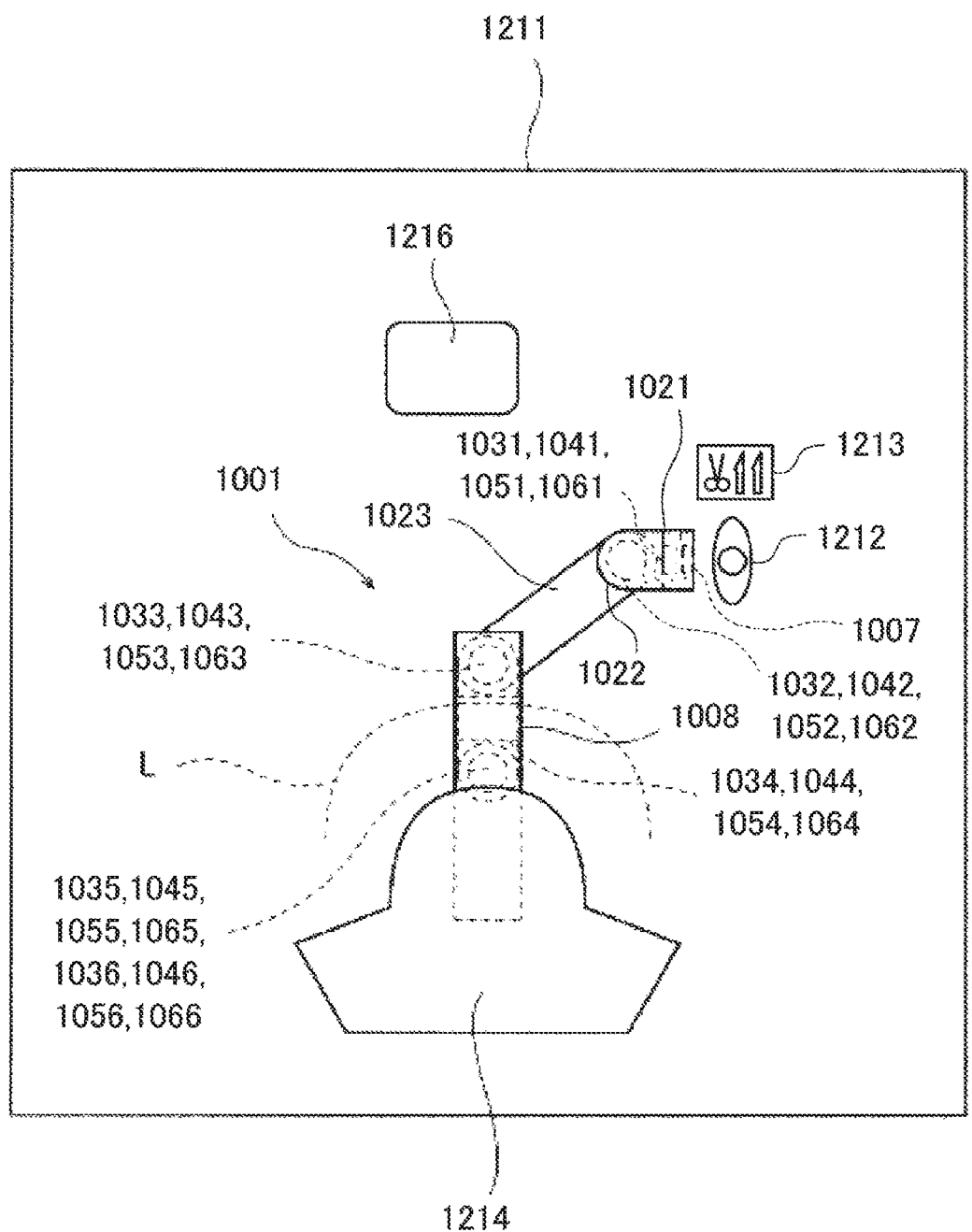
FIG. 14 is a diagram illustrating a plan view of the medical room where the robotic bed according to the second example configuration is placed, and shows a state in which the table is located at the second position.

If the table 1008 needs to be moved to the surgery position after the capturing of images by the MRI apparatus 1214 so that the surgeon 1212 can perform surgery on the patient, the respective movable elements are controlled by the controller 1007 to cause the table 1008 to move in reverse direction from the MRI scanning position (i.e., the second position) illustrated in FIG. 14 to the surgery position (i.e., the first position) illustrated in FIG. 12. The table 1008 returns to the surgery position in this manner, where the surgeon 1201 can immediately start appropriate surgery while viewing the images taken by the MRI apparatus 1214.

Similarly to the case using the robotic bed according to the first configuration, the table 1008 of the second configuration, too, is capable of moving to the anesthesia introducing position, which is the third position.

Figure 40:
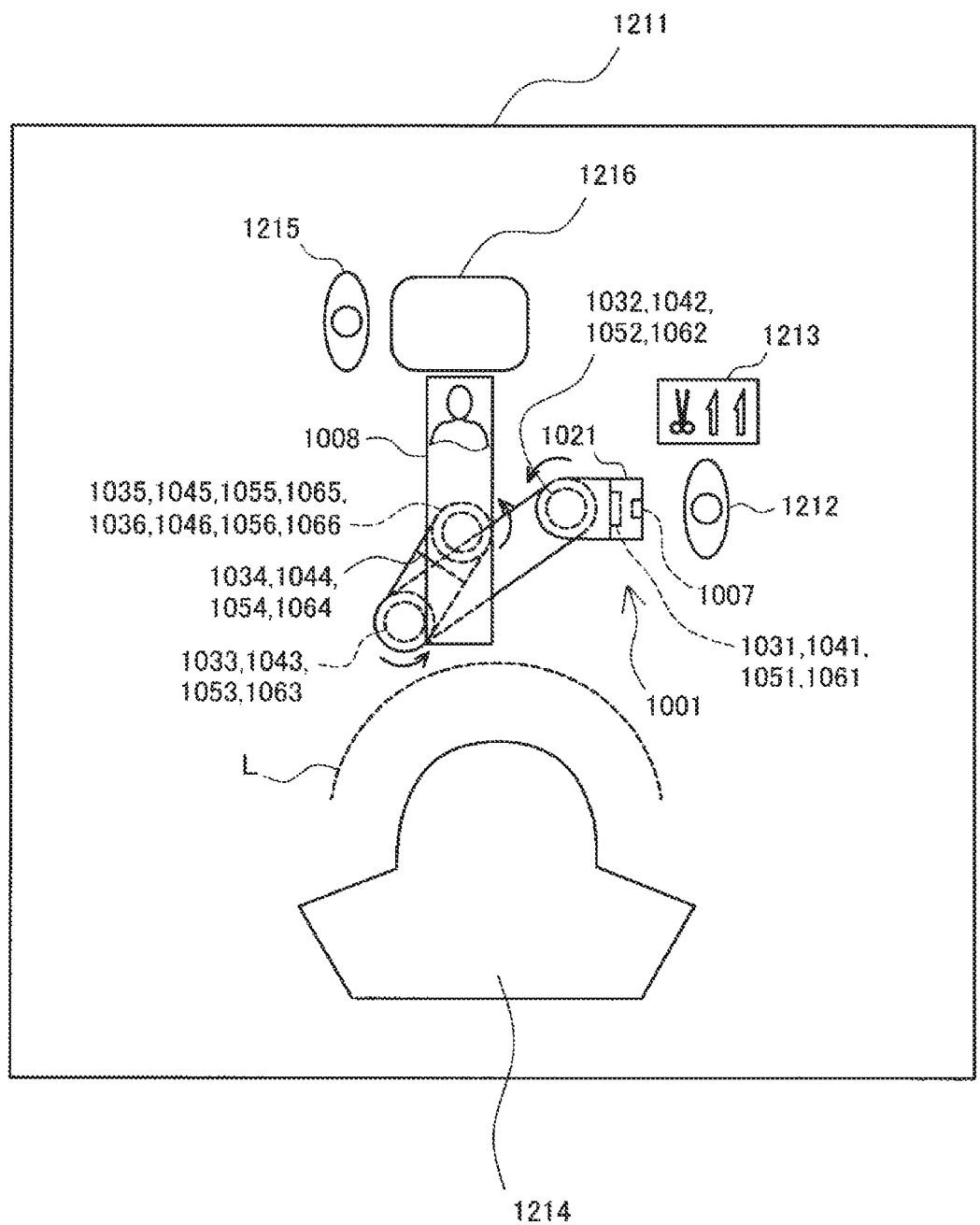
FIG. 40 is a diagram illustrating a plan view of the medical room where the robotic bed according to the second example configuration is placed, and shows a state in which the table is located at a third position.

FIG. 40 illustrates a case in which the patient placement position is different from the anesthesia introducing position, and the same as the surgery position. In FIG. 40, the table 1008 is transferred from the placement position located at the first position to the anesthesia introducing located at the third position.

After the patient is placed on the table 1008 at the first position, the second, third, and sixth joints 1032, 1033, and 1036 are rotated (in some cases, the height of the table 1008 is adjusted by the first joint 1031, and the tilt of the table 1008 with respect to the longitudinal direction and/or the width direction of the table 1008 is adjusted by the fourth and/or fifth joint 1034, 1035) to cause the table 1008 to move as the arrows indicate in FIG. 40 to a position where one end of the table 1008 is close to the anesthesia machine 1216. At the anesthesia introducing position (i.e., the third position) illustrated in FIG. 40, the base 1021 and one end portion of the movable element 1022 which is opposite to the end portion thereof directly connected to the base 1021 are not hidden under the table 1008, when the table 1008 is viewed from vertically above. The maximum dimension of the robot arm 1001 not hidden under the table 1008 is at least one fourth (i.e., ¼) of the longitudinal dimension of the table 1008. Note that this transfer process is omitted if the placement position is the same as the anesthesia introducing position.

The anesthesiologist 1215 then gives anesthesia to the patient. After the completion of the anesthesia, the respective movable elements are moved by the control of the controller 1007 to cause the table 1008 to move in the direction opposite to the direction of the arrows illustrated in FIG. 40, so that the table 1008 is transferred to the surgery position, which is the first position. The surgeon 1212 performs surgery on the patient based on the information of the image captured by the MRI apparatus prior to the surgery. After brain tumors, for example, are removed, the table 1008 is transferred to the imaging position, which is the second position, as described above, where the affected area (e.g., brain) is subjected to MRI. The table 1008 is then transferred back to the surgery position located at the first position. If there is a remaining tumor, for example, the surgeon 1212 continues to perform the surgery.

FIG. 17 illustrates a state in which the table 1508 on which the patient is to be placed is located at the surgery position (i.e., the first position) in the process of moving the table 1508 from the surgery position (i.e., the first position) to the MRI scanning position (i.e., the second position) using the robotic bed according to the third example configuration. As illustrated in FIG. 17, since the table 1508 is located at the first position, portions of the robot arm 1501 which are the base and the one end portion of the movable element connected to the base are not hidden under the table 1508 in the longitudinal direction of the table 1508, and the rest of the robot arm 1501 is hidden under the table 1508, when the table 1508 is viewed from vertically from above. The maximum dimension of the robot arm 1501 not hidden under the table 1508 is shorter than one fourth (i.e., ¼) of the longitudinal dimension of the table 1508.

FIG. 18 illustrates a state in which the second movable element 1523 and the table 1508 are moved by the control of the controller 1507 as the arrows indicate (in some cases, the first movable element 1522, too, is moved in the vertical direction to have its height adjusted, and the table 1508 is rotated about the third axis and/or the fourth axis to have its tilt with respect to the longitudinal direction and/or the width direction of the table finely adjusted), causing the head of the patient to move toward the MRI apparatus 1714 from an oblique angle. FIG. 19 illustrates a state in which the table 1508 is inserted in the MRI apparatus 1514, and the patient has arrived at the MRI scanning position which is the second position. As illustrated in FIG. 19, the entire movable element 1522, of the robot arm 1501, which is directly connected to the base 1521 is not hidden under the table 1508. The maximum dimension of the robot arm 1501 not hidden under the table 1508 is at least one fourth (i.e., ¼) of the longitudinal dimension of the table 1508.

If the table 1508 needs to be moved to the surgery position after the capturing of images by the MRI apparatus 1714 so that the surgeon 1712 can perform surgery on the patient, the respective movable elements are controlled by the controller 1507 to cause the table 1508 to move in reverse direction from the MRI scanning position (i.e., the second position) illustrated in FIG. 19 to the surgery position (i.e., the first position) illustrated in FIG. 17. The table 1508 returns to the surgery position in this manner, where the surgeon 1712 can immediately start appropriate surgery while viewing the images taken by the MRI apparatus 1714.

Now, a case in which the table 1508 is transferred also to the anesthesia introducing position (i.e., the third position) in addition to the surgery position (i.e., the first position) and the imaging position (i.e., the second position) will be described.

Figure 41:
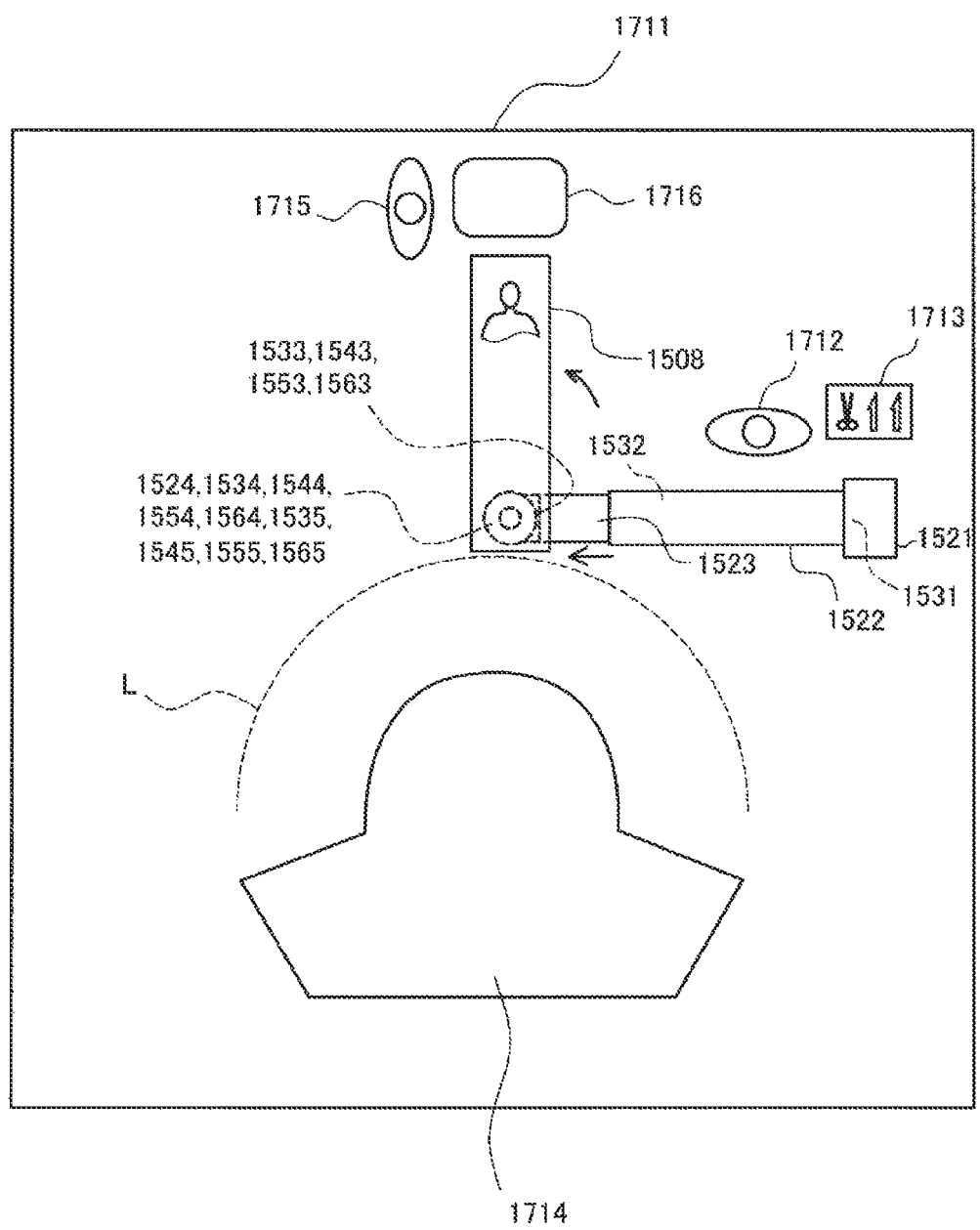
FIG. 41 is a diagram illustrating a plan view of the medical room where the robotic bed according to the third example configuration is placed, and shows a state in which the table is located at a third position.

FIG. 41 illustrates a case in which the patient placement position is different from the anesthesia introducing position, and the same as the surgery position. In FIG. 41, the table 1508 is transferred from the placement position located at the first position to the anesthesia introducing located at the third position.

After the patient is placed on the table 1508 at the first position, the second joint 1532 causes the second movable element 1523 to move straight forward, and the fifth joint 1535 rotates (in some cases, the height of the table 1508 is adjusted by the first joint 1531, and the tilt of the table 1508 with respect to the longitudinal direction and/or the width direction of the table 1508 is adjusted by the third and/or fourth joint 1533, 1534) to cause the table 1508 to move as the arrows indicate in FIG. 41 to a position where one end of the table 1508 is close to the anesthesia machine 1716. At the anesthesia introducing position (i.e., the third position) illustrated in FIG. 41, the base 1521 and the entire movable element 1522 directly connected to the base 1521 are not hidden under the table 1508, when the table 1508 is viewed from vertically above. The maximum dimension of the robot arm 1501 not hidden under the table 1508 is at least one fourth (i.e., ¼) of the longitudinal dimension of the table 1508. Note that this transfer process is omitted if the placement position is the same as the anesthesia introducing position.

The anesthesiologist 1715 then gives anesthesia to the patient. After the completion of the anesthesia, the respective movable elements are moved to cause the table 1508 to move in the direction opposite to the direction of the arrows illustrated in FIG. 41, so that the table 1508 is transferred to the surgery position, which is the first position. The surgeon 1712 performs surgery on the patient based on the information of the image captured by the MRI apparatus prior to the surgery. After brain tumors, for example, are removed, the table 1508 is transferred to the imaging position, which is the second position, as described above, where the affected area (e.g., brain) is subjected to MRI. The table 1508 is then transferred back to the surgery position located at the first position. If there is a remaining tumor, for example, the surgeon 1712 continues to perform the surgery.

FIG. 24 illustrates a state in which the table 2008 on which the patient is to be placed is located at the surgery position (i.e., the first position) in the process of moving the table 2008 from the surgery position (i.e., the first position) to the MRI scanning position (i.e., the second position) using the robotic bed according to the fourth example configuration. As illustrated in FIG. 24, since the table 2008 is located at the first position, the entire robot arm 2001 is hidden under the table 2008 when the table 2008 is viewed from vertically above.

FIG. 25 illustrates a state in which the first and second movable elements 2022 and 2023 and the table 2008 are moved by the control of the controller 2007 as the arrows indicate (in some cases, the third movable element 2024, too, is rotated about the third axis to have its height adjusted, and the table 2008 is rotated about the fifth axis and/or the sixth axis to have its tilt with respect to the longitudinal direction and/or the width direction finely adjusted), causing the head of the patient to move toward the MRI apparatus 2414 from an oblique angle. FIG. 26 illustrates a state in which the table 2008 is inserted in the MRI apparatus 2414, and the table 2008 has arrived at the MRI scanning position. As illustrated in FIG. 26, of the robot arm 2001, the entire movable element 2022 directly connected to the base 2021, and the second movable element 2023 and other elements not directly connected to the base 2021, are not hidden under the table 2008 at the imaging position, which is the second position. The maximum dimension of the robot arm 2001 not hidden under the table 2008 is at least one fourth (i.e., ¼) of the longitudinal dimension of the table 2008.

If the table 2008 needs to be moved to the surgery position after the capturing of images by the MRI apparatus 2414 so that the surgeon 2412 can perform surgery on the patient, the respective movable elements are controlled by the controller 2007 to cause the table 2008 to move in reverse direction from the MRI scanning position (i.e., the second position) illustrated in FIG. 26 to the surgery position (i.e., the first position) illustrated in FIG. 24. The table 2008 returns to the surgery position in this manner, where the surgeon 2412 can immediately start appropriate surgery while viewing the images taken by the MRI apparatus 2414.

Similarly to the case using the robotic bed according to the first to third configurations, the table 2008 of the fourth configuration, too, is capable of moving to the anesthesia introducing position, which is the third position.

Figure 42:
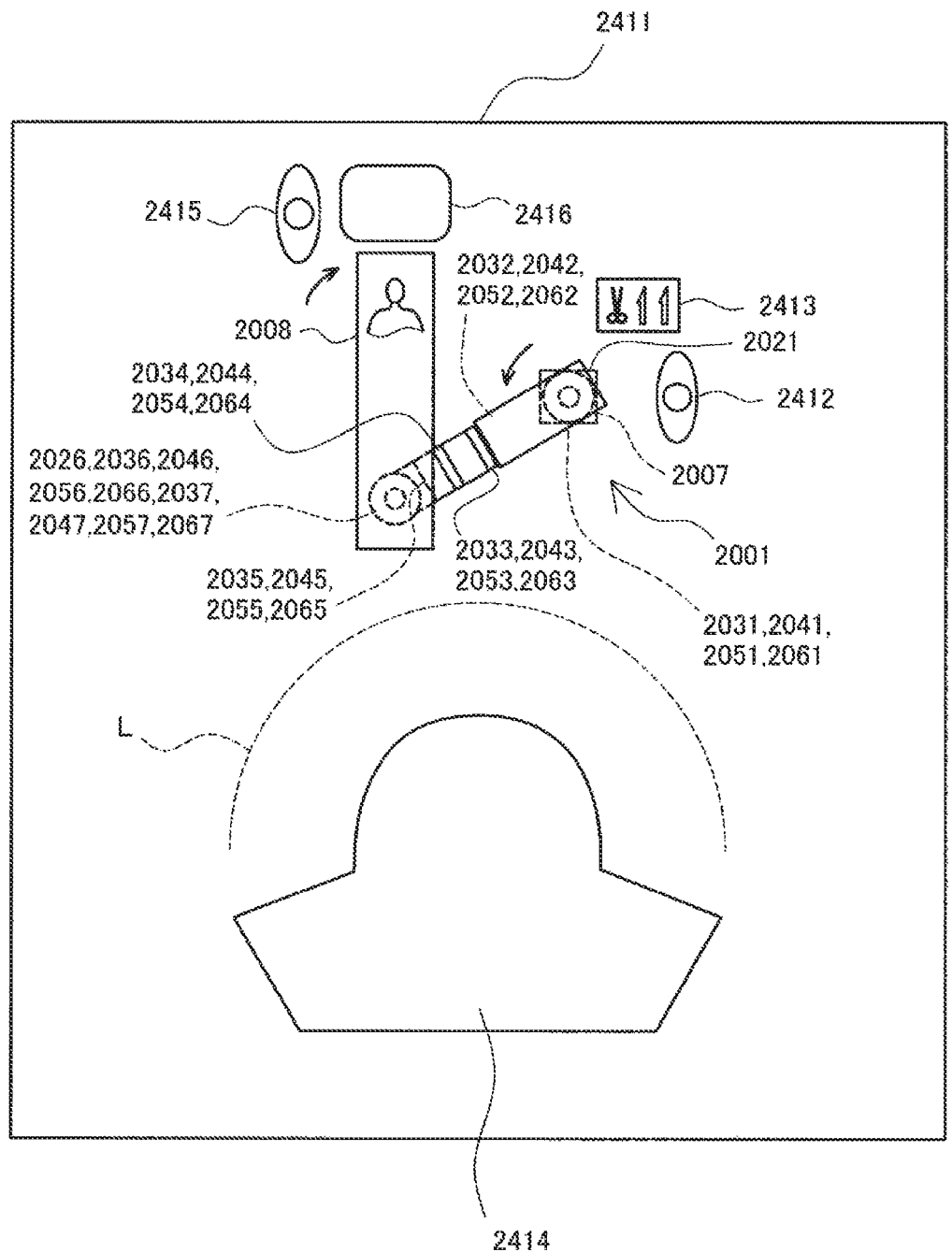
FIG. 42 is a diagram illustrating a plan view of the medical room where the robotic bed according to the fourth example configuration is placed, and shows a state in which the table is located at a third position.

FIG. 42 illustrates a case in which the patient placement position is different from the anesthesia introducing position, and the same as the surgery position. In FIG. 42, the table 2008 is transferred from the placement position located at the first position to the anesthesia introducing located at the third position.

After the patient is placed on the table 2008 at the first position, the first and seventh joints 2031 and 2037 are rotated (in some cases; the height of the table 2008 is adjusted by the third and fourth joints 2033 and 2034; the distance from the base 2021 to the sixth axis is adjusted by the second joint 2032; and the tilt of the table 2008 with respect to the longitudinal direction and/or the width direction of the table 2008 is adjusted by the fifth and/or sixth joint 2035, 2036) to cause the table 2008 to move as the arrows indicate in FIG. 42 to a position where one end of the table 2008 is close to the anesthesia machine 2416. At the anesthesia introducing position (i.e., the third position) illustrated in FIG. 42, the base 2021 and the movable element 2032 directly connected to the base 2021 are not hidden under the table 2008, when the table 2008 is viewed from vertically above. The maximum dimension of the robot arm 2001 not hidden under the table 2008 is at least one fourth (i.e., ¼) of the longitudinal dimension of the table 2008. Note that this transfer process is omitted if the placement position is the same as the anesthesia introducing position.

The anesthesiologist 2415 then gives anesthesia to the patient. After the completion of the anesthesia, the respective movable elements are moved by the control of the controller 2407 to cause the table 2008 to move in the direction opposite to the direction of the arrows illustrated in FIG. 42, so that the table 2008 is transferred to the surgery position, which is the first position. The surgeon 2412 performs surgery on the patient based on the information of the image captured by the MRI apparatus prior to the surgery. After brain tumors, for example, are removed, the table 2008 is transferred to the imaging position, which is the second position, as described above, where the affected area (e.g., brain) is subjected to MRI. The table 2008 is then transferred back to the surgery position located at the first position. If there is a remaining tumor, for example, the surgeon 2412 continues to perform the surgery.

FIGS. 30 to 32 illustrate a case in which the fifth example configuration of the robotic bed (which employs an actuator-driven slide mechanism in the robotic bed according to the first example configuration so as to move the table 2908) is used for the intraoperative MRI.

The surgery position located at the first position in FIG. 30 is the same as that in FIG. 6. However, in the robotic bed having the slide mechanism, the table 2908 moving toward the MRI apparatus 3014 rotates in the opposite direction. In other words, the table 208 illustrated in FIGS. 6 to 8 is inserted into the inspection device 614 from one end of the table 208, whereas the table 2908 illustrated in FIGS. 30 to 32 is inserted into the MRI apparatus 3014 from the other end of the table 2908.

The position (i.e., the MRI scanning position) illustrated in FIG. 8 where the target is inserted into the MRI apparatus 614 from his/her head is the same as the position shown in FIG. 32. In a case using the robotic bed according to the first example configuration, the table 208 is transferred into the MRI apparatus 614 from an oblique angle by simply operating the movable elements of the robot arm 201, whereas in a case using the robotic bed according to the fifth example configuration, the table 2908 is temporarily arranged to face towards the MRI apparatus 3014, and then made to slide into the MRI apparatus 3014 by the actuation of the actuator.

Figure 36:
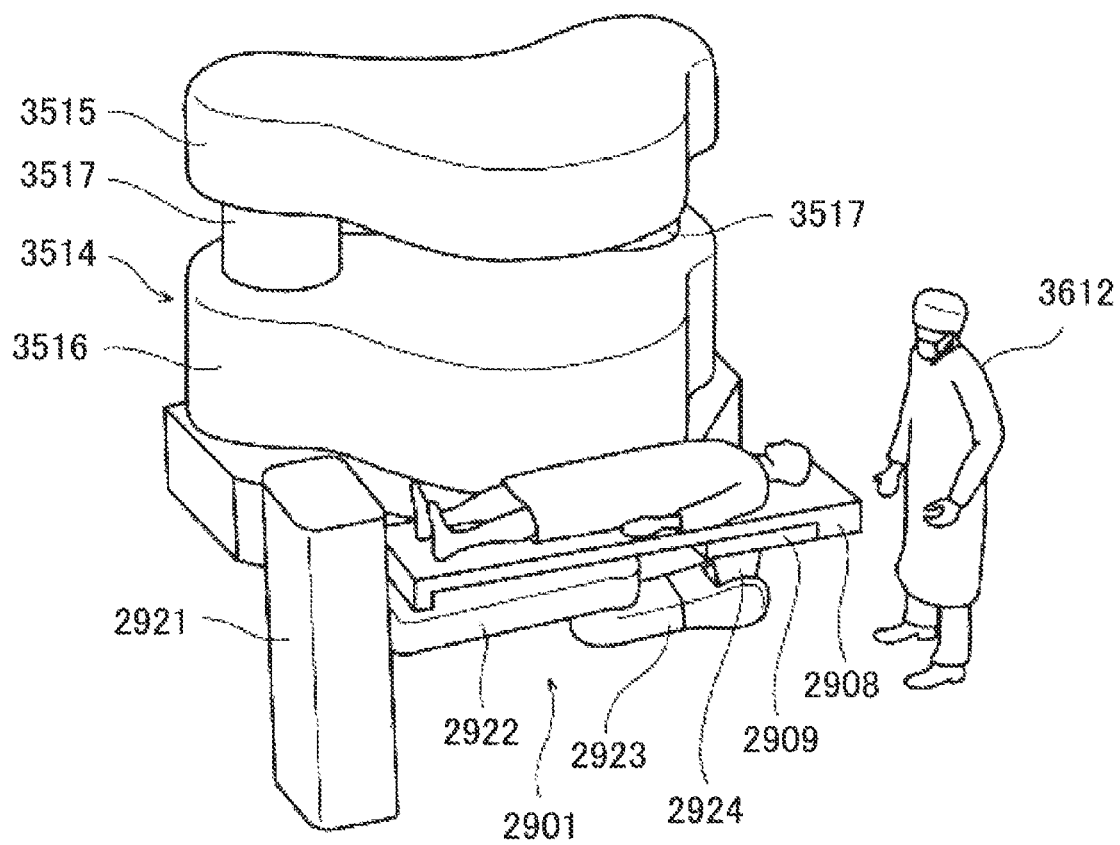
FIG. 36 is a diagram illustrating a perspective view of a case in which the robotic bed according to the fifth example configuration is employed in intraoperative MRI, and shows a state in which the table is located at the surgery position.
Figure 37:
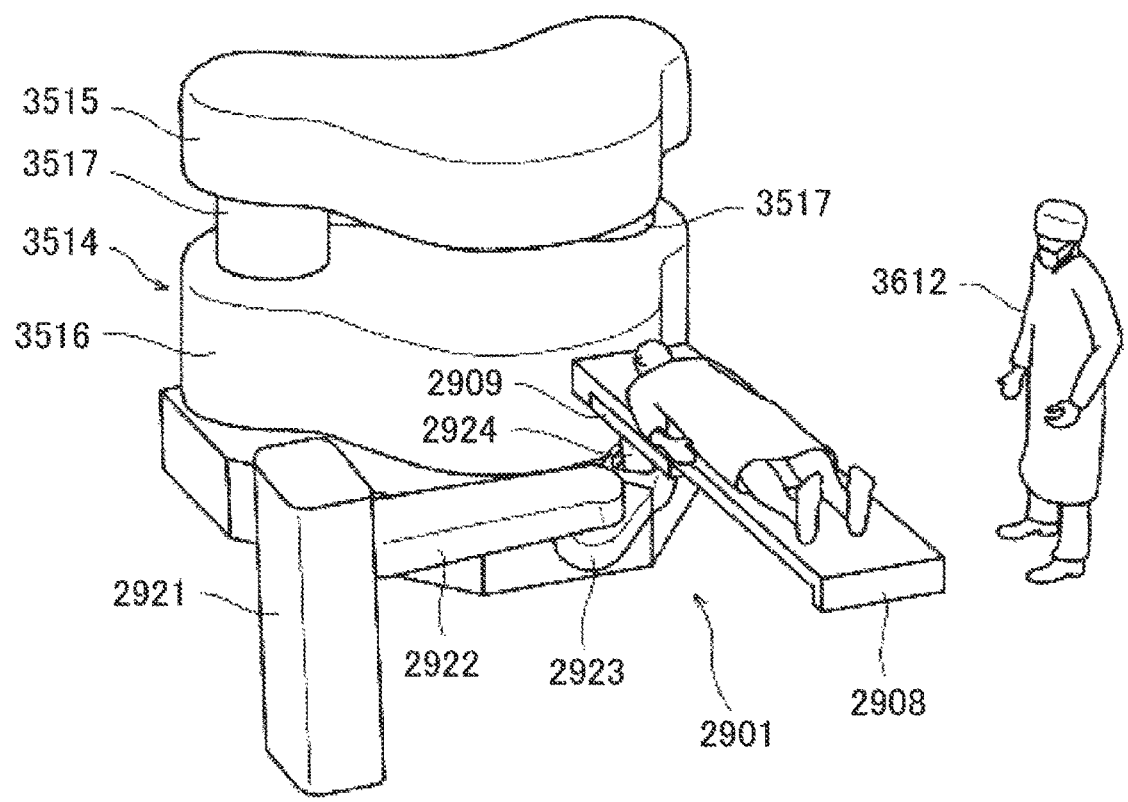
FIG. 37 is a diagram illustrating a perspective view of the case in which the robotic bed according to the fifth example configuration is employed in intraoperative MRI, and shows a state in which the table is located at the imaging preparation position.
Figure 38:
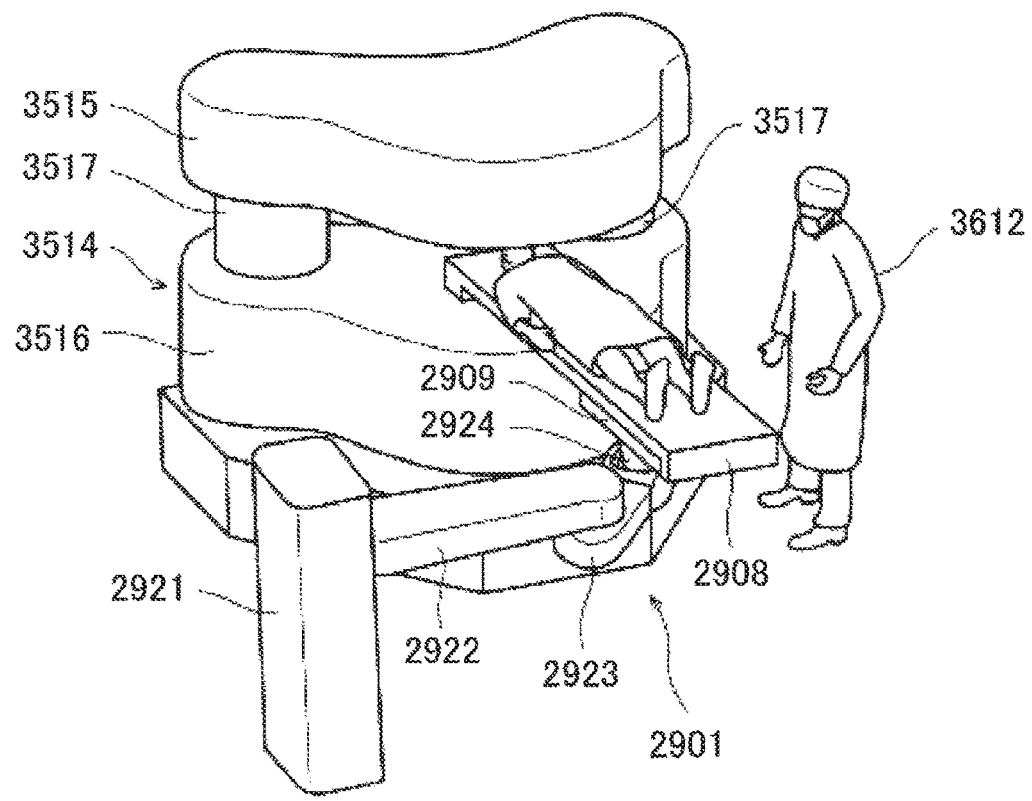
FIG. 38 is a diagram illustrating a perspective view of the case in which the robotic bed according to the fifth example configuration is employed in intraoperative MRI, and shows a state in which the table is located at the imaging position.

FIGS. 36 to 38 are perspective diagrams for illustrating how the robotic bed of the fifth example configuration (which employs an actuator-driven slide mechanism in the robotic bed according to the first example configuration) moves when used in the intraoperative MRI. In FIG. 36, the table 2908 is located at the first position, which is the patient placement position and is also the surgery position. The second movable element 2923 makes a horizontal rotation about the second axis, and at the same time the table 2908 makes an axial rotation about the fifth axis (in some cases, the height of the table 2908 is adjusted by the first joint, and the tilt of the table 2908 with respect to the longitudinal direction and/or the width direction of the table 2908 is adjusted by the third and/or the fourth joint), causing the table 2908 to move to the MRI preparation position illustrated in FIG. 37. Then the table 2908 is slid, by the actuation of the actuator, to a position where the table 2908 overlaps with the imaging space of the MRI apparatus, and moved to the MRI scanning position, which is the second position (FIG. 38).

The direction of the second movable element 2923 at the MRI preparation position in FIG. 37 is different from the direction of the second movable element 2923 at the MRI preparation position on the path of transition from the position in FIG. 31 to the position in FIG. 32. That is, the second movable element 2923 is perpendicular to the MRI apparatus 3014 in the case of transition from the position in FIG. 31 to the position in FIG. 32, whereas in the case of FIG. 37, the second movable element 2923 is positioned at an oblique angle with respect to the MRI apparatus 3014. However, the position of the robot arm during transfer of the table may differ depending on where to install the MRI apparatus, where to install the robotic bed, and the size of each of the movable elements of the robot arm.

The robotic bed according to the fifth example configuration includes a slide mechanism, which may avoid an increase in the length of the first and second movable elements for ensuring a wide range of movement of the table. Thus, provision of the slide mechanism provides an advantage of downsizing the robot arm, and also an effect that the orientation of the head of the placed target at the surgery position (i.e., the first position) is changeable in the robotic bed according to the first example configuration illustrated in FIG. 2 in which the robot arm 201 supports one end portion of the table 208. As for the latter advantage, in a case, for example, where the intraoperative MRI is used to perform surgery relating to the upper body (e.g., removal of brain tumors), the surgeon 612 may have difficulty in performing the surgery if the patient on the table 208 comes back from the MRI apparatus 614 with his/her head directed toward the base 221 as illustrated in FIG. 2, because the base 221 constitutes an obstacle. On the other hand, if the patient on the table 2908 comes back from the MRI scanning position with his/her head directed away from the base 2921 as illustrated in FIG. 29, it is easy to perform the surgery of the upper body, such as the head. Since the base 2921 does not constitute an obstacle on the side close to the upper body during the surgery, the surgeon 3012 may lower the height of the table 2908 and give treatment while seated.

The MRI preparation position illustrated in FIG. 37 is a position where the table 2908 does not overlap with the imaging space, where the particular direction (i.e., the longitudinal direction) of the table 2908 is directed to the opening of the MRI apparatus 3314 when the table 2908 is located close to the imaging position (e.g., 10 cm to 40 cm from the imaging space), and where the table is parallel to the particular direction (i.e., the longitudinal direction) of the table at the imaging position. In the case of the open MRI apparatus, which has a wide opening, the table may be directed to the MRI apparatus in a plurality of different directions. In the case of the donut-shaped MRI apparatus, the direction of the table toward the opening is substantially uniquely determined. The movement of the table 2908 may be stopped for a while at this imaging preparation position, where an assistant, for example, may prepare for the MRI (e.g., check if there is metallic object, and correct the position and posture of the patient), and thereafter the table 2908 may be transferred to the MRI apparatus. Of course, the table may just pass through the MRI preparation position without stopping there for a while, and smoothly move to the MRI scanning position.

The table 2908 of the fifth configuration, too, is capable of moving to the anesthesia introducing position, which is the third position.

Figure 43:
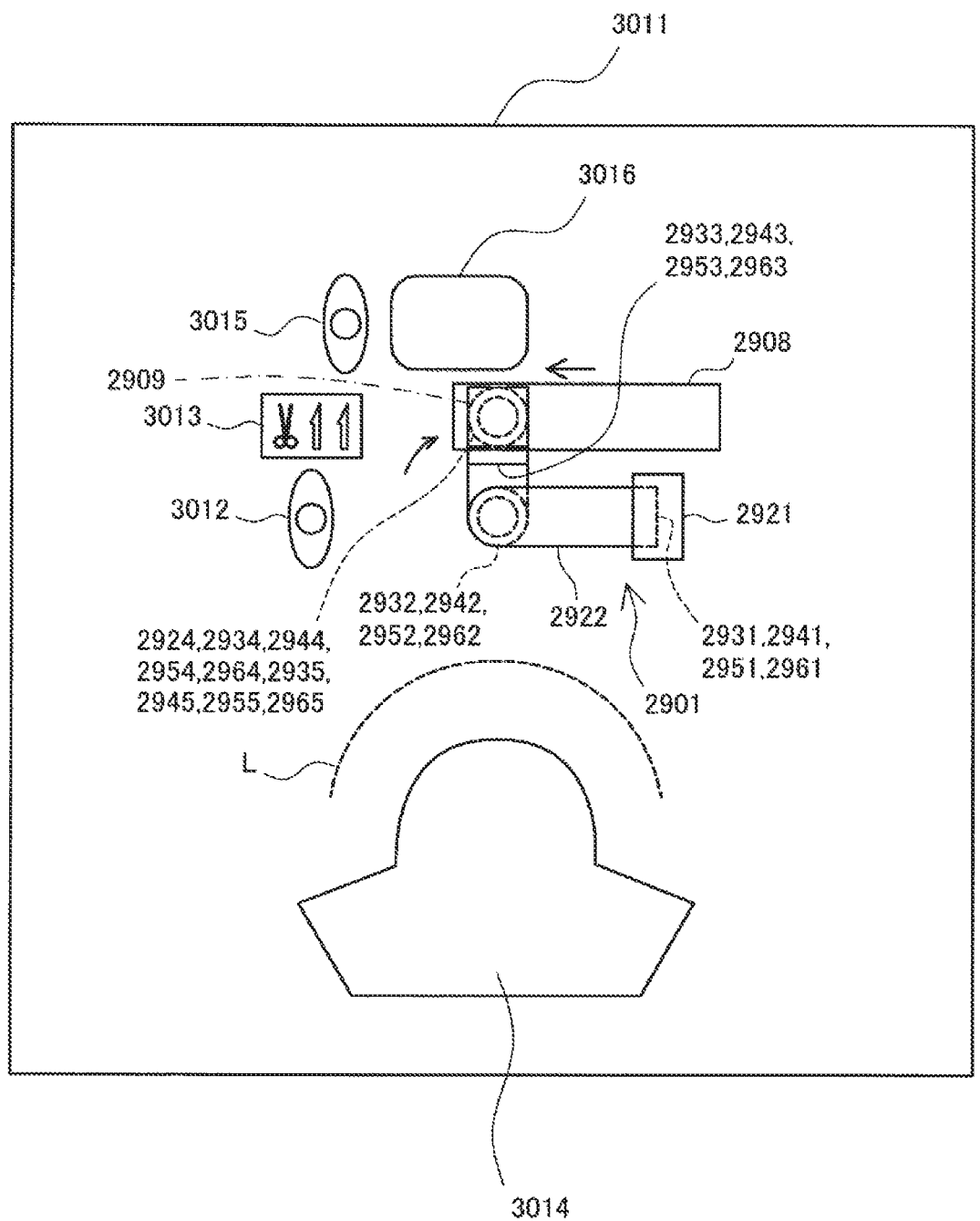
FIG. 43 is a diagram illustrating a plan view of the medical room where the robotic bed according to the fifth example configuration is placed, and shows a state in which the table is located at a third position.

FIG. 43 illustrates a case in which the patient placement position is different from the anesthesia introducing position, and the same as the surgery position. In FIG. 43, the table 2908 is transferred from the placement position located at the first position to the anesthesia introducing located at the third position.

After the patient is placed on the table 2908 at the first position, the second and fifth joints 2932 and 2935 are rotated and the table 2908 is moved in its longitudinal direction by the slide mechanism (in some cases, the height of the table 2908 is adjusted by the first joint 2931, and the tilt of the table 2908 with respect to the longitudinal direction and/or the width direction of the table 2908 is adjusted by the third and/or fourth joint 2933, 2934) to cause the table 2908 to move as the arrows indicate in FIG. 43 to a position where one end of the table 2908 is close to the anesthesia machine 3016. At the anesthesia introducing position (i.e., the third position) illustrated in FIG. 43, the base 2921 and the movable element 2922 directly connected to the base 2921 are not hidden under the table 2908, when the table 2908 is viewed from vertically above. The maximum dimension of the robot arm 2901 not hidden under the table 2908 is at least one fourth (i.e., ¼) of the longitudinal dimension of the table 2908. Note that this transfer process is omitted if the placement position is the same as the anesthesia introducing position.

The anesthesiologist 3015 then gives anesthesia to the patient. After the completion of the anesthesia, the respective movable elements and the slide mechanism are moved by the control of the controller 2907 to cause the table 2908 to move in the direction opposite to the direction of the arrows illustrated in FIG. 43, so that the table 2908 is transferred to the surgery position, which is the first position. The surgeon 2912 performs surgery on the patient based on the information of the image captured by the MRI apparatus prior to the surgery. After brain tumors, for example, are removed, the table 2908 is transferred to the imaging position, which is the second position, as described above, where the affected area (e.g., brain) is subjected to MRI. The table 2908 is then transferred back to the surgery position located at the first position. If there is a remaining tumor, for example, the surgeon 3012 continues to perform the surgery.

The surgery position as the first position described above is located at a position where the table is not close to the imaging space, that is, a position at least a predetermined distance from the imaging space. In the above examples, a surgical instrument table 613, 1213, 1713, 2413, and 3013, on which surgical instruments to be used by the surgeon 612, 1212, 1712, 2412, and 3012 (hereinafter referred to as "612 to 3012") are placed, is disposed near the surgery position. If these surgical instruments are placed close to the MRI apparatus, the surgical instruments may be affected (e.g., may float) by the permanent magnet of the MRI apparatus, and may hurt the patient and those who handle the surgical instruments. It is therefore preferable that the treatment position be sufficiently away from the MRI apparatus, preferably farther away from the 5 Gauss line L.

It is also preferable that the base 221, 421, 521, 1021, 1121, 1521, 1621, 2021, and 2921 (hereinafter referred to as "221 to 2921") of the robot arm be located outside the 5 Gauss line L. The base 221 to 2921 of the robot arm is provided with a big motor, which includes a magnet. If this motor is located close to the MRI apparatus, the magnetic field generated at the imaging space of the MRI apparatus is distorted, which leads to a deterioration of the MRI images.

Thus, it is preferable that the robotic bed comprised of the robot arm and the table be configured such that the surgery position, which is the first position, is determined to be a position where a shortest distance S to the MRI apparatus is at least a predetermined distance. Considering the safety, the shortest distance S is preferably set to be 5 Gauss line L.

Regarding 5 Gauss line, low magnetic field MRI apparatuses have been developed, which, for example, have the static magnetic field strength of 0.3 Tesla and allow the 5 Gauss line to be set at about one meter from the gantry edge (see, "Intelligent Operating Theater and MR-compatible Operating System" MEDIX, 39: 11-16, 2001). Thus, the shortest distance S between the MRI apparatus and the robotic bed located at the first position is preferably at least 1 m. The shortest distance S may be reduced a little, depending on the development of the low magnetic field MRI apparatuses.

The shortest distance S is preferably at least 1.5 m, for example, in order to use an MRI apparatus with a larger magnetic field or ensure a further improvement in safety.

However, if the treatment position, which is the first position, is away from the MRI apparatus, a large robot arm capable of withstanding a heavy load needs to be used so that the table can be transferred to the imaging position, which is the second position, considering, for example, the withstanding load of the table. In a case of using a large robot arm, it is difficult for a large portion of the robot arm to be housed under the table at the surgery place located at the first position (which means that the robot arm constitutes an obstacle while the surgeon and assistants surround the table to carry out surgery). In addition, the increased distance from the MRI apparatus requires an operating room to be increased in size accordingly. It is therefore not that the greater shortest distance S between the MRI apparatus and the robotic bed at the first position, the better.

The first position of the robotic bed is better close to the MRI apparatus as long as sufficient safety can be ensured in a relationship between the robotic bed and the MRI apparatus. For example, in a case of a 1.5 Tesla MRI apparatus, the 5 Gauss line is about 2.8 m from the gantry (i.e., the MRI apparatus) at the shortest distance (see, "Avoid attraction accident of 3T MRI" Toshio Tsuchihashi, INNERVISION, September (2012)). Considering the 5 Gauss line, the rigidity of the robot arm (i.e., stability of the table) and downsizing, the maximum shortest distance S between the MRI apparatus and the robotic bed located at the first position is preferably set to be 3 m or less, for example. In a case of the MRI apparatus having a static magnetic field strength of 0.3 Tesla and the 5 Gauss line of about 1 m, the maximum shortest distance S may be about 2 m, considering a situation in which a person gripping a surgical instrument may stand by the MRI apparatus.

As is also described in the "Avoid attraction accident of 3T MRI" (INNERVISION, September (2012)), the 5 Gauss line forms an oval around the MRI apparatus, and 2.8 m at the shortest distance, and 5 m at the longest distance, from the MRI apparatus in a case of a 1.5 Tesla MRI apparatus. In most cases today, an operation table capable of rotating and elevating and having a slidable top plate is employed in the intraoperative MRI. If the operation table can only make these three types of movement, the position of the operation table which allows the table to move toward the imaging position may be limited, resulting in difficulties in installing the operation table near the shortest distance portion of the 5 Gauss line. The robotic bed, on the other hand, provides a high degree of freedom in determining the transferring direction of the table, as described above, and hence a high degree of freedom in determining the place of installment, as well.

The anesthesia introducing position, which is the third position, is preferably located opposite to the MRI apparatus in the width direction of the table (i.e., the direction orthogonal to the longitudinal direction of the table) when the table is located at the surgery place (i.e., the first position). This is because it is preferable that the anesthesia machine, which does not require mobility in principle, be placed at a different position from a position between the surgery place (i.e., the first position) and the imaging position (i.e., the second position) in the intraoperative MRI in which the table is moved back and forth between the surgery place (i.e., the first position) and the imaging position (i.e., the second position). The shortest distance M between the surgery place (i.e., the first position) and the anesthesia introducing position (i.e., the third position) is preferably at least 80 cm, so that medical equipment (e.g., a surgical microscope) can be placed around the table during surgery. For example, the base portion of the surgical microscope OME-9000 manufactured by Olympus Corporation has a diameter of 80 cm. Thus, if the shortest distance M between the surgery place (i.e., the first position) and the anesthesia introducing position (i.e., the third position) is at least 80 cm, the surgical microscope can be placed around the table without moving the anesthesia machine.

In a case of employing a movable MRI apparatus in a system configuration, the above-described shortest distances and the first to third positions are determined depending on whether the MRI apparatus is moved or fixed during the surgery. For example, if the MRI apparatus is moved from a next room and fixed during the surgery, the shortest distance S may be determined in relation to the fixed position during the surgery. If the MRI apparatus is moved to a particular position only for the purpose of capturing images, and moved back to the setback position after the image capturing, the shortest distance S may be determined in relation to the setback position of the MRI apparatus.

As can be seen from the foregoing description, application of the robotic beds having the first to fifth example configurations to the intraoperative MRI allows the patient placed on the table to be moved between the surgery place (i.e., the first position) and the MRI scanning position (i.e., the second position) quickly and accurately by the operation of the robot arm. This structure may contribute to enhancing the superior effect of improving the performance of surgery. According to the aforementioned document, "JIYUKU-KAN" Vol. 25, Appendix of "Front-line system for total removal of brain tumor which allows increasing survival rate and ensuring postoperative QOL," Hitachi Medical Corporation, INNERVISION, September (2012), compared to the conventional brain tumor removal surgery in which the MRI and surgery have been performed in different rooms, application of the intraoperative MRI in which imaging and surgery are performed in the same room (and further application of information-guided surgery) achieves five-year survival rates of 78% in grade 3 and 19% in grade 4, which are about three times the average conventional five-year survival rates of about 25% in grade 3 and about 7% in grade 4 of the surgery performed in different rooms. Application of the robotic beds having the first to fifth example configurations to the intraoperative MRI allows the table and the patient to be transferred quickly and accurately as described so far, and allows the MRI scanning and the brain tumor removal surgery to be performed efficiently. Also, these robotized beds are highly expected to contribute to further improving the survival rate. In particular, as explained earlier, in the brain tumor removal surgery, the MRI scanning and the brain tumor removal surgery are not performed only once, but are repeated several times. Thus, there are high expectations for the quick and accurate transfer of the patient between the treatment position and the MRI scanning position.

In applying the robotic beds of the first to fifth example configurations to the intraoperative MRI, it is preferable that the supply of a drive current to the plurality of actuators mounted on the robot arm 201 to 2901 be stopped and the brake functions of the plurality of electromagnetic brakes associated with the actuators be turned on by the control of the controller 207 to 2907, during a period after the table 208 to 2908 has arrived at the MRI scanning position 614, 1214, 1714, 2414, 3014, and 3514 and before images of the target placed on the table starts to be taken. This configuration is intended to reduce the deterioration of the MRI images due to effects of the magnetic field generated while the actuators are actuated, for the MRI apparatus takes images by utilizing the static magnetic field. This control may be automatically carried out when the controller detects that the table has arrived at the MRI scanning position and stayed there for a predetermined period of time, or may be carried out in accordance with a manually entered instruction. It is preferable, however, that the start of MRI scanning (e.g., at a time when the main power of the MRI apparatus is turned on, or the MRI apparatus is turned into an active state) trigger the checking of whether the actuators of the robot arm are actuated or not. If the actuators are actuated, the actuators are forcedly turned off to have the brake functions turned on. It is therefore preferable that the controller 207 to 2907 have an MRI operation monitor to monitor, for example, whether the main power of the MRI apparatus is turned on or whether the MRI apparatus is turned into an active state.

In some cases, the robot arm of the fifth example configuration may be provided with a man-powered slide mechanism. Thus, the supply of the drive current to the plurality of actuators mounted on the robot arm 201 to 2901 may be stopped and the brake functions of the plurality of electromagnetic brakes associated with the actuators may be turned on by the control of the controller 207 to 2907 at a time when the table 208 to 2908 arrives at the MRI preparation position. After the actuators are turned off and the brake functions of the electromagnetic brakes are turned on, the slide plate is made to slide to move the patient to the MRI scanning position.

The table may be moved between the surgery place and the MRI scanning position by actuating the robot arm 201 to 2901 through a teaching pendant. However, if the surgery place and the MRI scanning position are stored in advance in the controller 201 to 2907, the table 208 to 2908 may move between the surgery place and the MRI scanning position more quickly and smoothly according to a movement control program for the table 208 to 2908 with respect to the first, second and/or third position. For example, if the table is configured to move according to this movement control program only during a forward-movement instruction given through a teaching pendant, safety is ensured because the execution of the program is interrupted by stopping the forward-movement instruction (e.g., stopping pushing the button).

In a case where the robot arm automatically transfers the table between the surgery place and the MRI scanning position, it is the accuracy of the positioning of the robot arm that brings the surgical field back to exactly where it used to be after the MRI scanning. Another advantage of using the robot arm is that it is possible to ensure a wide surgical field during surgery by operating the robot arm and changing the position and posture of the patient during the surgery.

(Case Using Apparatus Other than MRI Apparatus as Medical Imaging Device)

In a case in which an apparatus other than the MRI apparatus is used as the medical imaging device, a system design is slightly different from the case in which the intraoperative MRI is used, because it is not necessary to take measures against the magnetic field in introducing the robotic bed. However, table movements, for example, are basically the same as those in the case in which the MRI apparatus is used as the medical imaging device.

If an apparatus other than the MRI apparatus is used as the medical imaging device, the device 614 in FIGS. 6 to 8, the device 1214 in FIGS. 12 to 14, the device 1714 in FIGS. 17 to 19, the device 2414 in FIGS. 24 to 26, and the device 3014 in FIGS. 30 to 32, which are referred to in describing the movement of the table in the respective example configurations, are angiographic devices, for example. In FIGS. 6, 12, 17, 24, and 30, the tables 208 to 2908 are each located at the surgery place, which is the first position. Similarly to the case in which the MRI apparatus is used as the medical imaging device, the respective movable elements and the table 208 to 2908 are moved in the directions indicated by the arrows shown in FIGS. 7, 13, 18, 25, and 31, causing the table 208 to 2908 to reach at the imaging position (i.e., the second position) illustrated in FIGS. 8, 14, 19, 26, and 32.

The imaging position and the imaging preparation position may be the same as those in the case where the MRI apparatus is used as the medical imaging device. That is, it can be said that the table 208 to 2908 is located at the imaging position, where images are taken by the medical imaging device, when at least part of the table 208 to 2908 overlaps with the imaging space of the medical imaging device. In a case where the medical imaging device is an angiographic device, the imaging space is defined by an X-ray tube (i.e., an X-ray irradiation side) and an imaging system (i.e., an X-ray receiving side). The imaging preparation position is a place where the table 208 to 2908 is close to the imaging space, but does not overlap with the imaging space.

Examples of the anesthesia introducing position, which is the third position, are illustrated in FIGS. 39, 40, 41, 42, and 43. In a case where the placement position and the surgery place are located at the same first position, the positions illustrated in these figures are where the table has reached at the anesthesia introducing position. In a case where the placement position and the anesthesia introducing position are located at the same third position, the positions illustrated in these figures are the placement position and the anesthesia introducing position. Similarly to the case in which the MRI apparatus is used as the medical imaging device, the anesthesia introducing position (i.e., the third position) is preferably located opposite to the angiographic device with respect to the table width direction when the table is located at the first position.

At the imaging position, which is the second position, images of a specific site (an affected area) of the patient is taken by X-ray fluoroscopy using the angiographic device. Then, the table 208 to 2908 is moved to the surgery place (i.e., the first position) to give catheter treatment or any other treatment.

Examples of the angiographic device includes a ceiling traveling type in which the angiographic device is suspended from the ceiling and travels along the rail provided on the ceiling, a floor-fixed type in which a support of the device is fixed to the floor such that the body (i.e., a C-shaped portion) of the device is rotatable about a vertical axis, and a floor traveling type in which a support of the device is provided with casters, and the device as a whole can travel on the floor on the casters. Taking images by any one of these angiographic devices is called single-plane imaging. Bidirectionally performing fluoroscopy and imaging at one time, using two angiographic devices (e.g., the ceiling traveling type and the floor-fixed type) in combination, is called biplane imaging. The biplane system is widely used due to its effects of reducing a burden on the patient, that is, reducing imaging time, exposure dose, and the amount of a contrast agent to be used.

Regardless of whether the single-plane system or multi-plane system is used, the first to third positions are determined on the same basis.

Figure 44A:
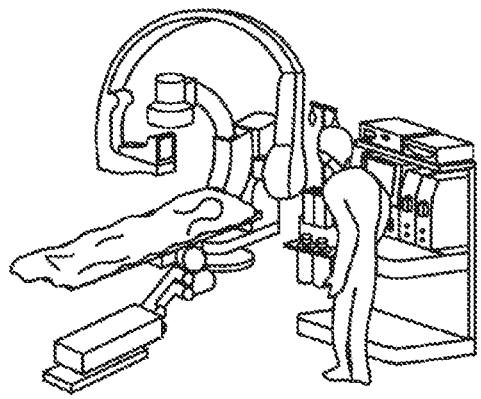
FIGS. 44A to 44F are perspective views and their corresponding plan views, illustrating the robotic bed according to the fourth example configuration provided with a slide mechanism being transferred from the first position to the second position.
Figure 44B:
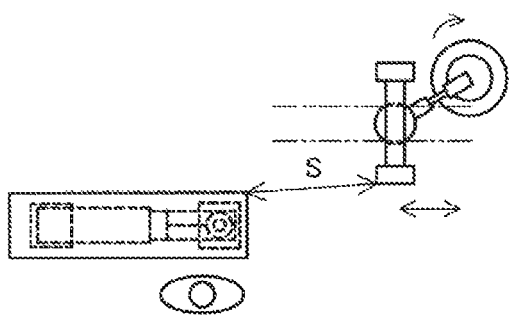
Figure 44C:
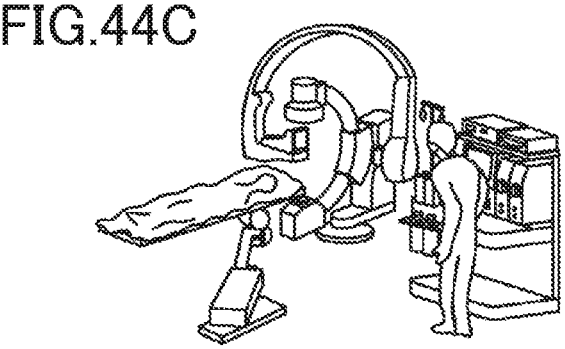
Figure 44D:
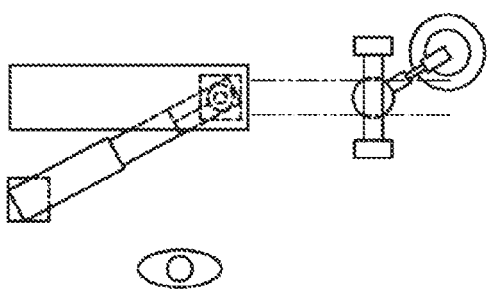
Figure 44E:
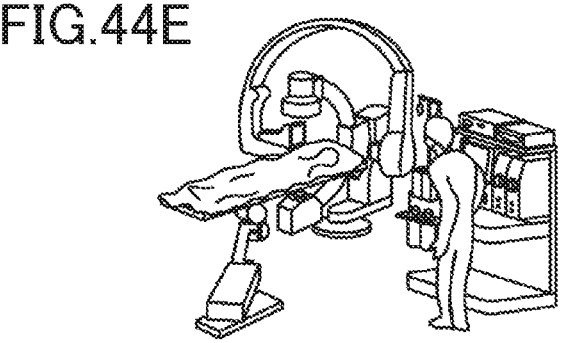
Figure 44F:
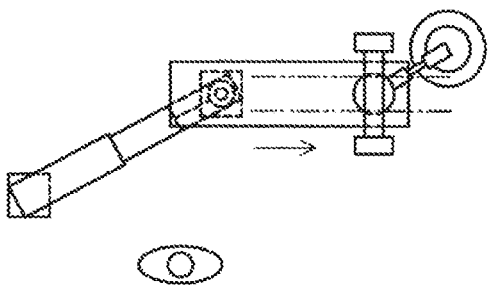

FIGS. 44A to 44F are diagrams illustrating an example in which a biplane angiographic device comprised of a combination of the ceiling traveling type and the floor-fixed type is used as the medical imaging device. In this example, a robotic bed having the fourth example configuration (illustrated in FIG. 22) and equipped with a slide mechanism is used to move the table from the surgery place (i.e., the first position) to the imaging position (i.e., the imaging position). FIGS. 44A, 44C, and 44E are perspective views. FIGS. 44B, 44D, and 44F are plan views of the operating room as viewed from vertically above.

In FIGS. 44A and 44B, the table is located at the surgery place, which is the first position, where the entire robot arm is hidden under the table. In FIGS. 44C and 44D, the first and sixth joints are rotated, and the second joint is extended and retracted to adjust the distance between the sixth joint and the base (in some cases, the third joint is rotated to adjust the height of the table, and the tilt of the table with respect to the longitudinal direction and/or the width direction of the table is adjusted), causing the table to reach at the imaging preparation position. In FIGS. 44D and 44F, the table has reached at the imaging position (i.e., the second position) by the actuation of the slide mechanism.

How the first position is determined in the case where the angiographic device is used as the medical imaging device is similar to how the first position is determined in the case where the MRI apparatus is used as the medical imaging device. The first position is determined in consideration of the shortest distance S between the angiographic device and the robotic bed at the surgery place (i.e., the first position). In the case where the angiographic device is used as the medical imaging device, it is not necessary to take the 5 Gauss line into account because it is not necessary to take the effect of magnetic properties into account. However, the shortest distance S is preferably set to be at least a predetermined distance from the angiographic device when the table is located at the surgery place (i.e., the first position) so that the surgeon and the assistants may surround the table. In the hybrid operation, too, using the angiographic device as the medical imaging device, the shortest distance S is preferably set to be at least a predetermined distance from the angiographic device so that medical equipment (e.g., a surgical microscope) can be placed around the table during surgery. The shortest distance S may be at least 80 cm, considering, for example, the diameter of the base portion of the surgical microscope, so that the surgical microscope can be placed between the robotic bed and the angiographic device.

Further, similarly to the case using MRI apparatus as medical imaging device, it is not that the greater shortest distance S between the angiographic device and the robotic bed at the first position, the better, considering the load of the table supported by the robot arm, how much the robot arm located at the surgery place (i.e., the first position) can be stored under the table (that is, downsizing of the robot configuration), and the rigidity of the robot arm (that is, stability of the table). Thus, the shortest distance S between the angiographic device and the robotic bed at the first position is preferably set to be, for example, 80 cm to allow the surgical microscope to be installed, and further to be 2 m or less, considering a space to allow a person to pass therethrough.

Next, in the case where the medical imaging device is a ceiling traveling type or floor-fixed type angiographic device, the device can move back and forth between the imaging position and the setback position by moving the device along the rail, or rotating the body (the C-shaped portion) of the device with respect to the support of the device, even during the surgery.

Figure 45A:
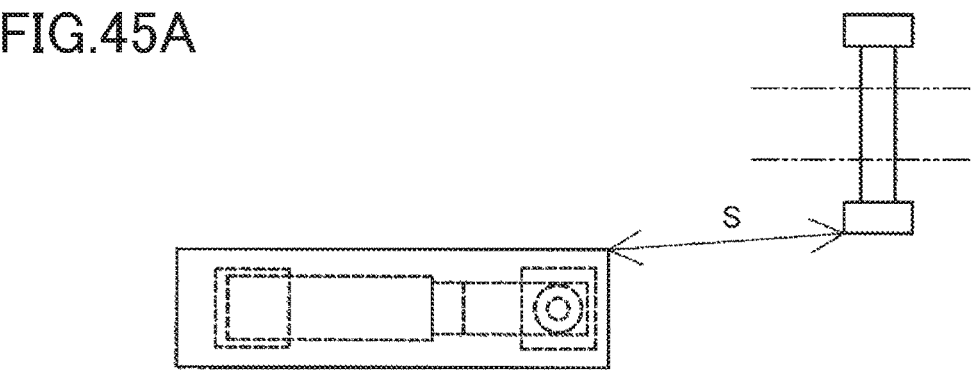
FIGS. 45A, 45B, and 45C are plan views illustrating the shortest distance between the robotic bed and the first position when the angiographic device is located at a setback position.
Figure 45B:
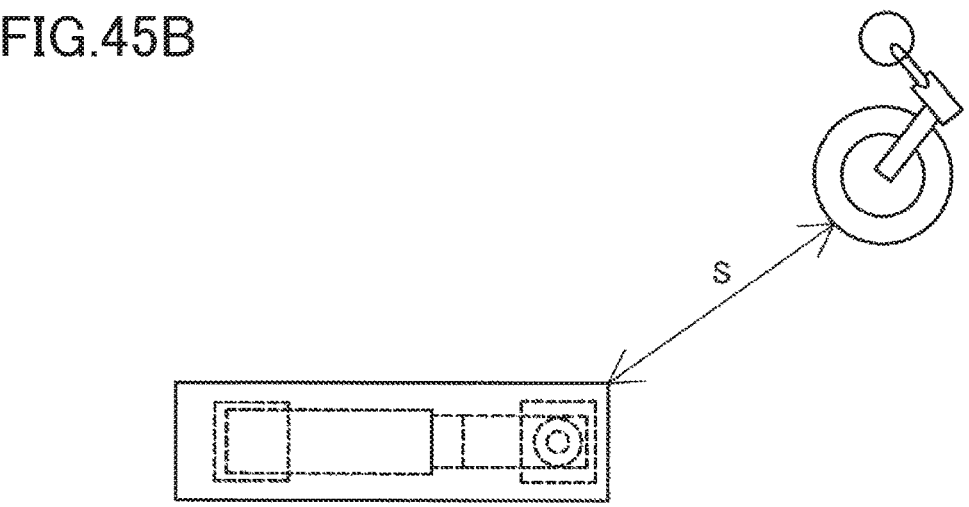
Figure 45C:
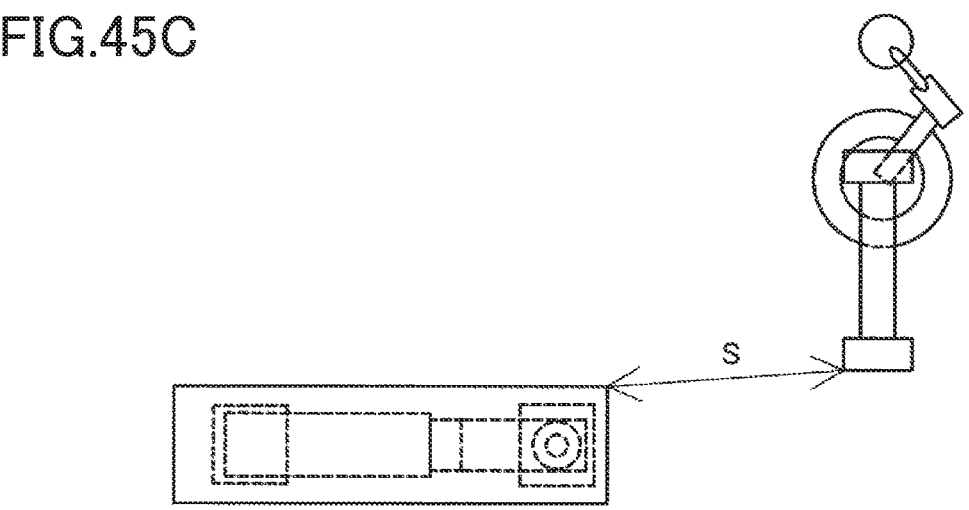

FIGS. 45A, 45B, and 45C are diagrams illustrating the shortest distance S between the angiographic device located at the setback position and the table located at the surgery place (i.e., the first position). FIG. 45A illustrates a setback position of a single-plane angiographic device of a ceiling traveling type. FIG. 45B illustrates a setback position of a single-plane angiographic device of a floor-fixed type. FIG. 45C illustrates a setback position of a biplane angiographic device comprised of a ceiling traveling type and floor-fixed type.

If the angiographic device can move to the setback position, the system configuration in relation to the robotic bed depends on how the hybrid operation is carried out. A first system is configured such that the angiographic device stays at the imaging position (i.e., the second position) even in a case where the table is moved back and forth between the surgery place (i.e., the first position) and the imaging position (i.e., the second position), and that the angiographic device is moved to the setback position only when the hybrid operation is not carried out. In this case, the shortest distance S may be determined not in relation to the setback position illustrated in FIGS. 45A, 45B, and 45C, but in relation to the imaging position (i.e., the second position) illustrated in FIGS. 44A to 44F. In the aforementioned example, the shortest distance S may be set to be from 80 cm to 2 m. A second system is configured such that the angiographic device is moved to the setback position when the table is located at the surgery place (i.e., the first position) and the angiographic device is moved to the imaging position when the table is located at the imaging position (i.e., the second position), that is, the position of the angiographic device is changed in relation to the robotic bed during the hybrid operation. In this case, the shortest distance S is determined in relation to the setback position of the angiographic device illustrated in FIGS. 45A to 45C. In this example, the shortest distance S between the setback position of the angiographic device and the robotic bed when the table is located at the surgery place (i.e., the first position) may be from 80 cm to 2 m.

Figure 46A:
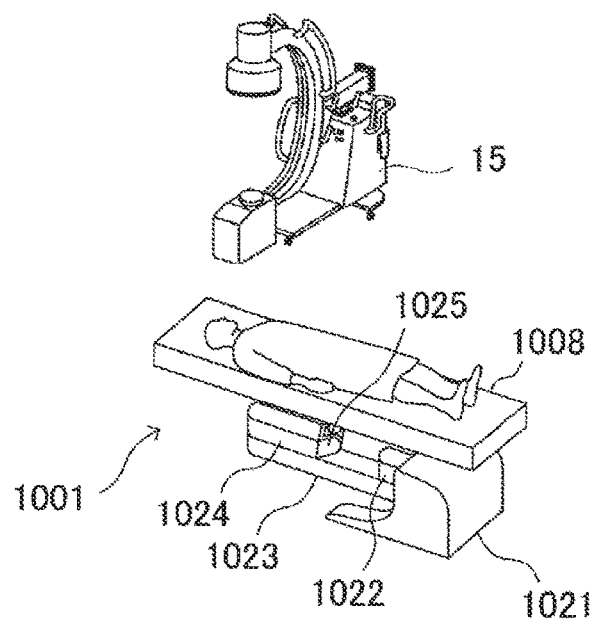
FIGS. 46A, 46B, and 46C are diagrams illustrating perspective views of the robotic bed according to the second example configuration which is used in combination with an angiographic device of a floor traveling type.
Figure 46B:
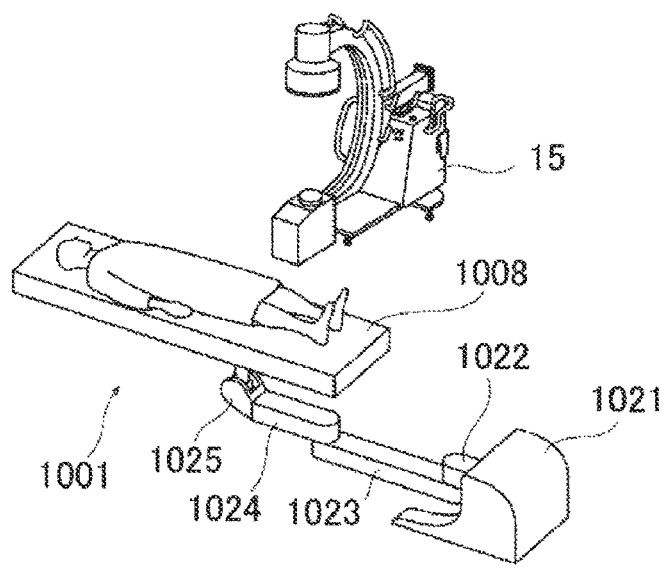
Figure 46C:
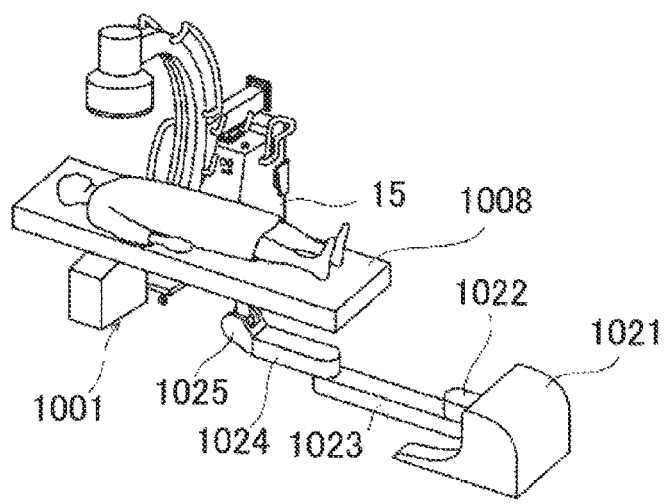

These two system configurations are applicable to a case in which the angiographic device is of the floor traveling type as illustrated in FIGS. 46A, 46B, and 46C. That is, the shortest distance S between the robotic bed and the angiographic device can be determined in relation to the imaging position (i.e., the second position) or the setback position, depending on whether the angiographic device stays at the imaging position, or is moved each time an image is taken, during the hybrid operation.

A case in which the angiographic device is used as a medical imaging device other than the MRI apparatus has been described. Similar system configurations are applicable to cases using devices, such as a computerized tomography (CT) scanner, a digital radiographic (DR) imager, a computed radiographic (CR) system, and an ultrasonographic (US) system.

Figure 49:
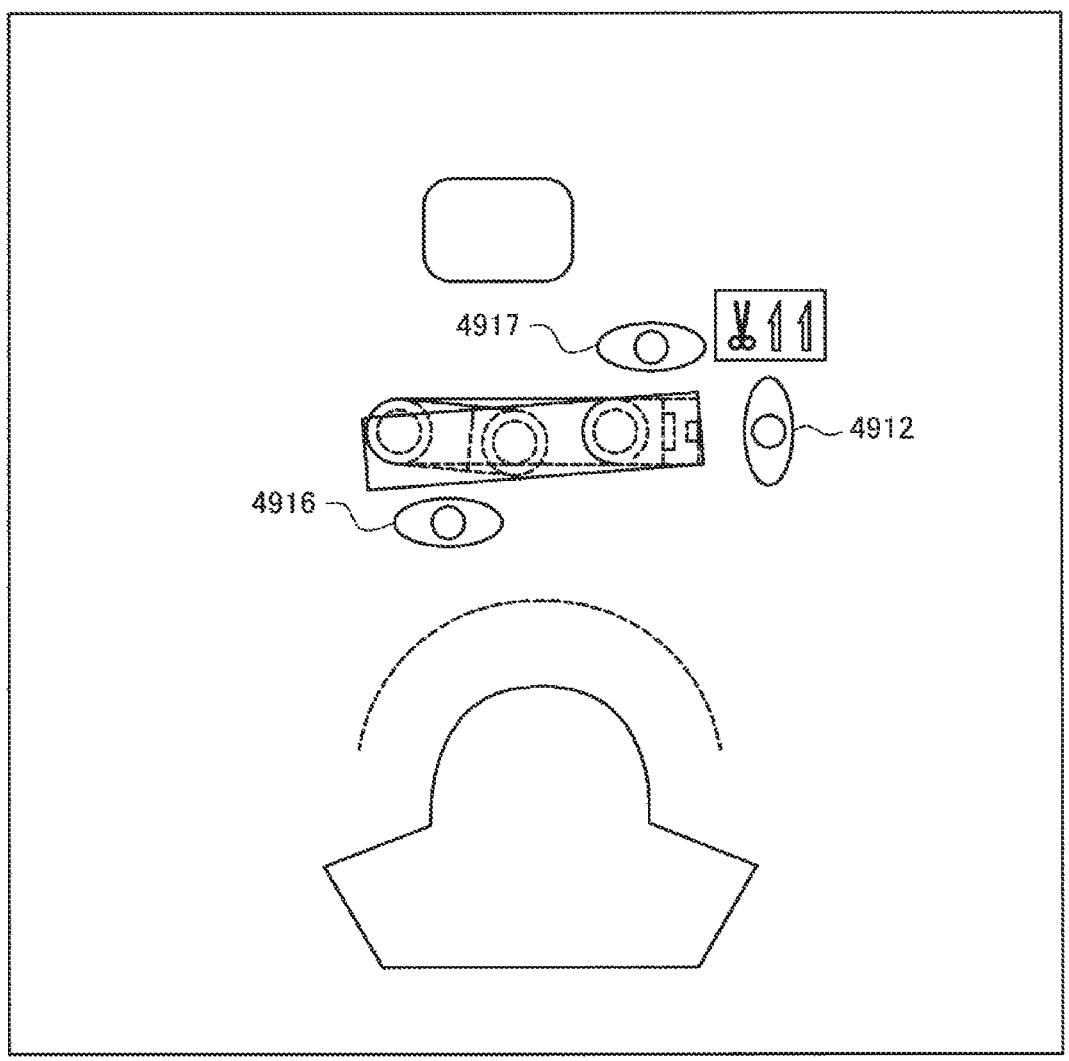
FIG. 49 is a diagram illustrating a plan view of the medical room where the robotic bed according to the second example configuration is placed, and shows a state in which the table is located at the first position.

In each of FIGS. 6, 12, 17, 24, and 30, the entire portion of the robot arm other than at least the base and the one end portion of the movable element directly connected to the base is hidden under the table at the first position in the hybrid operation, when viewed from vertically above. As long as the robot arm does not constitute an obstacle to the surgeon and assistants surrounding the table, a small portion of the robot arm other than the one end portion of the movable element directly connected to the base may not be hidden under the table. That is, it is sufficient if a large portion of the robot arm other than at least the base and the one end portion of the movable element directly connected to the base is hidden under the table. For example, in FIG. 49, the table at the first position (i.e., the surgery place) is slightly displaced from the position illustrated in FIG. 12. At this position, part of the robot arm (the second and third movable elements) other than the one end portion of the movable element directly connected to the base protrude slightly from under the table. The table located at this position does not constitute an obstacle to the surgeon 4912, the assistant 4916, and the nurse 4917 (illustrated, for example, in FIG. 49) surrounding the table to perform surgery. If such protrusion of the robot arm occurs at only one end of the table in its width direction, for example, and the total protrusion amount is less than one third (i.e., ⅓) of the width dimension of the table, the slightly protruded portion can be ignored and it can be said that "the maximum dimension of part of the robot arm which is not hidden under the table is less than one fourth (i.e., ¼) of the longitudinal dimension of the table" and also that "a large portion of the robot arm other than the one end portion of the movable element directly connected to the base is hidden under the table." If the protrusion amount of the robot arm from under the table is one third (i.e., ⅓) or more of the width dimension of the table, it can be said that "a certain portion of the robot arm is not hidden under the table (that is, protrudes from the table)."

Figure 51:
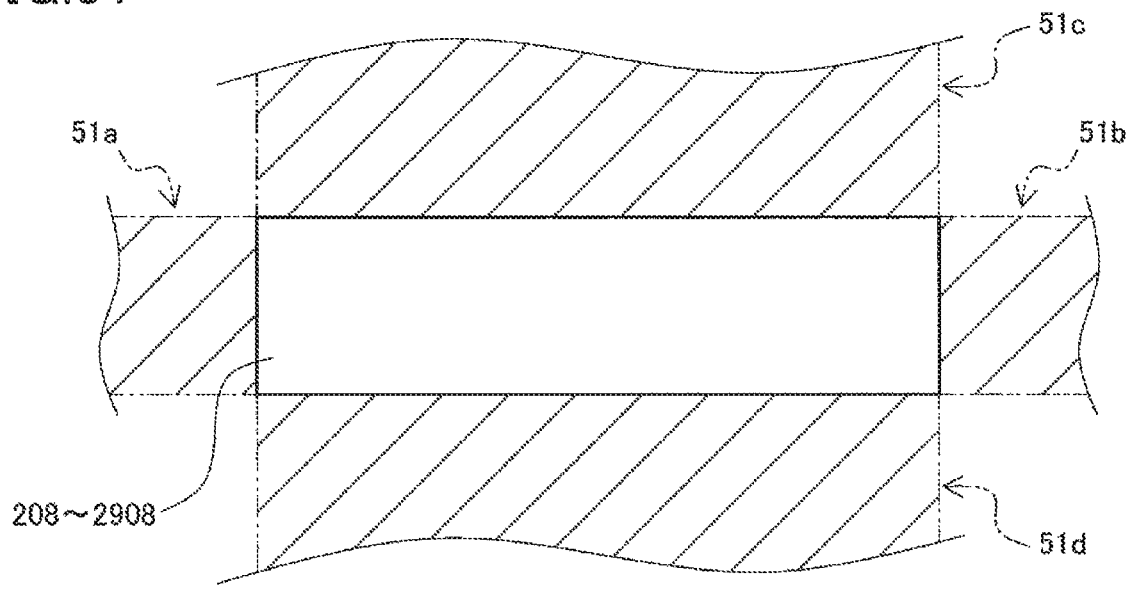
FIG. 51 is a diagram illustrating areas having widths corresponding to respective sides of the table in its longitudinal direction and width direction.

Further, it is preferable that, at the first position, the robot arm is not hidden under the table at only one side in the longitudinal and width directions of the table, and that the portions of the robot arm which are not hidden under the table (e.g., the base and one end portion of the first movable element 222, 422, 522, 1522, 1622, 2922 directly connected to the base in the first, third, and fifth example configurations) overlap, on the one side, with an area having a width corresponding to the one side. That is, a rectangular table defined by the longitudinal and width dimensions has four sides. If the robot arm is not required to be hidden under the table, the robot arm should protrude so as to overlap with only one of areas 51a to 51d (see FIG. 51) having widths corresponding to the four sides. Regarding the robotic beds having the first and third example configurations, the base of the robot arm protrudes from only one side, in the longitudinal direction, of the table and overlaps with the area (51a or 51*b*) having a width corresponding to the one side. For example, in a case in which the robotic beds having the second and fourth example configurations are configured such that part of the robot arm protrudes from the table when the robotic bed is located at the first position, the robot arm protrudes from only one side, in the width direction, of the table and overlaps with the area (51*c* or 51*d*) having a width corresponding to the one side. If the first position is the surgery place, such a configuration of the robotic bed still allows the surgeon, the assistant, and the nurse to stay close to at least the three sides of the table.

Unlike the robotic bed used only for image taking by a medical imaging device, the above-described robotic bed used in a hybrid operation is required to move so as to perform an appropriate surgery according to a surgical method at the surgery place. Thus, it is preferable that the robot arm be designed such that the vertical position of the table can be lowered at least to 70 cm and preferably to 50 cm from the floor surface, and increased at least to 100 cm and preferably to 120 cm from the floor surface. For example, in a case in which the table is moved in the vertical direction while staying parallel to the horizontal plane as illustrated in FIG. 23, the distance H1 from the floor surface to the top surface of the table when the table is located at the lowermost position is 50 cm or more and 70 cm or less, and the distance H2 from the floor surface to the top surface of the table when the table is located at the uppermost position is 100 cm or more and 120 cm or less.

In the above-described hybrid operation, only one medical imaging device (i.e., a modality) is used in combination with the robotic bed. However, a plurality of medical imaging devices may be used in combination with the robotic bed. In such a case, positioning of the medical imaging devices may be determined based on the same basis as described above. It is preferable, however, to redesign the medical system in consideration of the positional relationship among the medical imaging devices, and where to install the anesthesia machine, for example.

Hybrid operations, as described above, require a plurality of people, such as a surgeon, an assistant, and a nurse, to surround the table to perform surgery, and therefore differ from the treatment, such as radiotherapy, in which a large treatment device, such as an accelerator, is placed near the table. Hybrid operations also differ from the radiotherapy in which the surgeon is not allowed to approach the table due to the risk of exposure. In such sense, hybrid operations can be defined as operations in which a surgeon, an assistant, and a nurse, for example, can make direct access to the patient.

For such a reason relating to the surgery type, a compact operation table, not a bulky one, is desired in the hybrid operation. Demand for space reduction may also be one of the reasons why the operation tables which are capable of elevating and rotating and having a slidable top plate have been widely used in the hybrid operation.

As described above, the robotic beds having the above example configurations are operable while requiring approximately the same or even smaller space which the operation table capable of rotating and elevating and having a slidable top plate requires. Thus, the robotic beds described above are suitable for use in the hybrid operation, as well. In addition, the above-described robotic beds have wider range of movement, compared with the operation table capable of elevating and rotating and having a slidable top plate, and also have flexibility since the table is free to move three-dimensionally within the range of movement. Further, since the two-dimensional movement of the table is not limited to sliding and rotation, where to install the robotic bed in relation to the medical imaging device can be flexibly determined.

[Application to Other Treatments]

The robotic beds having the above first to fifth example configurations (in some cases, the robotic beds with the above-described common additional features) may be applied not only to the hybrid operation, but also to other treatments as well.

For example, the device 614 in FIGS. 6 to 8, the device 1214 in FIGS. 12 to 14, the device 1714 in FIGS. 17 to 19, the device 2414 in FIGS. 24 to 26, and the device 3014 in FIGS. 30 to 32, which are referred to in describing the movement of the table in the respective example configurations, may be X-ray machines. After a patient is placed on the table 208, 1008, 1508, 1608, 2008, 2908, the table is moved to the imaging position to x-ray the teeth of the patient, and successively moved to the treatment position to give teeth treatment.

Figure 47:
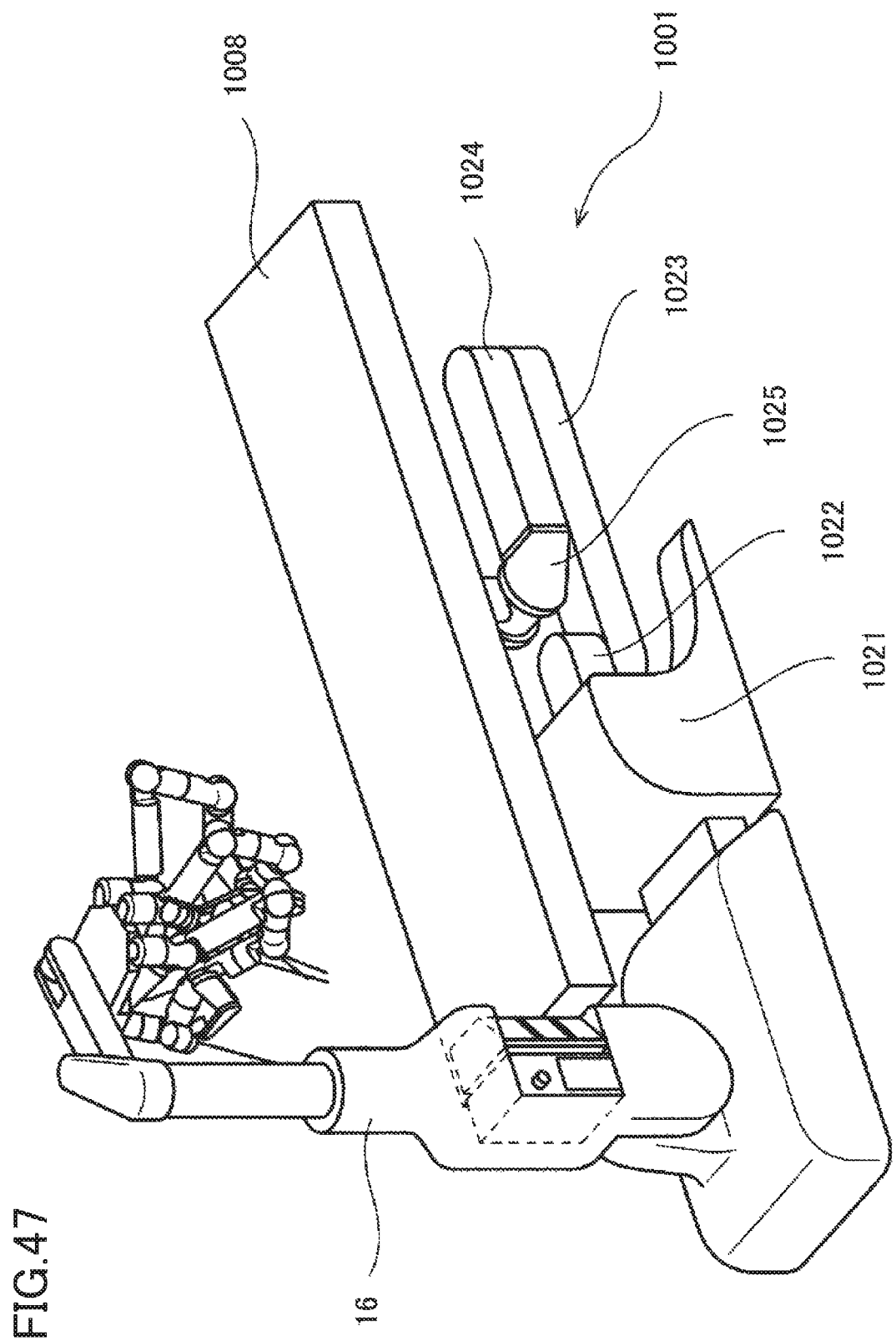
FIG. 47 illustrates a perspective view of the robotic bed according to the second example configuration used in combination with a surgery assisting robot.

Another example is that a surgical robot is arranged at the surgery place illustrated in FIGS. 6 to 8, 12 to 14, 17 to 19, 24 to 26, and 30 to 32 which are referred to in describing the movement of the table in the respective example configurations. At a surgery preparation position, a cannula, for example, is inserted in a patient to make the patient ready for laparoscopic surgery, and thereafter the patient is moved to the surgery place, where the surgical robot performs the laparoscopic surgery with its remotely-controlled manipulator. FIG. 47 is a diagram illustrating a state in which the table 1008 of the robotic bed having the second example configuration has moved to the treatment position where the surgical robot is located.

In these cases, as well, the above-mentioned common features may be added. For example, if the robotic beds having the first to fifth example configurations are used to move the table to the imaging position where images are taken by the angiographic device, the above-described height sensor may be provided. If the height of the table detected by the height sensor is not within the opening area of the C-shaped arm, the movement of the angiographic device or the movement of the table by the robot arm may be stopped.

Examples in which the robotic beds of the first to fifth example configurations are applied to various scenes in the medical settings have been described above. However, the one or more embodiments may be modified in various manners without departing from the scope of one or more embodiments. For example, the table is illustrated as having a rectangular shape in each drawing, but may be in any shape, such as T-shape. In either case, the longitudinal direction and the width direction of the table can be identified unless the table is in a shape, such as a square, a regular triangle, and a circle. The maximum lengths in the respective directions may be determined as the longitudinal dimension and the width dimension of the table. The foregoing description has been made on the premise that the base of the robot arm is fixed. However, depending on the layout of the medical room, the base may be installed on a rotating floor, and may be moved in accordance with the rotation of the floor. Further, a medical room may be provided with a rail via which the base can move. In these configurations, too, in which the base itself is movable, the table can move to the above respective positions by combining the movement of the table with the control of the robot arm.

Note that the terms "bed" and "table" used in the above description are synonyms, and different terms may have been used to clarify the portion being described.

What is claimed is:

1. A medical system comprising:
a medical imaging device; and
a robotic bed comprising
a base,
a table,
a slide mechanism including a body and a slide member that slidably supports the table with respect to the body,
a robot arm having movable elements connected by joints having five or more degrees of freedom, and connected to the base at a proximal end of the robot arm, and supporting the body of the slide mechanism at a distal end of the robot arm, wherein the robot arm is configured to move the table between a surgery position and an imaging preparation position away from the medical imaging device, and the slide mechanism is configured to move the table between the imaging preparation position and an imaging position where an image is taken by the medical imaging device, and
a controller,
wherein the robot arm includes: actuators respectively provided with the joints to move the movable elements; and electromagnetic brakes respectively provided with the joints to stop movements of the movable elements, wherein drive currents supplied to the actuators turn on the actuators and turn off brake functions of the electromagnetic brakes, and drive currents stopped from being supplied to the actuators turn off the actuators and turn on the brake functions of the electromagnetic brakes, and
wherein the controller is configured to control, after the table has arrived at the imaging preparation position and before starting the imaging of a target placed on the table at the imaging position, to stop the drive currents to the actuators to turn off the actuators and turn on the brake functions of the electromagnetic brakes.

2. The medical system of claim 1, wherein
the surgery position comprises a position in which a shortest distance between a location of the medical imaging device and the table is at least a predetermined distance and in which a maximum dimension of the robot arm not hidden under the table is less than one fourth of a longitudinal dimension of the table when the table is viewed from vertically above, and
the imaging position comprises a position in which the maximum dimension of the robot arm not hidden under the table is one fourth of the longitudinal dimension of the table or more when the table is viewed from vertically above.

3. The medical system of claim 2, wherein
at the surgery position, a large portion of the robot arm other than the base and one end portion of the movable element directly connected to the base is hidden under the table, and
wherein at the imaging position, a certain or larger portion of the robot arm other than the base and the one end portion of the movable element directly connected to the base is not hidden under the table.

4. The medical system of claim 2, wherein
at the surgery position, a portion of the robot arm is not hidden under the table at only one side in longitudinal and width directions of the table, and the portion of the robot arm not hidden under the table overlaps, on the one side, with an area having a width corresponding to the one side.

5. The medical system of claim 1, wherein
the medical imaging device comprises an MRI, and
wherein the surgery position comprises a position in which a shortest distance between a location of the medical imaging device and the table is at least a predetermined distance, and the predetermined distance is 5 Gauss line.

6. The medical system of claim 2, wherein
the medical imaging device comprises an MRI, and
the predetermined distance is at least 1 m.

7. The medical system of claim 1, wherein
the medical imaging device comprises an imaging device other than an MRI.

8. The medical system of claim 2, wherein
the medical imaging device comprises an imaging device other than an MRI, and
the predetermined distance is 80 cm or more and 2 m or less.

9. The medical system of claim 1, wherein
at the surgery position, the entire robot arm is hidden under the table when the table is viewed from vertically above.

10. The medical system of claim 1, wherein
the robot arm supports the table so as to be capable of tilting the table with respect to each of a longitudinal direction and a width direction of the table by the joints.

11. The medical system of claim 1, wherein
the joints of the robot arm comprise a joint traveling straight.

12. The medical system of claim 1, wherein
the joints of the robot arm comprise a horizontally-rotating joint coupling ends of the movable elements.

13. The medical system of claim 1, wherein
the joints of the robot arm comprise a vertically-rotating joint.

14. The medical system of claim 13, wherein
when the table takes a lowermost position at the surgery position, the movable elements coupled to each other by the vertically-rotating joint overlap with each other when viewed from a horizontal direction.

15. The medical system of claim 1, wherein
the robotic bed comprises a fixing member for fixing tubes of a medical instrument attached to the target on the table.

16. The medical system of claim 1, further comprising:
a memory configured to store the surgery position and/or the imaging preparation position; and
an instruction device configured to give an instruction to move to the surgery position and/or the imaging preparation position.

17. The medical system of claim 1, wherein
the slide member comprises a rack and pinion or a ball screw.

18. The medical system of claim 1, wherein
the slide member comprises a servomotor to slide the table with respect to the body.

19. A medical system, comprising:
a medical imaging device; and
a robotic bed comprising
a base,
a table,
a slide mechanism including a body and a slide member that slidably supports the table with respect to the body,
a robot arm having movable elements connected by joints, and connected to the base at a proximal end of the robot arm, and supporting the body of the slide mechanism at a distal end of the robot arm, and supporting the table so as to be capable of tilting the table with respect to each of a longitudinal direction and a width direction of the table by the joints, and a controller, wherein the robot arm is configured to move the table between a surgery position and an imaging preparation position away from the medical imaging device, and the slide mechanism is configured to move the table between the imaging preparation position and an imaging position where an image is taken by the medical imaging device, wherein the robot arm includes: actuators respectively provided with the joints to move the movable elements; and electromagnetic brakes respectively provided with the joints to stop movements of the movable elements, wherein drive currents supplied to the actuators turn on the actuators and turn off brake functions of the electromagnetic brakes, and drive currents stopped from being supplied to the actuators turn off the actuators and turn on the brake functions of the electromagnetic brakes, and wherein the controller is configured to control, after the table has arrived at the imaging preparation position and before starting the imaging of a target placed on the table at the imaging position, to stop the drive currents to the actuators to turn off the actuators and turn on the brake functions of the electromagnetic brakes.

20. A medical system, comprising:

a medical imaging device; and a robotic bed comprising a base, a table, a slide mechanism including a body and a slide member that slidably supports the table with respect to the body, a robot arm having movable elements connected together by joints, and connected to the base at a proximal end of the robot arm, and supporting the body of the slide mechanism at a distal end of the robot arm, and a controller, wherein the robot arm is configured to move the table among an anesthesia introducing position, a surgery position, and an imaging preparation position away from the medical imaging device, and the slide mechanism is configured to move the table between the imaging preparation position and an imaging position where an image is taken by the medical imaging device, wherein the robot arm includes: actuators respectively provided with the joints to move the movable elements; and electromagnetic brakes respectively provided with the joints to stop movements of the movable elements, wherein drive currents supplied to the actuators turn on the actuators and turn off brake functions of the electromagnetic brakes, and drive currents stopped from being supplied to the actuators turn off the actuators and turn on the brake functions of the electromagnetic brakes, and wherein the controller is configured to control, after the table has arrived at the imaging preparation position and before starting the imaging of a target placed on the table at the imaging position, to stop the drive currents to the actuators to turn off the actuators and turn on the brake functions of the electromagnetic brakes.

\* \* \* \* \*